US011684678B2

(12) United States Patent
Correia Dos Santos et al.

(10) Patent No.: US 11,684,678 B2
(45) Date of Patent: Jun. 27, 2023

(54) PLASMA-DERIVED NANOPARTICLES

(71) Applicant: THE HEART RESEARCH INSTITUTE LTD, Newtown (AU)

(72) Inventors: Miguel Angelo Correia Dos Santos, Paddington (AU); Elysse Filipe, Paddington (AU); Praveesuda Lorwattanapongsa, Newtown (AU); Marcela Bilek, Southerland (AU); Steven Garry Wise, Panania (AU)

(73) Assignee: NANOMEDX, INC., Santa Clara, CA (US)

( * ) Notice: Subject to any disclaimer, the term of this patent is extended or adjusted under 35 U.S.C. 154(b) by 43 days.

(21) Appl. No.: 16/471,180

(22) PCT Filed: Dec. 21, 2017

(86) PCT No.: PCT/AU2017/051437
§ 371 (c)(1),
(2) Date: Jun. 19, 2019

(87) PCT Pub. No.: WO2018/112543
PCT Pub. Date: Jun. 28, 2018

(65) Prior Publication Data
US 2020/0023074 A1 Jan. 23, 2020

(30) Foreign Application Priority Data
Dec. 21, 2016 (AU) .................. 2016905306

(51) Int. Cl.
*A61K 47/69* (2017.01)
*A61K 47/62* (2017.01)
*A61K 47/68* (2017.01)
*A61K 9/16* (2006.01)
*A61K 49/00* (2006.01)
*C08F 138/02* (2006.01)
*C12N 15/113* (2010.01)

(52) U.S. Cl.
CPC ........ *A61K 47/6933* (2017.08); *A61K 9/1635* (2013.01); *A61K 9/1676* (2013.01); *A61K 9/1694* (2013.01); *A61K 47/62* (2017.08); *A61K 47/6835* (2017.08); *A61K 49/0034* (2013.01); *A61K 49/0093* (2013.01); *C08F 138/02* (2013.01); *C12N 15/1136* (2013.01)

(58) Field of Classification Search
CPC ............. A61K 47/6933; A61K 9/1635; A61K 9/1676; A61K 9/1694; A61K 47/62; A61K 47/6835; A61K 49/0034; A61K 49/0093; C08F 138/02; C08F 2/58; C12N 15/1136; C23C 16/509; C23C 16/26
See application file for complete search history.

(56) References Cited

U.S. PATENT DOCUMENTS

2016/0222143 A1 8/2016 Goyanes et al.

FOREIGN PATENT DOCUMENTS

EP 2985043 A1 2/2016

OTHER PUBLICATIONS

Vasilev, Plasma Chem Plasma Process (2014) 34:545-558. (Year: 2014).*
Bachhuka et al. (2015) "Hybrid core/shell microparticles and their use for understanding biological processes," Journal of Colloid and Interface Science, vol. 457, pp. 9-17.
Cao et al. (2004) "Synthesis of hollow nanoparticles by plasma polymerization," Journal of Nanoparticle Research, vol. 6, pp. 447-455.
Goktas (2009) "Characerization of plasma-polymerized thiophene thin films and nanoparticles synthesized by a double-discharge technique," Plasma Processes and Polymers, vol. 6, pp. 126-131.
Guo et al. (2008) "In vivo imaging and drug storage by quantum-dot conjugated carbon nanotubes," Adv. Funct. Mater., vol. 18, pp. 2849-2497.
International Search Report for International Application No. PCT/AU2017/051437, dated Feb. 28, 2018.
International Preliminary Report on Patentability for International Application No. PCT/AU2017/051437, dated Apr. 9, 2019.
Korner et al. (2012) "Tailor-made silver release properties of silver-containing functional plasma polymer coatings adjusted through a macroscopic kinetics approach," Plasma Chem Plasma Process, vol. 32, pp. 619-627.
Kovacevic et al. (2009) "Formation and material analysis of plasma polymerized carbon nitride nanoparticles," Journal of Applied Physics, vol. 105, pp. 104910-1 to 104910-8.
Majeski et al. (2012) "Photoresponse of PbS nanoparticles-quaterthiophene films prepared by gaseous deposition as probed by XPS," J. Vac. Sci. Technol. A: Vaccum, Surfaces and Films, vol. 30(4):04D109-1 to 04D109-5.
Yang et al. (2009) "Synthesis of intrinsic flourescent polypyrrole nanoparticles by atmospheric pressure plasma polymerization," Applied Surface Science, vol. 255, pp. 6924-6929.
O. Kylian et al. (2013) "Nanostructured plasma polymers", Elsevier, Thin Solid Films; vol. 548; pp. 1-17.
E. Kovacevic, et al. (2012) "Size dependent characteristics of plasma synthesized carbonaceous nanoparticles", Journal of Applied Physics; vol. 112; pp. 013303-1-013303-5.
E. Kovacevic, et al. (2011) "Tailored modification of plasma polymerized nanoparticles", AIP Conference Proceedings; pp. 443-444; doi: 10.1063/1.3659884.
Suk-Ho Hong, et al. (2006) "Size dependence of optical properties and internal structure of plasma grown carbonaceous nanoparticles studied by in situ Rayleigh-Mie scattering ellipsometry", Journal of Applied Physics; vol. 100; pp. 064303-1-064303-14.

(Continued)

*Primary Examiner* — Robert S Cabral
(74) *Attorney, Agent, or Firm* — Brian C. Trinque; Lathrop GPM LLP

(57) ABSTRACT

This application relates to nanoparticles, including nanoparticles derived from a plasma, and their use in the formation of conjugates. The nanoparticles can be stably conjugated to a wide variety of second species, forming conjugates which can be used, for example, in therapeutic, diagnostic and experimental methods.

15 Claims, 66 Drawing Sheets

(56) References Cited

OTHER PUBLICATIONS

B. Banik, et al. "Polymeric nanoparticles: the future of nanomedicine"; WIREs Nanomed Nanobiotechnol 2016, 8:271-299, doi: 10.1002/wnan.1364.

M. Santos, et al. (2018) "Plasma Synthesis of Carbon-Based Nanocarriers for Linker-Free Immobiliation of Bioactive Cargo", ACS Appl. Nano. Mater.; vol. 1; pp. 580-594.

Muhammad Ajmal, et al. (2015) "Synthesis, characterization and in vitro evaluation of methotrexate conjugated fluorescent carbon nanoparticles as drug delivery system for human lung cancer targeting", Journal of Photochemistry & Photobiology B: Biology, 153 pp. 111-120, journal homepage: www/elsevier.com/locate/jpb.

* cited by examiner

A)

B)

A)

B)

D)

| Sample Descriptions | Zeta Potential (MV) | STDV |
|---|---|---|
| nanoP³ | 43.5 | 0.757 |
| nanoP³ + Paclitaxel | 11.6 | 2.06 |
| nanoP³ + Paclitaxel + IgG-Cy5 | 13.6 | 0.529 |
| nanoP³ + Paclitaxel + IgG-Cy5 + IgG-Cy7 | 18.9 | 0.872 |
| IgG-Cy5 | -32.7 | 5.39 |
| IgG-Cy7 | -17.6 | 0.945 |
| Paclitaxel | -34.2 | 2.02 | a b

Scale bar = 2um, 5000x magnification

Scale bar = 500nm, 30000x magnification

PLASMA-DERIVED NANOPARTICLES

CROSS-REFERENCE TO RELATED APPLICATIONS

The present application is a 35 U.S.C. § 371 nationalization of PCT application PCT/AU2017/051437 filed Dec. 21, 2017, which claims priority from Australian Provisional Patent Application No 2016905306 filed on 21 Dec. 2016, each of which is incorporated herein by reference in its entirety.

TECHNICAL FIELD

This application relates to nanoparticles, including nanoparticles derived from a plasma, and their use in the formation of conjugates.

BACKGROUND

Multifunctional nanocarriers, capable of delivering multiple molecular cargos within the same structure, are expected to greatly improve both therapeutic and diagnostic outcomes in numerous diseases. However, current nanoparticle-based therapeutics and diagnostics still utilise materials that are not inherently bioactive and arguably do not allow a direct and simple conjugation with pharmaceutical agents. The functionalisation of nanoparticles (e.g., gold, iron-oxide, polymeric, quantum dots, etc.), is typically complex and generally relies on time-consuming, and multi-step protocols to achieve a robust conjugation between the nanocarrier surface and the associated cargo.

Despite the recent rapid growth of nanomedicine research, there is a need for new nanofabrication strategies which can deliver novel products with improved performance, functionality and safety for patients. For instance, in the field of drug delivery in humans, current commercially approved pharmaceutical nanocarriers are based on the concept of passive targeting. In passive targeting, the carriers rely on their small size to penetrate the abnormal leaky vasculature of pathological sites, such as tumours or inflammation areas. Although these nanoparticle-drug systems sometimes enhance the efficacy of treatments, when compared to other therapeutic alternatives, deficiencies remain in drug biodistribution and site accumulation. The promise of reduced drug side-effects and increasing dose tolerances has not been realised. In this regard, there has been considerable effort to develop a nanocarrier platform that can potentially provide an active targeted and selective delivery with increased dose tolerance.

In order to achieve specific and targeted delivery in a wide range of therapeutic applications, nanoparticles can be functionalised with different target ligands which recognise and bind to specific surface signatures expressed on target cells. The complexity of the different signalling pathways in multifactorial diseases, such as cancer, has led the way for the development of multi-drug inhibitor based therapies that can circumvent treatment resistance. Importantly, the efficacy of multi-drug approaches is enhanced when different drugs are combined within or on the same nanocarrier. Furthermore, it is also desirable to attain superior control and monitoring over the nanoparticle system during therapy by means of medical imaging, meaning that it would be advantageous for nanoparticles to also incorporate appropriate imaging agents. Thus, there is a strong demand for developing multifunctional nanoparticles with the ability to achieve a tailored mix of different functionalities, integrating both targeted therapy, diagnostics and imaging within the same nanostructure. However, the capacity to bind multiple molecular cargos on the same nanocarrier is particularly elusive in the field.

Additionally, there is significant scope for therapeutic delivery of nucleic acids including DNA, mRNA, and siRNA to regulate aberrant protein expression in disease. This approach has shown great promise in vitro, but has not translated well clinically, i.e., for in vivo procedures. Amongst several drawbacks, when administered systemically, these molecules are: highly unstable in blood; filtered out by the kidneys and liver; and their highly-charged states prevent ready transport across cell membranes. Furthermore, once across a cell membrane, mRNA and siRNA need to escape the endosome to reach the cytoplasm for activity, while DNA needs to enter the nucleus. Nanoparticle platforms, including liposomal nanoparticles have been used to facilitate delivery with intermediate success, which is nevertheless hampered by issues with toxicity and long-term persistence in cells. A nanoparticle platform with the capacity to carry this type of cargo across the cell membrane, preferentially to the cytoplasm or nucleus in a targeted manner, would represent a significant advance for the field.

A nanoparticle with a surface capable of providing robust chemical conjugation sites would be a major breakthrough in the field. In current platforms, one of the limitations to combining multiple functions on a nanoparticle, in a single construct, is the actual surface chemistry of the nanoparticle. To achieve superior control over different functionalities of the nanocarrier, attachment through chemical bonds is preferable over weaker, non-covalent strategies. In order to overcome this difficulty, a common strategy adopted by many commercial platforms is to graft the nanoparticles with polymers, such as poly(ethylene glycol) (PEG). However, these coating and functionalisation strategies involve multi-step, time-consuming and complex protocols that often involve solvents that present safety or disposal difficulties. Moreover, the optimisation, reproducibility and control over the surface concentration and thickness of the PEG are typically difficult to achieve with these conjugation processes. Typically, the terminal groups of the coating ligands also limit the range of biomolecules that can be immobilised. Other conjugation strategies involve the pre-conjugation of molecules with the nanoparticle material in self-assembly processes. However, these latter approaches also rely on the usage of organic solvents and multiple purification steps that compromise the native conformation and functionality of the molecular cargos. The use of multiple synthetic steps may also decrease the final yield of functionalised nanoparticles.

There is therefore a need for an improved process for producing nanoparticles activated for conjugation with therapeutic and/or imaging moieties. Ideally the activated nanoparticles should be capable of being functionalised with multiple functional molecules using simple approaches such as direct incubation with solutions comprising biomolecules.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

In a first aspect, disclosed herein is a nanoparticulate polymer characterised by one or more of the following features:

a broad electron paramagnetic resonance peak centred in a range of about 3470 G to about 3520 G, and/or corresponding to a g-factor in a range of about 2.001 to about 2.005;

a spin density measured by electron paramagnetic resonance within about 0 hours to about 2 hours post synthesis in the range of about $10^{19}$ to about $10^{15}$ spins/cm$^3$.

a spin density in the range of about $10^{17}$-about $10^{15}$ spins/cm$^3$ measured by electron paramagnetic resonance within about 0 hours to about 240 hours post synthesis.

one or more absorbance bands in an infrared spectrum centred:
in a range of about 3680-about 2700 cm$^{-1}$;
in a range of about 1800-about 1200 cm$^{-1}$;
in a range of about 2330-about 2020 cm$^{-1}$;
in a range of about 1200-about 1010 cm$^{-1}$; and/or
in a range of about 1010-about 700 cm$^{-1}$;

one or more absorbance bands in an infrared spectrum centred:
in a range of about 3600-3100 cm$^{-1}$; and/or
in a range of about 3100-2700 cm$^{-1}$;

a zeta potential in a range of from about −100 mV to about +100 mV;

a zeta potential in a range of from about −80 mV to about +80 mV measured in a solution within a pH range from about 2 to about 10; or a nitrogen:carbon elemental ratio of about 0.01:1 to about 2:3.

In a second aspect, disclosed herein is an aggregate comprising two or more nanoparticulate polymers of the first aspect.

In a third aspect, disclosed herein is a conjugate comprising:
a nanoparticulate polymer of the first aspect, or an aggregate of the second aspect; and
at least one second species.

In a fourth aspect, disclosed herein is a pharmaceutical composition, the pharmaceutical composition comprising a nanoparticulate polymer of the first aspect, an aggregate of the second aspect, or a conjugate of the third aspect, and a pharmaceutically acceptable carrier, excipient, or binder.

In a fifth aspect, disclosed herein is a substrate comprising a nanoparticulate polymer of the first aspect, an aggregate of the second aspect, or a conjugate of the third aspect.

In a sixth aspect, disclosed herein is use of:
a nanoparticulate polymer of the first aspect;
an aggregate of the second aspect; or
a mixture thereof,
in the formation of a conjugate.

In a seventh aspect, disclosed herein is a method for preparing a nanoparticulate polymer or an aggregate, the method comprising:
i) providing at least one gas in a reaction chamber;
ii) supplying power to a first electrode so as to generate a plasma in the reaction chamber;
iii) applying a voltage to a second electrode in said reaction chamber; and
iv) collecting the resulting nanoparticulate polymer or aggregate;
wherein the at least one gas comprises an organic gas.

In an eighth aspect, disclosed herein is a method for preparing a nanoparticulate polymer or an aggregate, the method comprising:
i) providing at least one gas in a reaction chamber;
ii) supplying radio frequency (rf) power to a first electrode in said reaction chamber so as to generate a capacitively coupled plasma in the reaction chamber;
iii) applying a voltage to a second electrode in said reaction chamber; and
iv) collecting the resulting nanoparticulate polymer or an aggregate,
wherein the at least one gas comprises an organic gas.

In a ninth aspect, disclosed herein is a method for preparing a nanoparticulate polymer or an aggregate, the method comprising:
i) providing at least one gas in a reaction chamber;
ii) supplying radio frequency (rf) power so as to generate an inductively coupled plasma in the reaction chamber;
iii) applying a voltage to a second electrode in said reaction chamber; and
iv) collecting the resulting nanoP$^3$ material,
wherein the at least one gas comprises an organic gas.

In tenth aspect, disclosed herein is a nanoparticulate polymer or an aggregate produced by a method according to the eighth or ninth aspect.

In an eleventh aspect, disclosed herein is a method of forming a conjugate, the method comprising:
providing:
i) a nanoparticulate polymer of the first aspect, an aggregate of the second aspect, or a nanoparticulate polymer or aggregate of the tenth aspect; and
ii) at least one second species; and
contacting the nanoparticulate polymer or aggregate and the at least one second species such that the nanoparticulate polymer or aggregate and the at least one second species become physically or chemically associated with one another.

In a twelfth aspect, disclosed herein is a conjugate produced by the method of the eleventh aspect.

In a thirteenth aspect, disclosed herein is a method of treating a subject suffering from, susceptible to, or displaying one or more symptoms of a disease, disorder, or condition, the method comprising a step of administering the nanoparticulate polymer of the first aspect; the aggregate of the second aspect; the conjugate of the third aspect or twelfth aspect; the pharmaceutical composition of the fourth aspect; or the nanoparticulate polymer or aggregate of the tenth aspect, to the subject.

In a fourteenth aspect, disclosed herein is use of a nanoparticulate polymer of the first aspect; an aggregate of the second aspect; a conjugate of the third aspect or twelfth aspect; or a nanoparticulate polymer or aggregate of the tenth aspect, in the formation of a medicament for treating a disease, disorder, or condition in a subject.

In a fifteenth aspect, disclosed herein is a method of imaging a region within a subject, the method comprising a step of administering the conjugate of the third aspect or twelfth aspect, or the pharmaceutical composition of the fourth aspect, to the subject wherein at least one second species is an imaging agent.

In a sixteenth aspect, disclosed herein is the nanoparticulate polymer of the first aspect, the aggregate of the second aspect, the conjugate of the third aspect or twelfth aspect, the pharmaceutical composition of the fourth aspect, or the nanoparticulate polymer or aggregate of the tenth aspect, for use in treating a disease, disorder, or condition in a subject In a seventeenth aspect, disclosed herein is a method of stabilising an agent, the method comprising conjugating the agent to a nanoparticulate polymer of the first aspect, an aggregate of the second aspect, a conjugate of the third aspect or twelfth aspect, or a nanoparticulate polymer or aggregate of the tenth aspect. The agent may be the same as the second species as described herein.

It will be appreciated that the embodiments of each aspect of the present disclosure may equally be applied to each other aspect, mutatis mutandis.

BRIEF DESCRIPTION OF DRAWINGS

Whilst it will be appreciated that a variety of embodiments of the invention may be utilised, in the following, we describe a number of examples of the invention with reference to the following drawings.

DETAILED DESCRIPTION

Figure 1:
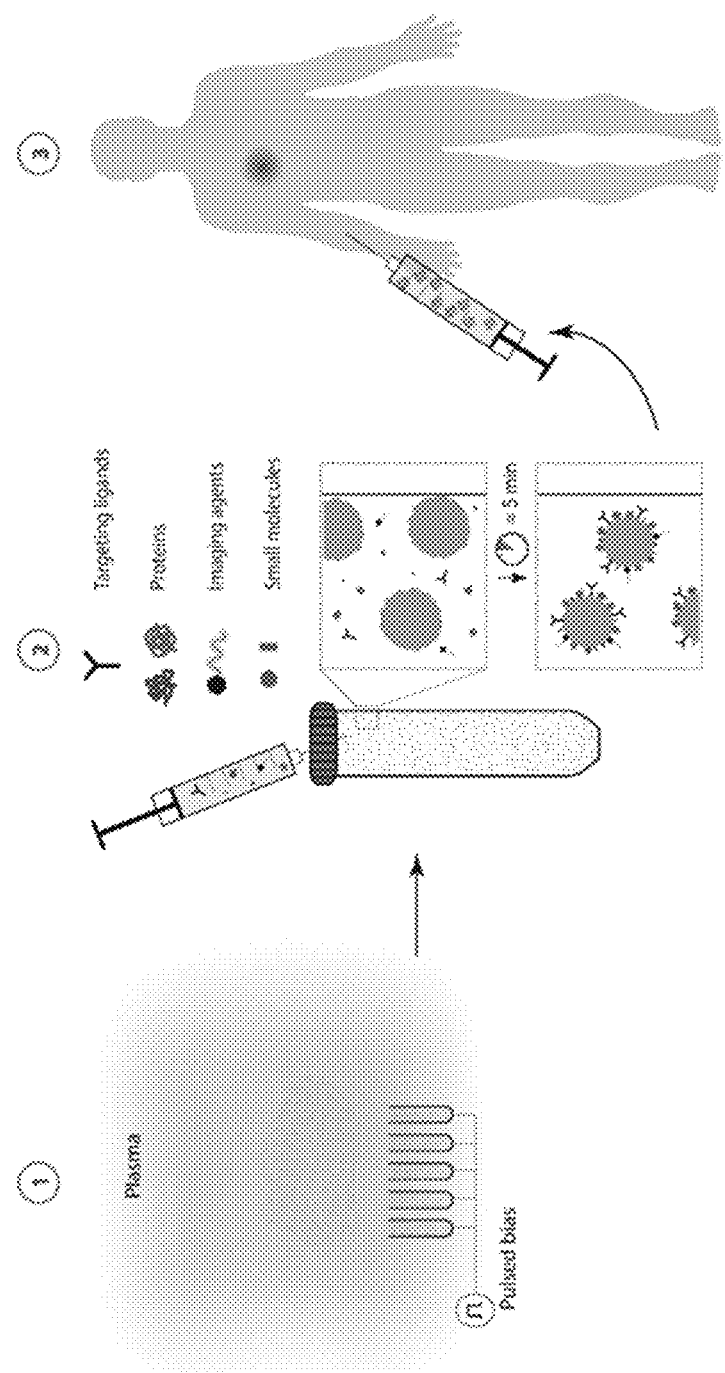
FIG. 1—Scaled production of nanoP$^3$ particles and its use as a therapeutic and diagnostic agent for clinical use.

The Inventors have demonstrated the production of nanoparticulate materials, described herein as "nanoP$^3$", "NanoP$^3$", "nanoP$^3$ material" or "NanoP$^3$ material". These nanoP$^3$ materials can act as a class of versatile and multifunctional nanocarriers which may be readily functionalised. The nanoP$^3$ material can be bound to a large range of biomolecules and drugs through reaction with radicals embedded within the nanoP$^3$ material which diffuse to the surface of the nanoP$^3$ material and/or by reaction with moieties/functional groups formed on the surface of the nanoP$^3$ material, or conjugates thereof.

One key advantage of the nanoP$^3$ materials described herein is that they can retain radicals embedded in them for an extended period of time. Over time these radicals diffuse to the surface and react with proximate species. When the materials are stored in appropriate conditions (for example: under inert atmospheres; by sealing vials containing the materials inside a plasma chamber, under vacuum conditions immediately after collection; and/or at lower temperatures), the radicals may be retained for weeks, months or potentially years. The extended lifetime of the radicals means that the nanoP$^3$ material could be stored until such time that a conjugate is required for a particular diagnostic test or method of treatment. This means that production of the nanoP$^3$ material does not need to occur at the same time a conjugate is required for a particular application or treatment regime.

Advantageously, conjugates between the nanoP$^3$ and one or more second species, for example a pharmaceutical drug, imaging agent and/or peptide, can be made in a one-pot reaction. It is thought that radicals are formed and preserved in the nanostructure during a rapid growth phase where smaller carbon-based clusters (nanoparticulate polymers) created in an active plasma-gas phase are combined to form aggregates. The nanoP$^3$ can maintain the bioactivity of immobilised biomolecules on its surface and may be readily internalised by different cell types without inducing cytotoxicity.

Conversely, when conjugated with nanoP$^3$, cytotoxic drugs such as doxorubicin are capable of killing cancer cells. Additionally, nanoP$^3$ is able to deliver silencing RNA inside cells, resulting in a significant knockdown in protein expression 48 hours after cellular uptake. Furthermore, the covalent binding ability of nanoP$^3$ and the bioactivity of the immobilised biomolecule are maintained for at least several months after freeze-dried storage.

The processes disclosed herein, for example the described plasma-based processes, can be used to effectively fabricate and collect nanoparticles with advantageous and tunable physical, chemical and morphological properties that are capable of integrating multiple functionalities for a variety of nanomedicine applications.

Definitions

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, the term "consisting essentially of" is intended to exclude elements which would materially affect the properties of the claimed composition, although may include elements that do not materially affect properties.

With regards to the definitions provided herein, unless stated otherwise, or implicit from context, the defined terms and phrases include the provided meanings. Unless explicitly stated otherwise, or apparent from context, the terms and phrases below do not exclude the meaning that the term or phrase has acquired by a person skilled in the relevant art. The definitions are provided to aid in describing particular embodiments, and are not intended to limit the claimed invention, because the scope of the invention is limited only by the claims. Furthermore, unless otherwise required by context, singular terms shall include pluralities and plural terms shall include the singular.

Throughout the present specification, various aspects and components of the invention can be presented in a range format. The range format is included for convenience and should not be interpreted as an inflexible limitation on the scope of the invention. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 3, from 1 to 4, from 1 to 5, from 2 to 4, from 2 to 5, from 3 to 5 etc., as well as individual and partial numbers within the recited range, for example, 1, 2, 3, 4, 5, 5.5 and 6, unless where integers are required or implicit from context. This applies regardless of the breadth of the disclosed range. Where specific values are required, these will be indicated in the specification.

"About"

Herein the term "about" encompasses a 10% tolerance in any value(s) connected to the term.

"Hydrocarbon"

Hydrocarbon monomers disclosed herein are understood to be monomers consisting of hydrogen and carbon atoms only. Examples of hydrocarbons include: alkenes, alkynes, clycloalkenes, aromatic compounds, or mixtures thereof "Aggregate"

As used herein, the term "aggregate" shall mean a particle comprising a plurality of nanoparticulate polymers and having a size in a range of 5 nm to 100 µm, for example a size in a range of about 5 nm to about 500 nm, unless otherwise specified or clear from the context in which it is used.

"Conjugate"

Herein the term "conjugate" refers to molecules formed by the attachment of one or more compounds to a nanoparticulate polymer or an aggregate comprising nanoparticulate polymers. The "one or more compounds" may be a second species as defined herein. The attachment may be via a covalent bond or an electrostatic interaction.

"Monomer"

The term "monomer" unless stated otherwise will be understood to mean a monomeric compound that can be reacted to form a polymer by means of one or more reactive functional groups that may be created by fragmentation and reaction processes in a plasma.

"NanoP$^3$"

The term "nanoP$^3$" refers to a nanoparticulate material having a size less than 100 micron unless otherwise specified or clear from the context in which it is used, for example the nanoP$^3$ may have a size of between about 5 and 500 nm. Unless stated or implicit from context, the term "nanoP$^3$" encompasses both "nanoparticulate polymers" and "aggregates" as defined herein unless otherwise specified or clear from the context in which is used. The term "nanoP$^3$" may be used interchangeably with "nanoparticulate material". In one preferred embodiment the nanoparticulate material comprises a plasma polymer. The plasma polymer may be formed by the condensation of fragments in a plasma, said material being capable of covalently coupling one or more compounds, for example one or more "second species", including organic or organometallic species.

"Nanoparticulate Polymer"

Herein the term "nanoparticulate polymer" refers to polymers formed with monomers defined herein, wherein the nanoparticulate polymer has a particle size in the range of about 1 nm to about 50 nm. In one preferred embodiment the a nanoparticulate polymer is formed by the condensation of fragments in a plasma, said material being capable of covalently coupling one or more compounds including organic or organometallic species.

"Polymer"

The term "polymer" refers to a chemical compound or mixture of compounds consisting of repeating structural units that may be heterogeneous and/or arranged into a disordered structure, created through a process of polymerisation. Suitable polymers useful in this invention are described throughout. In one embodiment the polymer is a plasma polymer in which the repeating units are assembled into a relatively disordered structure.

"Plasma"

The term "plasma" generally refers to a (partially) ionized gas-like mass comprising a mixture of ions, electrons, neutral species and radiation. The plasmas referred to herein comprise at least one monomer.

"Plasma Polymer"

Herein a "plasma polymer" is a polymer derived from a plasma comprising one or more monomers.

Monomers

The nanoP$^3$ materials described herein are derived from one or more monomers.

In one embodiment the one or more monomers are used in a gaseous form for forming the nanoP$^3$ material.

A monomer may be a hydrocarbon. Examples of hydrocarbons include alkenes, alkynes, cycloalkenes and cycloalkynes.

Examples of suitable alkene monomers include, but are not limited to: ethylene, propene, 1-butene, 1-pentene, 1-hexene, 1-heptene, 1-octene, 1-nonene, 1-decene, isomers thereof, or a mixture thereof.

Examples of suitable alkyne monomers include, but are not limited to: ethyne (acetylene), propyne, 1-butyne, 1-pentyne, 1-hexyne, 1-heptyne, 1-octyne, 1-nonyne 1-decyn, isomers thereof, or a mixture thereof.

Examples of suitable cycloalkene monomers include, but are not limited to: cyclopropene, cyclobutene, cyclopentene, cyclohexene, cycloheptene, cyclooctene, 1,3-cyclohexadiene, 1,4-cyclohexadiene, 1,5-cyclooctadiene, isomers thereof, or a mixture thereof.

Examples of suitable cycloalkyne monomers include, but are not limited to: cycloheptyne, cyclooctyne, cyclononyne, isomers thereof, or a mixture thereof.

In one embodiment an alkene is used as a monomer. The alkene may be the only monomer utilised in the formation of nanoparticulate polymer, or it may be used in the presence of at least one other monomer to form a copolymer, for example another alkene and/or an alkyne, cycloalkene or cycloalkyne.

In one embodiment an alkyne is used as a monomer. The alkyne may be the only monomer utilised in the formation of nanoparticulate polymer, or it may be used in the presence of at least one other monomer to form a copolymer, for example another alkyne and/or an alkene, cycloalkene or cycloalkyne. In a further embodiment acetylene is used as a monomer, either on its own or in the presence of at least one other monomer.

In another embodiment acetylene is used as a monomer in combination with at least one other monomer, for example at least one other monomer which is an alkene, alkyne, cycloalkenes or cycloalkyne.

In one embodiment a cycloalkene is used as a monomer. The cycloalkene may be the only monomer utilised in the formation of nanoparticulate polymer, or it may be used in the presence of at least one other monomer to form a copolymer, for example another cycloalkene and/or an alkene, alkyne or cycloalkyne.

In one embodiment a cycloalkyne is used as a monomer. The cycloalkyne may be the only monomer utilised in the formation of nanoparticulate polymer, or it may be used in the presence of at least one other monomer to form a copolymer, for example another cycloalkyne and/or an alkene, alkyne or cycloalkene.

Other monomers that may be used for forming the nanoP$^3$ include perfluorocarbons, ethers, esters, amines, alcohols or carboxylic acids.

Examples of suitable perfluorocarbons include, but are not limited to: perfluoroallyl benzene.

Examples of suitable ethers include, but are not limited to: diethylene glycol vinyl ether, diethylene glycol divinyl ether, diethylene glycol monoallyl ether, or a mixture thereof.

Examples of suitable amines include, but are not limited to: allylamine, cyclopropylamine, poly (vinyl amine), or a mixture thereof.

Examples of suitable alcohols include, but are not limited to: poly (vinyl alcohol), allyl alcohol, ethanol, or a mixture thereof.

Examples of suitable carboxylic acids include, but are not limited to acrylic acid.

NanoP$^3$

The nanoP$^3$ material may be a homopolymer or a copolymer. In one embodiment the nanoP$^3$ material is a homopolymer. In another embodiment the nanoP$^3$ material is a copolymer.

In one embodiment the nanoP$^3$ is derived from a plasma comprising one or more monomers as described herein, which are initially present in a gaseous form. One or more inert gases, for example helium, neon or argon may optionally be present with the one or more monomers.

Nanoparticulate polymers may be formed in the presence of a gas from group 15, 16 or 17 of the periodic table, such as nitrogen. Fragments of this gas may be imported into the nanoparticulate polymer. For example, the presence of nitrogen may result in the presence of amine, imine or nitrile groups, or a mixture thereof in a nanoparticulate polymer or nanoP$^3$ material. Thus, the nanoparticulate polymer disclosed herein may comprise nitrogen.

Nitrogen has been found to be suitable not only as a carrier but also as a reactive non-polymerisable gas. This means that nitrogen may also be incorporated in the nanoparticulate material, imparting particular physical-chemical properties to the resulting functionalised nanoparticulate material. Furthermore, nitrogen is also thought to enable different modes of nanoparticle formation that otherwise would not be possible if nitrogen was not used. It is expected that the inclusion of other gases, such as those in the same group of nitrogen, will also provide an extra degree of freedom in modulating nanoparticle formation mechanisms and physical-chemical properties.

In one embodiment the nanoP$^3$ material is derived from a plasma comprising at least one monomer as described herein. Optionally the nanoP$^3$ material is formed in the presence of a gas, for example nitrogen, wherein fragments of the gas are incorporated into the nanoparticulate polymer.

The nanoP$^3$ material may have a nitrogen:carbon elemental ratio of about 0.01:1 to about 2:3. For example the nanoparticulate polymer may have a nitrogen:carbon elemental ratio of about 0.05 to about 1, or about 0.1 to about 1, or about 0.15 to about 1, or about 0.2 to about 1, or about 0.25 to about 1, or about 0.3 to about 1, or about 0.35 to about 1, or about 0.4 to about 1, or about 0.45 to about 1, or about 0.5 to about 1, or about 0.55 to about 1, or about 0.6 to about 1, or about 0.65 to about 1. Alternatively, the nanoparticulate polymer may have a nitrogen:carbon elemental ratio of about 0.1 to about 1:2.

The nanoP$^3$ materials described herein preferably comprise at least one binding site capable of binding one or more compounds, for example an organic or an organometallic compound, or a second species as defined herein.

In one embodiment the nanoP$^3$ material described herein comprises at least binding site capable of binding one or more compounds, wherein the binding site comprises unpaired electrons which are capable of binding an organic or an organometallic compound, or a second species as defined herein The nanoP$^3$ material may comprise unpaired electrons in the polymer. These unpaired electrons may be on or near the surface of the nanoparticles. The unpaired electrons may be at a depth of 40 nm or less within particles of the nanoparticulate material, or within about 30, 20 or 10 nm of the surface, or may be between about 10 and about 40 nm from the surface or between about 10 and 30, 20 and 40 or 20 and 30 nm from the surface, or about 1, 2, 3, 4, 5, 10, 15, 20, 25, 30, 35 or 40 nm from the surface. They may be at a variety of depths from about 0 to about 40 nm. In some instances they may be at depths of greater than 40 nm. They may be throughout the volume of the nanoparticulate material. This may render the material capable of reacting with a second species, such as an organic or organometallic species, so as to covalently couple said species to the nanoparticulate polymer and form a conjugate.

In an embodiment there is provided a nanoP$^3$ material, particles thereof having a mean diameter of about 5 nm to about 500 nm, said nanoP$^3$ material comprising an organic plasma polymer and said nanoP$^3$ (nanoparticulate polymer or aggregate thereof) comprising unpaired electrons, thereby being capable of covalently couple with an organic or organometallic species.

In another embodiment the nanoparticulate material or nanoP$^3$ material comprises at least one functional moiety which is capable of chemically or physically coupling a second species.

The nanoP$^3$ material may have a mean diameter of about 1 nm to less than about 1000 nm. For example, the nanoP$^3$ material may have a mean diameter of from about 5 nm to about 500 nm, or about 5 to 500, 50 to 500, 100 to 500, 200 to 500, 5 to 200, 5 to 100, 5 to 50, 5 to 20, 20 to 100, 100 to 300 or 200 to 400 nm, e.g., about 5, 10, 20, 30, 40, 50, 100, 150, 200, 250, 300, 350, 400, 450 or 500 nm, or in a range of about 5 to about 400 nm, or about 5 to about 300 nm, or about 5 to about 200 nm, or about 5 to about 100 nm, or about 100 to about 500 nm, or about 100 to about 400 nm, or about 100 to about 300 nm, or about 100 to about 200 nm, or about 200 to about 400 nm, or about 200 nm to about 300 nm, or a mixture thereof.

The size of the nanoP$^3$ material may be measured by scanning electron microscopy, transmission electron microscopy, low angle laser light scattering, photon correlation spectroscopy, differential mobility analysis, or some other suitable technique. The particles of the nanoP³ material may have a narrow size distribution or a broad size distribution. The standard deviation of the particle size distribution may be between about 1% and about 500% of the mean particle size, or between about 1 and 200, 1 and 100, 1 and 50, 1 and 20, 1 and 10, 1 and 5, 1 and 2, 10 and 500, 20 and 500, 50 and 500, 100 and 500, 200 and 500, 10 and 100, 10 and 50 or 50 and 100%, e.g., about 1, 2, 3, 4, 5, 10, 20, 30, 40, 50, 60, 70, 80, 90, 100, 150, 200, 250, 300, 350, 400, 450 or 500%. In some instances they may be approximately monodispersed, i.e., all particles may be approximately the same size (e.g., within about 10%, or about 5%, or about 2% of the same diameter).

The nanoP³ material may comprise an organic plasma polymer. Plasma polymers are characterised by a heterogeneous, dense, highly crosslinked network. They may be amorphous. This plasma polymer may be generated by the reaction (e.g., ionisation and fragmentation), of active species generated in the plasma from the organic gas and other reactive gases in a gas mixture or by reactive species in the plasma/gas mixture resulting from the ionization and fragmentation of gases in the gas mixture.

The nanoP³ materials may be characterised via a number of methods including, but not limited to: electron paramagnetic resonance (EPR) spectroscopy, infrared spectroscopy (such as Fourier transform infrared spectroscopy), Raman spectroscopy, UV-VIS spectroscopy, elemental analysis (e.g., X-ray photoelectron spectroscopy), soft X-ray spectroscopy, determination of a zeta potential, nuclear magnetic resonance (NMR) spectroscopy, mass spectrometry, gel permeation chromatography, scanning electron microscopy (SEM), transmission electron microscopy (TEM), low angle laser light scattering, photon correlation spectroscopy, differential mobility analysis, elastic recoil detection analysis (ERDA), or neutron scattering.

The nanoP³ material (for example the nanoparticulate polymer or aggregates), may be characterised by one or more of the following features:
  a broad electron paramagnetic resonance peak centred in a range of about 3470 G to about 3520 G, and/or corresponding to a g-factor in a range of about 2.001 to about 2.005;
  a spin density measured by electron paramagnetic resonance within about 0 hours to about 2 hours post-synthesis in the range of about $10^{19}$ to about $10^{15}$ spins/cm³.
  a spin density in the range of about $10^{17}$ to about $10^{15}$ spins/cm³ measured by electron paramagnetic resonance within about 0 hours to about 240 hours post synthesis.
  one or more absorbance bands in an infrared spectrum centred:
    in a range of about 3680-about 2700 cm⁻¹;
    in a range of about 1800-about 1200 cm⁻¹;
    in a range of about 2330-about 2020 cm⁻¹;
    in a range of about 1200-about 1010 cm⁻¹; and/or
    in a range of about 1010-about 700 cm⁻¹;
  one or more absorbance bands in an infrared spectrum centred:
    in a range of about 3600-3100 cm⁻¹; and/or
    in a range of about 3100-2700 cm⁻¹;
  a zeta potential in a range of from about −100 mV to about +100 mV;
  a zeta potential in a range of from about −80 mV to about +80 mV measured in a solution within a pH range of about 2 to about 10; or
  a nitrogen:carbon elemental ratio of about 0.1:1 to about 2:3.

In one embodiment, the nanoP³ material, nanoparticulate polymer or aggregate is characterised using EPR spectroscopy. The nanoparticulate polymer or aggregate may show a broad electron paramagnetic resonance peak centred in a range of about 3470 G to about 3520 G, and/or corresponding to a g-factor in a range of about 2.001 to about 2.005.

In one embodiment the nanoP³ material, nanoparticulate polymer or aggregate has a spin density measured by EPR spectroscopy within about 0 hours to about 2 hours post-synthesis in the range of about $10^{19}$ to about $10^{15}$ spins/cm³. The measurement may be made: about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, or about 120 minutes, post-synthesis.

In one embodiment the nanoP³ material, nanoparticulate polymer or aggregate has a spin density in the range of about $10^{17}$ to about $10^{15}$ spins/cm³ measured by electron paramagnetic resonance within about 0 hours to about 240 hours post-synthesis. The measurement may be made: about 0.5, about 1, about 2, about 4, about 5, about 6, about 8, about 10, about 20, about 30, about 40, about 50, about 60, about 70, about 80, about 90, about 100, about 110, about 120, about 130, about 140, about 150 hours, about 160, about 170, about 180, about 190, about 200, about 210, about 220, about 230, or about 240 hours, post-synthesis.

In another embodiment, the nanoP³ material, nanoparticulate polymer or aggregate is characterised using infrared spectroscopy (such as Fourier transform infrared spectroscopy). For example, the nanoparticulate polymer or aggregate may show one or more absorbance bands in an infrared spectrum centred:
  in a range of about 3680-about 2700 cm⁻¹;
  in a range of about 1800-about 1200 cm⁻¹;
  in a range of about 2330-about 2020 cm⁻¹;
  in a range of about 1200-about 1010 cm⁻¹;
  in a range of about 1010-about 700 cm⁻¹;
  in a range of about 3600-3100 cm⁻¹;
  in a range of about 3100-2700 cm⁻¹; and/or
  a mixture thereof.

In another embodiment, the nanoP³ material, nanoparticulate polymer or aggregate is characterised using the zeta potential of the nanoparticulate polymer or aggregate. For example, the nanoP³ material, nanoparticulate polymer or aggregate may possess a zeta potential in a range from about −100 mV to about +100 mV. For example the zeta potential may be in a range from about −50 mV to about 60 mV.

In a further embodiment, the nanoP³ material, nanoparticulate polymer or aggregate has a zeta potential in a range of from about −80 mV to about +80 mV, when measured in a solution within a pH range of about 2 to about 10.

The nanoP³ material may have rough cauliflower like surface morphology. This may be due to their formation by aggregation of the nanoparticulate polymers. Thus the nanoP³ material may be aggregates of the nanoparticulate polymers. The nanoP³ material and aggregates may be spherical, or generally spherical. The nanoparticulate polymers may have a diameter of about 1 to about 50 nm, or about 5 to 10, 5 to 10, 10 to 50, 20 to 50 or 10 to 30 nm, e.g., about 5, 10, 15, 20, 25, 30, 35, 40, 45 or 50 nm. Aggregates (and the associated nanoparticulate polymers) may have embedded highly reactive radicals that diminish in quantity over time. The nanoP$^3$ material may also have embedded long-lived and stable radicals in delocalised orbitals of carbon clusters.

The stable radicals (secondary radicals) may result from reactions involving highly reactive radicals (primary radicals). The nanoP$^3$ material may have a surface that is hydrophilic. The surface may therefore allow ready dispersion of the nanoP$^3$ material in water. It may allow retention of bioactivity of surface immobilised bioactive molecules. The hydrophilic surface may be a result of oxidation of radicals during formation or after formation by exposure of the surface to air. Following conjugation with one or more second species, the nanoP$^3$ material conjugate may be hydrophilic or hydrophobic. Alternatively, the nanoP$^3$ material conjugate may display amphiphilic properties.

Depending on the monomers used or the conditions applied during the polymerisation, the nanoP$^3$ material may be crosslinked. The term "crosslinked" herein refers to a polymer composition containing intramolecular and/or intermolecular bonds. These crosslinking bonds may be covalent or non-covalent in nature. Non-covalent bonding includes hydrogen bonding, electrostatic bonding, and ionic bonding.

One potential advantage obtained from crosslinking is the stability of the resulting nanoP$^3$ material and potentially a conjugate formed from such a material. For example, crosslinking can reduce the solubility of the nanoP$^3$ material (or a resulting conjugate) in comparison to similar compositions which are not crosslinked. In addition, the crosslinked nature of the nanoP$^3$ material (or a conjugate formed thereof), may increase the chemical resistance of the nanoparticulate material or resulting conjugate.

The nanoP$^3$ may be doped with additional inorganic elements or compounds, or organometallic compounds, which act as image enhancing contrast agents in medical imaging techniques. The nanoP$^3$ may be doped with magnetic resonance imaging (MRI) contrast agents such as iron oxide or gadolinium compounds. Examples of imaging enhancing contrast agents include: fluorescent dyes (e.g., Alexa 680, indocyanine green, and Cy5.5); isotopes and radionuclides, such as: $^{11}$C, $^{13}$N, $^{15}$O, $^{18}$F, $^{32}$P, $^{51}$Mn, $^{52m}$Mn, $^{52}$Fe, $^{55}$Co, $^{62}$Cu, $^{64}$Cu, $^{67}$Cu, $^{67}$Ga, $^{68}$Ga, $^{72}$As, $^{73}$Se, $^{75}$Br, $^{76}$Br, $^{82m}$Rb, $^{83}$Sr, $^{86}$Y, $^{90}$Y, $^{89}$Zr, $^{94m}$Tc, $^{94}$Tc, $^{99m}$Tc, $^{110}$In, $^{111}$In, $^{120}$I, $^{123}$I, $^{124}$I, $^{125}$I, $^{131}$I, $^{154}$Gd, $^{155}$Gd, $^{156}$Gd, $^{157}$Gd, $^{158}$Gd, $^{177}$Lu, $^{186}$Re, $^{188}$Re, and $^{223}$Ra; paramagnetic ions, such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III); metals, such as lanthanum (III), gold (III), lead (II), and bismuth (III); oxides of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III); metals, such as lanthanum (III), gold (III), lead (II), and bismuth (III), including iron oxide and gadolinium oxide; ultrasound-contrast enhancing agents, such as liposomes; and radiopaque agents, such as barium, gallium, and thallium compounds. The imaging enhancing contrast agents may be may be incorporated directly onto the nanoP$^3$ material, or indirectly by using an intermediary functional group, such as chelators.

Aggregates

Aggregates may be formed from the nanoparticulate polymers described herein during the production of the nanoP$^3$ material.

In one embodiment the aggregate has a size in the range of about 5 nm to about 100 µm, for example about 5 nm to about 500 nm.

Conjugates

The nanoparticulate polymers, aggregates or nanoP$^3$ materials described herein may be bound to one or more compounds, for example an organic compound, an organometallic compound, or a second species as defined herein, in order to form a conjugate. When the second species carries a surface charge, the binding of a charged second species to nanoP$^3$ may be modulated by changing the pH of the reaction conditions during the conjugation process. The pH of the solution modulates the charge of nanoP$^3$ through protonation or de-protonation of surface functional groups, such as amines and carboxylic acid groups. For example, the binding of positively-charged conjugates to nanoP$^3$ materials may be improved by increasing the pH of the solution containing the nanoP$^3$ materials and the second species. At highly alkaline media, nanoP3 becomes becomes negatively charged via deprotonation carboxylic surface groups, which also stabilizes the nanoparticles due to the repulsion of between negatively charged particles. Alternatively, the binding of negatively-charged conjugates to nanoP$^3$ materials may be improved by decreasing the pH of the solution containing the nanoP$^3$ materials and the second species. As demonstrated herein, many second species can be conjugated to the nanoP$^3$ materials described herein without changing the pH of the reaction conditions, irrespective of any surface charge on the second species.

Disclosed herein in the use of a nanoP$^3$ material (for example: a nanoparticle polymer, an aggregate, or a mixture thereof), in the formation of a conjugate.

The conjugate may comprise only a single second species. Alternatively the conjugate may comprise two or more different second species, for example two, three or four second species.

The nanoP$^3$ materials are generally capable of directly coupling, for example by covalent coupling or ionic coupling, to a second species, such as an organic or an organometallic species. When the nanoparticle polymer or aggregate is a plasma polymer, the coupling process is generally rapid and capable of proceeding under mild conditions. The coupling may be by means of unpaired electrons in the polymer structure (i.e., radical sites) or by means of functional groups generated on the nanoP$^3$ material, or incorporated onto the resulting conjugate via the addition of an appropriate second species or by reaction with air (or another gas), or some other fluid to which the nanoP$^3$ material is exposed. The nanoP$^3$ material may include monomer units which comprise functional moieties which are capable of chemically coupling a second species. The conjugation of one or more second species with the nanoP$^3$ material may introduce functional groups on or in the resulting conjugate, which can be used for further chemical reactions or used as binding sites for processes such as biochemical/biological processes taking place in in vitro or in vivo conditions.

Herein, functional moieties (or "functional groups"), refers to a group of atoms present on the monomer, nanoP$^3$ material, or conjugate comprising a nanoP$^3$ material, which can react with other complimentary functional groups, for example other functional groups present on a second species. Functional groups include but are not limited to the following moieties: carboxylic acid (—(C=O)OH), carbonyl, primary or secondary amine (—NH$_2$, —NH—), nitric oxide, maleimide, thiol (—SH), sulfonic acid (—(O=S=O)OH), carbonate, carbamate (—O(C=O)N<), hydroxy (—OH), aldehyde (—(C=O)H), ketone (—(C=O)—), hydrazine (>N—N<), isocyanate, isothiocyanate, phosphoric acid (—O(P=O)OHOH), phosphonic acid (—O(P=O)OHH), haloacetyl, alkyl halide, acryloyl, aryl fluoride, hydroxylamine, disulfide, vinyl sulfone, vinyl ketone, diazoalkane, oxirane, and aziridine, or a mixture thereof.

Herein a "second species" is a compound that can be physically adsorbed on or chemically bound to a nanoP$^3$ material (i.e., a nanoparticulate polymer or aggregate thereof), to form a conjugate.

The second species may be selected from the group consisting of: imaging reagents, biomolecules, drugs, enzymes, antibodies, targeting ligands, polynucleotides, siRNA, RNA, RNA constructs, DNA, DNA constructs, vectors, plasmids, carbohydrates, catalysts and mixtures thereof. Additionally, species such as whole cells, cell fragments, micelles, liposomes, hydrogels, proteins (electrospun proteins such as silk) and polymer, semiconductor, ceramic or metallic particles may be covalently attached to the nanoP$^3$ material in this manner. In one example, the second species is a fluorescent dye. For example, the fluorescent dye may be indocyanine green (sodium 4-[2-[(1E,3E,5E,7Z)-7-[1,1-dimethyl-3-(4-sulfonatobutyl)benzo[e]indol-2ylidene]hepta-1,3,5-trienyl]-1,1-dimethylbenzo[e]indol-3-ium-3-yl]butane-1-sulfonate; CAS number 3599-32-4).

The terms "antibody" or "antibodies" as used herein shall be taken to encompass a protein that comprises a variable region made up of one or more immunoglobulin chains, e.g., a polypeptide comprising a $V_L$ and a polypeptide comprising a $V_H$. An antibody also may comprise constant domains, some of which can be arranged into a constant region or constant fragment or fragment crystallizable (Fc). A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. The antibodies can be of any type (e.g., IgG, IgE, IgM, IgD, IgA, and IgY), class (e.g., IgG$_1$, IgG$_2$, IgG$_3$, IgG$_4$, IgA$_1$ and IgA$_2$) or subclass. The term "antibody" also encompasses humanized antibodies, de-immunized antibodies, non-depleting antibodies, non-activating antibodies, primatized antibodies, human antibodies and chimeric antibodies. As used herein, the term "antibody" is also intended to include formats other than full-length, intact or whole antibody molecules, such as Fab, F(ab')2, and Fv which are capable of binding to an epitopic determinant. These formats may be referred to as antibody "fragments". These antibody formats retain some ability to selectively bind to a target protein, examples of which include, but are not limited to, the following:

(1) Fab, the fragment which contains a monovalent binding fragment of an antibody molecule and which can be produced by digestion of whole antibody with the enzyme papain to yield an intact light chain and a portion of one heavy chain;

(2) Fab', the fragment of an antibody molecule which can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab)2 is a dimer of two Fab' fragments held together by two disulfide bonds;

(4) Fv, defined as a genetically engineered fragment containing the variable region of the light chain and the variable region of the heavy chain expressed as two chains;

(5) Single chain antibody ("SCA"), defined as a genetically engineered molecule containing the variable region of the light chain, the variable region of the heavy chain, linked by a suitable polypeptide linker as a genetically fused single chain molecule; such single chain antibodies may be in the form of multimers such as diabodies, triabodies, and tetrabodies etc. which may or may not be polyspecific; and (6) Single domain antibody, typically a variable heavy domain devoid of a light chain.

Accordingly, an antibody as described herein may include separate heavy chains, light chains, Fab, Fab', F(ab')2, Fc, a variable light domain devoid of any heavy chain, a variable heavy domain devoid of a light chain and Fv. Such fragments can be produced by recombinant DNA techniques, or by enzymatic or chemical separation of intact immunoglobulins. Any of the antibodies or fragments thereof described herein and otherwise known in the art can be conjugated to the nanoP$^3$ particles disclosed herein.

The second species may be a polynucleotide. The term "polynucleotide" as used herein shall be taken to encompass DNA, RNA, an antisense polynucleotide, a ribozyme, an interfering RNA, a siRNA, a microRNA, and any other polynucleotide known in the art. The polynucleotide may encode a protein or a functional RNA (such as an interfering RNA). Thus, the polynucleotide may be a polynucleotide vector or plasmid. Accordingly, the nanoP$^3$ material disclosed herein may be used to transport a polynucleotide to a target site of interest in a subject, which polynucleotide exerts a functional effect itself or provides for the expression of a protein or functional RNA that then has a functional effect in a cell of the subject.

Examples of second species include: a targeting ligand, a pharmaceutical drug, an imaging agent, an amino acid, a peptide, a synthetic analogue of a natural bioactive molecule, a synthetic peptide mimetic, a protein (such as an enzyme or antibody), a receptor-targeting ligand, a gene targeting agent, a polynucleotide, an RNA, a photosensitive dye, a cleavable linking molecule such as a pH-sensitive linker, a hydrocarbon, a whole cell, a cell fragment, a micelle, a liposome, a hydrogel, a polymer particle, semiconductor particle, ceramic particle, metal particle, a growth factor, a cytokine, an antithrombotic and/or fibrinolytic agent, or a mixture thereof.

For example, an antibody may be attached to the nanoP$^3$ material in order to target the nanoparticles to a particular cell type, and a therapeutic molecule may be attached to the same nanoparticle polymer in order to deliver a therapeutic effect to those cells. An imaging molecule may additionally or alternatively be attached to the nanoP$^3$ material in order to enable imaging of the cell type.

The nanoP$^3$ of the present invention not only allow immobilisation of a broad range of molecules but the attached species maintain their functionality and activity after immobilisation. The Inventors have demonstrated this feature with more than one type of biomolecule attached to the nanoP$^3$ material at the same time.

The nanoP$^3$ material (the nanoparticulate polymer and/or aggregates thereof) may be capable of reacting with more than one type of second species. Different types of molecules and permutations within those different molecules may be reacted and immobilised at the same time or sequentially in or on the nanoP$^3$ material. The coupled species may maintain their uncoupled activity, e.g., bioactivity and functionality, after immobilisation on the nanoP³ material and the resulting conjugate.

Examples of second species that may be bound to the nanoP³ material are shown on pages 1262 to 1739 of Remington: The Science and Practice of Pharmacy, 21$^{st}$ Edition; Lippincott Williams & Wilkins: Philadelphia, Pa., 2005, the content of which is incorporated by reference.

Examples of second species include, but are not limited to: diagnostic drugs and reagents; topical drugs; gastrointestinal and liver drugs; blood, fluids, electrolytes, and haematological drugs; cardiovascular drugs; respiratory drugs; sympathomimetic drugs; cholinomimetic drugs; adrenergic antagonists and adrenergic; neuron blocking drugs; anti-muscarinic and antispasmodic drugs; skeletal muscle relaxants; diuretic drugs; uterine and anti-migraine drugs; hormones and hormone antagonists; general anaesthetics; local anaesthetics; antianxiety agents and hypnotic drugs; antiepileptic drugs; psychopharmacologic agents; analgesic, antipyretic, and anti-inflammatory drugs; histamine and antihistaminic drugs; central nervous system stimulants; antineoplastic drugs; immunoactive drugs; parasiticides; immunising agents and allergenic extracts; anti-infectives; enzymes; nutrients and associated substances, or a mixture thereof.

Herein the term "targeting ligand" refers to a molecule that binds to or interacts with a target molecule. Typically the nature of the interaction or binding is non-covalent, e.g., by hydrogen, electrostatic, or van der Waals interactions, however, binding may also be covalent.

The term "ligand", as used herein, refers to compounds which target biological markers. Examples of ligands include, but are not limited to: proteins, peptides, antibodies, antibody fragments, saccharides, carbohydrates, glycans, cytokines, chemokines, nucleotides, lectins, lipids, receptors, steroids, neurotransmitters, Cluster Designation/Differentiation (CD) markers, imprinted polymers, and the like.

Examples of targeting ligands include, but are not limited to: a nuclear localisation signal (for example KR[PAATK-KAGQA]KKKK), RGD, NGR, Folate, Transferrin, GM-CSF, galactosamine, anti-VEGFR, anti-ERBB2, anti-CD20, anti-CD22, anti-CD19, anti-CD33, anti-CD25, anti-tenascin, anti-CEA, anti-MUC1, anti-TAG72, anti-HLA-DR10, or a mixture thereof.

Examples of pharmaceutical drugs include, but are not limited to: anticancer drugs (such as: doxorubicin, paclitaxel, vincristine, cyclophosphamide and topotecan); asthma drugs (e.g., Fluticasone and salmeterol—which includes steroid and bronchodilators); anti-HIV retrovirals (e.g., abacavir (Ziagen), efavirenz/emtriacitabine/tenofovir disoproxil fumarate (Atripla), lamivudine/zidovudine (Combivir), emtriacitabine/rilpivirine/tenofovir disoproxil fumarate (Complera), emtricitabine (Emtriva), lamivudine (Epivir), abacavir/lamivudine (Epzicom), zidovudine (Retrovir)); agents modulating cell replication/proliferation: target of rapamycin (TOR) inhibitors (including sirolimus, everolimus and ABT-578); paclitaxel and antineoplastic agents (including alkylating agents, e.g., cyclophosphamide, mechlorethamine, chlorambucil, melphalan, carmustine, lomustine, ifosfamide, procarbazine, dacarbazine, temozolomide, altretamine, cisplatin, carboplatin and oxaliplatin); antitumor antibiotics (bleomycin, actinomycin D, mithramycin, mitomycin C, etoposide, teniposide, amsacrine, topotecan, irinotecan, doxorubicin, daunorubicin, idarubicin, epirubicin, mitoxantrone and mitoxantrone); antimetabolites (including: deoxycoformycin, 6-mercaptopurine, 6-thioguanine, azathioprine, 2-chlorodeoxyadenosine, hydroxyurea, methotrexate, 5-fluorouracil, capecitabine, cytosine arabinoside, azacytidine, gemcitabine, fludarabine phosphate and aspariginase); antimitotic agents (including: vincristine, vinblastine, vinorelbine, docetaxel, estramustine); molecularly targeted agents (including: imatinib, tretinoin, bexarotene, bevacizumab, gemtuzumab ogomicin and denileukin diftitox); anti-inflammatory drugs; corticosteroids; estrogens; androgens; progestogens and adrenal androgens; antibiotics, analgesics; opoids, or a mixture thereof.

Examples of imaging agents include, but are not limited to: luciferase; fluorescently labelled dyes and antibodies, contrast agents (including: iopamidol, iohexol and ioxilan); barium sulfate; MRI contrast agents (for example: gadolinium, iron oxide and manganese based imaging agents); Indocyanine green (ICG), and mixture thereof.

As used herein, the term "peptide" is intended to mean any polymer comprising amino acids linked by peptide bonds. The term "peptide" is intended to include polymers that are assembled using a ribosome as well as polymers that are assembled by enzymes (i.e., non-ribosomal peptides) and polymers that are assembled synthetically. In various embodiments, the term "peptide" may be considered synonymous with "protein," or "polypeptide". In various embodiments, the term "peptide" may be limited to a polymer of greater than 50 amino acids, or alternatively, 50 or fewer amino acids. In various embodiments, the term "peptide" is intended to include only amino acids as monomeric units for the polymer, while in various embodiments, the term "peptide" includes additional components and/or modifications to the amino acid backbone. For example, in various embodiments, the term "peptide" may be applied to a core polymer of amino acids as well as derivatives of the core polymer, such as core polymers with pendant polyethylene glycol groups or core polymers with amide groups at the amino or carboxy terminus of the amino acid chain.

Examples of amino acids include, but are not limited to: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

Examples of peptides include, but are not limited to: polypeptides comprising: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids selected from: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

A "peptide mimetic" can be a molecule such as a peptide, a modified peptide or any other molecule that biologically mimics active ligands of hormones, cytokines, enzyme substrates, viruses or other bio-molecules. This peptide mimetic may antagonise, stimulate, or otherwise modulate the physiological activity of the natural ligands. Peptides that have a length of 14 to 20 amino acids can serve as lead compounds for the development of therapeutically effective agents. Since they are usually considerably smaller than the parent molecule, chances are high that they may show fewer side effects and are easier to deliver to the target. The major emphasis for synthesising a peptide mimetic is to mimic a peptide or protein ligand of receptors. However the technology is useful for enzyme inhibition as well. Since the term "peptide mimetic" is relatively broad, natural compounds such as natural occurring opiate alkaloids are examples of peptidomimetics as well. Indeed, small peptides, as well as opioids, can sometimes target the same receptor.

Here the term "protein" refers to a sequence of amino acids for which the chain length is sufficient to produce the higher levels of tertiary and/or quaternary structure. The protein may have a molecular weight in a range of about 300 Da to about 150 kDa. The protein may have a molecular weight of greater than 150 kDa, or a molecular weight less than 300 Da.

Examples of proteins encompassed within the definition herein include mammalian proteins, such as, e.g., growth hormone, including human growth hormone and bovine growth hormone; growth hormone releasing factor; parathyroid hormone; a ribosome inactivating protein such as saporin; thyroid stimulating hormone; lipoproteins; α-1-antitrypsin; insulin A-chain; insulin B-chain; proinsulin; follicle stimulating hormone; calcitonin; luteinizing hormone; glucagon; clotting factors such as factor VIIIC, factor, tissue factor, and von Willebrands factor; anti-clotting factors such as Protein C; atrial natriuretic factor; lung surfactant; a plasminogen activator, such as urokinase or tissue-type plasminogen activator (t-PA); bombazine; thrombin; tumour necrosis factor-α and -β; enkephalinase; RANTES (regulated on activation normally T-cell expressed and secreted); human macrophage inflammatory protein (MIP-1-α); serum albumin such as human serum albumin; mullerian-inhibiting substance; relaxin A-chain; relaxin B-chain; prorelaxin; mouse gonadotropin-associated peptide; DNase; inhibin; activin; vascular endothelial growth factor (VEGF); receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I); insulin-like growth factor binding proteins; CD proteins such as CD3, CD4, CD8, CD19 and CD20; erythropoietin (EPO); thrombopoietin (TPO); osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies; and biologically active fragments or variants of any of the above-listed polypeptides.

Examples of gene targeting agents include, but are not limited to: DNA (gDNA, cDNA), RNA (sense RNAs, antisense RNAs, mRNAs, tRNAs, rRNAs, small interfering RNAs (siRNAs), short hairpin RNAs (ShRNAs), micro RNAs (miRNAs), small nucleolar RNAs (SnoRNAs, small nuclear (snRNAs)) ribozymes, aptamers, DNAzymes, antisense oliogonucleotides, vectors, plasmids, other ribonuclease-type complexes, and mixtures thereof.

Examples of photosensitive dyes include, but are not limited to: indocyanine green (ICG).

Examples of a cleavable linking molecule such as a pH-sensitive linker, may be found in Leriche et al., "Cleavable linkers in chemical biology" *Bioorganic & Medicinal Chemistry*, 20, 571-582, 2012, the contents of which are included by reference. Exemplary groups of linkers and compounds include, but are not limited to: pH cleavable, photocleavable (for example cleavable via laser or infrared light), laser cleavable, heat cleavable, and protease cleavable (including via the action of blood proteases like kallekrein and thrombin) linkers and compounds.

Examples of cells include, but are not limited to: progenitor cells (including: endothelial progenitor cells, CD34+, CD133+, KDR+ or VCAM-1+ monocytes, hemopoietic stem cells, mesenchymal stem cells, embryonic stem cells), differentiated cells (including endothelial cells, fibroblasts and smooth muscle cells), or a mixture thereof.

Examples of hydrogels include, but are not limited to: include covalent or sonically crosslinked polysaccharide-based hydrogels such as the polyvalent metal salts of alginate, pectin, carboxymethyl cellulose, heparin, hyaluronate and hydrogels from chitin, chitosan, pullulan, gellan, xanthan and hydroxypropylmethylcellulose.

Examples of polymer, semiconductor, ceramic or metal particles include, but are not limited to: semiconducting quantum dots, fluorescent nanoparticles, gold nanoparticles, silver nanoparticles, iron oxide, other magnetic particles, or a mixture thereof.

Examples of growth factors include, but are not limited to: vascular endothelial growth factor, fibroblast growth factor, hepatocyte growth factor, connective tissue growth factor, placenta-derived growth factor, angiopoietin-1 and granulocyte-macrophage colony-stimulating factor.

Examples of cytokines include, but are not limited to: interleukins such as interleukin-1, interleukin-4, interleukin-10; GM-CSF; TNF-α; interferon-gamma; TGF-β; or a mixture thereof.

Examples of antithrombotic and fibrinolytic agents include, but are not limited to: glycoprotein IIb/IIIa inhibitors, direct thrombin inhibitors, heparins, low molecular weight heparins, platelet adenosine diphosphate (ADP) receptor inhibitors, fibrinolytic agents (including streptokinase, urokinase, recombinant tissue plasminogen activator, reteplase and tenecteplase), enzymes (including: streptokinase, urokinase, tissue plasminogen activator (tPA), and plasmin), or a mixture thereof.

In one embodiment the conjugate comprises only one second species.

In another embodiment the conjugate comprises two second species.

In another embodiment the conjugate comprises three second species.

In another embodiment the conjugate comprises more than two second species.

The second species may be physically or chemically bound directly to the nanoP$^3$ material, or the second species may be attached via a linking moiety. The second species may be modified to comprise this linking moiety. The linking molecule may degrade in vitro or in vivo due to changes in environmental variables such as pH, heat or light in order to release the second species. Alternatively the linker may be cleavable by enzymes that occur naturally in cells. For example a cleavable linking molecule, such as a pH degradable linker, may release a second species which is a drug molecule in vivo.

The size of the conjugates may allow for passive targeting of tumour cells or tumour tissue via the enhanced permeability and retention (EPR) effect. Through this EPR effect, conjugates may passively accumulate in solid tumours as a consequence of the disorganised pathology of angiogenic tumour vasculature with its discontinuous endothelium, leading to hyperpermeability to large macromolecules, and the lack of effective tumour lymphatic drainage.

Pharmaceutical Compositions

Disclosed herein are pharmaceutical compositions comprising a nanoparticulate polymer, aggregate, or a conjugate as defined herein, and a pharmaceutically acceptable carrier, excipient, or binder. In one embodiment, the nanoparticulate polymer, aggregate or conjugate is pharmaceutically acceptable. In the pharmaceutical compositions disclosed herein, the second species may be a therapeutic or a diagnostic agent.

As used herein, "pharmaceutically acceptable carrier, excipient or binder" includes excipients or agents such as solvents, diluents, dispersion media, coatings, antibacterial and antifungal agents, isotonic and absorption delaying agents and the like that are physiologically compatible and are not deleterious to a compound as described herein or use thereof. The use of such carriers and agents to prepare compositions of pharmaceutically active substances is well known in the art (see, for example Remington: The Science and Practice of Pharmacy, 21$^{st}$ Edition; Lippincott Williams & Wilkins: Philadelphia, Pa., 2005).

The pharmaceutically acceptable composition may be diluted prior to use. Suitable diluents may be selected from, for example: Ringer's solution, Hartmann's solution, dextrose solution, saline solution and sterile water for injection.

The term "composition" as used herein is intended to encompass a product comprising the specified ingredients in the specified amounts, as well as any product which results, directly or indirectly, from combination of the specified ingredients in the specified amounts.

Herein, "pharmaceutically acceptable" means that the nanoP$^3$ material (i.e., the nanoparticulate polymers or aggregates), or a conjugate thereof, along with carriers, diluents or excipients, must be compatible with the other ingredients of the pharmaceutical composition, and not deleterious to the recipient thereof. The nanoP$^3$ material (i.e., the nanoparticulate polymers or aggregates), or a conjugate thereof, should be able to contact tissues of a recipient without excessive toxicity, irritation, allergic response or other potential complications commensurate with a reasonable benefit/risk ratio identified by a skilled medical professional or veterinarian. In addition the nanoparticulate polymers, aggregates or conjugates, should be compatible with a carrier and/or excipient in any composition that is to be delivered as a medicament to an individual, for example to an animal or human being.

It will be appreciated that in some cases the nanoparticulate polymers, aggregates or conjugates are non-pharmaceutically acceptable and these fall within the scope of the present invention. However, in order for use in pharmaceutical formulations, in some embodiments the nanoP$^3$ material (i.e., the nanoparticulate polymers or aggregates) or a conjugate thereof, are pharmaceutically acceptable compounds. Non-pharmaceutically acceptable nanoP$^3$ material (i.e., the nanoparticulate polymers or aggregates) or a conjugate thereof, may be useful in the preparation of pharmaceutically acceptable nanoP$^3$ material (i.e., the nanoparticulate polymers or aggregates) or a conjugate thereof.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavours, etc.), according to techniques such as those well known in the art of pharmaceutical formulation.

The nanoP$^3$ material (i.e., the nanoparticulate polymers or aggregates) or a conjugate thereof, defined herein may be administered by any suitable means, for example, parenterally, such as by subcutaneous, intraperitoneal, intravenous, intramuscular, or intracisternal injection or infusion techniques (e.g., as sterile injectable aqueous or non-aqueous solutions or suspensions).

Pharmaceutical formulations include those for oral, rectal, nasal, topical (including buccal and sub-lingual), parenteral administration (including intramuscular, intraperitoneal, sub-cutaneous and intravenous), or in a form suitable for administration by inhalation or insufflation. The nanoP$^3$ material (i.e., the nanoparticulate polymers or aggregates) or a conjugate thereof, together with a conventional adjuvant, carrier or diluent, may thus be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, or in the form of sterile injectable solutions for parenteral (including subcutaneous) use.

In one embodiment the conjugates may be designed for slow release applications. For example, the conjugate may comprise a second species (such as a pharmaceutical drug or diagnostic agent), which is attached to the nanoparticulate polymer or aggregate by way of a degradable linker. The linking molecule may degrade in vitro or in vivo due to changes in environmental variables such as pH or heat in order to release the second species. For example, the degradable linker may be photosensitive and allow the release of a second species (such as a drug, siRNA, or RNA) upon light of an appropriate wavelength, for example via infra-red or laser irradiation. Alternatively the linker may be cleavable by enzymes that occur naturally in cells. The degradation of the linker may result in a steady or constant release of a pharmaceutical drug, to allow: for an extended and/or relatively constant treatment of a condition; or a diagnostic agent to be tracked in vitro or in vivo within a subject.

Alternatively a second species incorporated into a conjugate may be a prodrug which is: directly attached to the nanoparticulate polymer or aggregate; or attached to the nanoparticulate polymer or aggregate by way of a degradable linker. Herein a prodrug is an inactive form of a compound bound to a nanoparticulate polymer or aggregate (with or without the use of a linker), in a conjugate. Once administered to a subject, the inactive form can be metabolised in to a pharmaceutically active form either whilst the prodrug is still attached to the nanoparticulate polymer or aggregate, or once it has been released from the nanoparticulate polymer or aggregate.

Alternatively, the nanoparticulate polymers, aggregates or conjugates thereof, may be incorporated into a material which is used topically. For example the nanoparticulate polymers, aggregates or conjugates may be incorporated into a bandage.

The nanoparticulate polymers, aggregates or conjugates thereof could be incorporated into an appropriate scaffold for the cutaneous treatment of cuts/wounds or conditions such as psiorase, or eczema.

The nanoparticulate polymers, aggregates of conjugates thereof, may be used on or in implants, such as cardiac patches, vascular grafts, implants to promote healing of bone and other tissue defects.

The pharmaceutical compositions for the administration of the compounds of this invention may conveniently be presented in dosage unit form and may be prepared by any of the methods well known in the art of pharmacy. All methods include the step of bringing the active ingredient, for example a conjugate as defined herein, into association with the carrier which constitutes one or more accessory ingredients. In general, the pharmaceutical compositions are prepared by uniformly and intimately bringing the active ingredient, for example a conjugate, into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable formulations.

The pharmaceutical compositions and methods disclosed herein may further comprise other therapeutically active compounds which are usually applied in the treatment of the disclosed disorders or conditions. Selection of the appropriate agents for use in combination therapy may be made by one of ordinary skill in the art, according to conventional pharmaceutical principles. The combination of therapeutic agents may act synergistically to effect the treatment or prevention of the various disorders or conditions disclosed herein. Using this approach, one may be able to achieve therapeutic efficacy with lower dosages of each agent, thus reducing the potential for adverse side effects.

When other therapeutic agents are employed in combination with nanoparticulate polymers, aggregates or conjugates thereof, they may be used for example in amounts as noted in the Physician Desk Reference (PDR) or as otherwise determined by one of ordinary skill in the art.

It will be understood, however, that the specific dose level and frequency of dosage for any particular patient may be varied and will depend upon a variety of factors including the activity of the specific compound employed, the metabolic stability and length of action of that compound, the age, body weight, general health, gender, diet, mode and time of administration, rate of excretion, drug combination, the severity of the particular condition, and the host undergoing therapy.

Methods of Treatment

Disclosed herein is a method of treating a subject suffering from, susceptible to, or displaying one or more symptoms of a disease, disorder, or condition, the method comprising a step of administering a nanoparticulate polymer, aggregate or conjugate thereof, as defined herein, or a pharmaceutical composition as defined herein, to the subject. The term "treating" is used herein to encompass both therapeutic and prophylactic treatment. Thus, the methods of treatment disclosed herein may encompass methods of preventing one or more symptoms of a disease, disorder, or condition. It will be appreciated that "treating" may be interpreted as effecting a reduction in any one or more symptoms of a disease, disorder, or condition. Also disclosed herein is use of a nanoparticulate polymer, aggregate or conjugate as defined herein, in the manufacture of a medicament for treating or preventing a condition in a subject.

Furthermore, also disclosed herein is a method of imaging a region within a subject, the method comprising a step of administering to the subject: a nanoparticulate polymer; an aggregate; a conjugate; or a pharmaceutical composition, as defined herein, wherein at least one second species is an imaging agent. For example the conjugate or pharmaceutical composition may comprise a contrast agent which may be detected by a diagnostic technique such as, but not limited to: magnetic resonance imaging (MRI), X-ray, ultrasound, positron emission tomography (PET) or photoacoustic imaging.

In one embodiment a nanoparticulate polymer, aggregate or a conjugate as defined herein is used as a medicament or utilised in the formation of a medicament.

Nanoparticulate polymers, aggregates or conjugates, may be provided in an "effective amount", for example when an appropriate compound is added to a pharmaceutical composition. The phrase "effective amount" is taken to mean an amount of the nanoparticulate polymer, aggregate or conjugate that will elicit a desired biological or medical response of a tissue, system, animal or human that is being sought by the researcher, veterinarian, medical doctor or other clinician administering the compound of a composition comprising the compound.

The "effective amount" will be dependent on a number of factors, including the efficacy of the particular nanoparticulate polymer, aggregate or conjugate. The subject's weight and age may also be a factor for the person skilled in the art when determining the concentration of compound that the subject should receive.

The phrases "administration of" and or "administering a" compound should be understood to mean providing a nanoparticulate, aggregate or conjugate, or a pharmaceutical composition comprising a nanoparticulate, aggregate or conjugate as defined herein, to a subject in need of treatment.

The recipients of a nanoparticulate, aggregate or conjugate; or a pharmaceutical composition comprising a nanoparticulate, aggregate or conjugate, can be human beings, male or female.

Alternatively the recipients of: a nanoparticulate, aggregate or conjugate; or a pharmaceutical composition comprising a nanoparticulate, aggregate or conjugate, can also be a non-human animal. "Non-human animals" or "non-human animal" is directed to the kingdom Animalia, excluding humans, and includes both vertebrates and invertebrates, male or female, and comprises: warm blooded animals, including mammals (comprising but not limited to primates, dogs, cats, cattle, pigs, sheep, goats, rats, guinea pigs, horses, or other bovine, ovine, equine, canine, feline, rodent or murine species), birds, insects, reptiles, fish and amphibians.

The recipients of the compounds and pharmaceutically acceptable compositions are referred herein with the interchangeable terms "patient", "recipient" "individual", and "subject". These four terms are used interchangeably and refer to any human or animal (unless indicated otherwise), as defined herein.

Diseases, disorders or conditions that could be treated using the nanoP$^3$ or a conjugate thereof, include but are not limited to: acute coronary syndrome, an aging-related disease or disorder; an allergic disease or a related condition; Alzheimer's disease, siRNA delivery, asthma, HIV, antibiotic resistance, atherosclerosis, an autoimmune disease; a bacterial infection, cancer; dementia, depression or a related condition; diabetes; dyslipidemia, hyperlipidemia, hypertension, ichthyosis, an immune disease; a metabolic disease or disorder; a neurological disease or disorder; obesity; Parkinson's disease; pain, rheumatoid arthritis, or a proliferative disease including cancer. Types of cancer include: anal cancer, asbestos & lung disease (mesothelioma), bile duct cancer, bladder cancer, bone cancer (sarcoma), bowel cancer (colorectal), brain & spinal cord tumours, breast cancer, carcinoid tumours (neuroendocrine), cervical cancer, endocrine cancer (thyroid), eye cancer, gall bladder cancer, head & neck cancers (mouth, nose & throat), Kaposi's sarcoma, kidney cancer, leukaemia, liver cancer, lung cancer, lymphoma (non-Hodgkin & Hodgkin), melanoma, multiple myeloma, oesophagus cancer, ovarian cancer, pancreatic cancer, penis cancer, peritoneal cancer, peritoneal mesothelioma, pleural mesothelioma, prostate cancer, skin cancers (non-melanoma), soft tissue cancers, spinal tumours, stomach & oesophageal cancer, testicular cancer, thyroid cancer, thymus cancer, uterus cancer (endometrial cancer) and vulvar and vaginal cancers.

The nanoparticulate polymers, aggregates or conjugates described herein may be used in diagnostic tests. For example the conjugate could comprise probe sequences of ssDNA or other hybridisable molecules, antibodies, fluorescent agents, magnetic particle, enzyme or other detectable markers which could participate in a detection step of a particular diagnostic test, thereby identifying the presence of the hybridisation partner.

The plasma technology described herein allows for the production and collection of nanoP$^3$ in a well-controllable manner for subsequent clinical use as a therapeutic/diagnostic agent or functionalisation agent, or non-clinical use (for example: as a research tool for the delivery of genetic materials; nanoP$^3$ functionalised with enzymes could also be used in fluidised bed type flow through reactors for food or chemical processing; imaging of cell compartments, combining primary and secondary antibodies for increasing histology throughput, cell/drug tracking in animal models, amongst other applications). Established process parameter windows define nanoparticle yield, size, surface morphology and chemistry. Nanoparticles are produced in an active plasma-gas phase allowing direct collection into sterile clinical vials (FIG. 1). Plasma treatment is a widely used method for sterilization and thus, the plasma discharge can play a dual role of nanoparticulate polymer and aggregate formation and sterilization of the particle containing vials. The resulting vials containing nanoP$^3$ can then be accessible in the clinic in an off the shelf manner. The concentration of the nanoP$^3$ in each vial can be consistent and readily controlled by the plasma deposition parameters. In a simple one-step process, clinicians can readily prepare tailor-made therapies and/or diagnostics according to the patient condition. The concentration of nanoP$^3$ in each vial can also be selected to optimise binding to and delivery of the appropriate second species.

Substrates

Disclosed herein is a substrate comprising a nanoparticulate polymer, an aggregate, or a conjugate, as defined herein.

The substrate may be formed from a material selected from, but not limited to: glass, polymers, metals, and composites. The substrate may be derived from natural or synthetic materials.

The substrate may comprise biodegradable materials.

The nanoparticulate polymer, aggregate or conjugate may be incorporated into the substrate during the formation of the substrate. For example, a composition comprising a polymer formation (such as polyurethane) or a protein (such as silk) and a conjugate may be utilised in the formation of a substrate in the form of a scaffold, by way of electrospinning.

The nanoparticulate polymers, aggregates or conjugates may be incorporated in or on the substrate during the formation of the substrate, or in a post-modification process after the substrate has been formed.

Conjugates as defined herein may be incorporated on a substrate or hydrogel (for example at a wound site, or tissue/bone defect). The conjugates may form covalent bonds with the substrate, negating any need for modification of the substrate.

The substrate may be non-degradable or biodegradable. When the scaffold is substrate, second species attached to the conjugate may undergo slow release, allowing for the controlled delivery of one or more second species.

The nanoparticulate polymers, aggregates or conjugates may be physically entrapped within the substrate, or chemically bound to the substrate. For example chemical moieties on the surface of the nanoparticulate polymers, aggregates or conjugates may combine with complementary moieties present on the substrate (for examples: alcohols, amines, carboxylic acid and/or aldehyde groups), or the bonding may occur by covalent coupling through the reaction of radicals in or on the nanoparticulate polymers, aggregates or conjugates with groups on the surface of the substrate either directly or through intermediate reactions.

Alternatively nanoparticulate polymers, aggregates or conjugates may be present on at least one surface of the substrate. For example a coating comprising the nanoparticulate polymers, aggregates or conjugates may be applied to the substrate.

Producing NanoP$^3$ Materials

Disclosed herein is a method for preparing a nanoP$^3$ material (including nanoparticulate polymers and aggregates thereof), the method comprising:
  i) providing at least one gas in a reaction chamber;
  ii) supplying power to a first electrode so as to generate a plasma in the reaction chamber;
  iii) applying a voltage to a second electrode in said reaction chamber; and
  iv) collecting the resulting nanoP$^3$ material;
wherein the at least one gas comprises an organic gas. At least one of the gases present acts a monomer.

Also disclosed herein is a method for preparing a nanoP$^3$ material (including nanoparticulate polymers and aggregates thereof), the method comprising:
  i) providing at least one gas in a reaction chamber;
  ii) supplying radio frequency (rf) power to a first electrode in said reaction chamber so as to generate a capacitively coupled plasma in the reaction chamber;
  iii) applying a voltage to a second electrode in said reaction chamber; and
  iv) collecting the resulting nanoP$^3$ material;
wherein the at least one gas comprises an organic gas. At least one of the gases present acts a monomer.

Also disclosed herein is a method for preparing a nanoP$^3$ material (including nanoparticulate polymers and aggregates thereof), the method comprising:
  i) providing at least one gas in a reaction chamber;
  ii) supplying radio frequency (rf) power so as to generate an inductively coupled plasma in the reaction chamber;
  iii) applying a voltage to a second electrode in said reaction chamber; and
  iv) collecting the resulting nanoP$^3$ material;

wherein the at least one gas comprises an organic gas. At least one of the gases present acts a monomer.

Also disclosed herein is a nanoparticulate polymer or an aggregate produced by a method as described herein.

FIG. 1 shows an example of an scaled up production of nanoparticulate polymers or aggregates, as defined herein, and their use in the production of therapeutic and diagnostic agents for clinical use. In part 1, the process can provide control over number and size of nanoparticulate polymers and aggregates, allowing for well-defined and tunable surface chemistry and activities. The nanoparticulate polymers and aggregates may be collected directly into clinical vials due to the presence of a sterile environment during their production. In steps 2 and 3, a one-step, direct and rapid functionalisation can occur, hence the need for complicated wet chemistry steps, along with washing or purification steps, is negated. Advantageously the choice of second species means that the products can be tailored for many therapies and/or diagnostics. A further advantage is the ability to upscale the processes (production of nanoparticular polymers, aggregates and/or conjugates with second specie(s)).

Also disclosed herein is a nanoP$^3$ material produced by a method as defined herein.

The organic gas may comprise a hydrocarbon. The hydrocarbon may be, or may comprise, an unsaturated hydrocarbon.

The nanoP$^3$ may be produced in the presence of an inert gas. Herein an "inert gas" refers to a gas which does not undergo chemical reactions under a set of given conditions, such as those used to prepare nanoparticulate polymers or aggregates thereof, as described herein. Inert gases include: helium, neon and argon.

In one embodiment the at least one gas in step i) is a mixture of two or more gases. One gas may be an inert gas which is not incorporated into the nanoparticulate polymer or aggregates thereof.

The at least one gas in step i) may comprise an element from group 15, 16 or 17 of the periodic table, for example nitrogen. Fragments of this gas may be incorporated into the nanoP$^3$ materials. For example the presence of nitrogen may result in the presence of amine, imine or nitrile groups, or a mixture thereof in the nanoP$^3$ material.

The gas may be at a pressure of about 1 to about 1500 Pa absolute, for example in a range of about 6 Pa to about 67 Pa.

The reaction chamber may be earthed. The if frequency may be about 1 to about 50 MHz. The if power may be about 5 W to about 500 W. Rf power may be applied to the first electrode, second electrode or to both electrodes. The rf power applied to the first electrode may be in a pulsed regime or a continuous regime. The pulsed bias voltage applied to the second electrode may be from about −1000V to about 1000V. This may be relative to the reaction chamber. The pulsed bias voltage applied to the second electrode may have a frequency of from about 1 Hz to about 50 kHz. It may be a pulsed rf bias voltage. The pulsed bias voltage may have a pulse duration from about 1 to about 150 microseconds. It may be AC or may be DC. The second electrode may be earthed or may be electrically isolated and allowed to acquire a floating potential determined by charging of the electrode in the discharge.

The distance between the first and second electrodes may be from about 5 to about 60 cm.

Step i) may comprise evacuating the reaction chamber. It may comprise flowing the gas, or individual gases thereof, through the reaction chamber. The step of evacuating may be to a pressure below that at which steps ii) and iii) are conducted.

The process may comprise collecting the nanoparticulate polymer and/or aggregates in a collector. The collector may be disposed between the first and second electrodes. It may be in close proximity to the second electrode. The collector may be a sealable vial. It may be made of an electrically conducting substance or an electrically non-conducting substance.

The process may comprise exposing the nanoparticulate polymer and/or aggregates to a gas. The gas may comprise, or may consist essentially of, one or more of nitrogen, oxygen and water vapour. The gas may be air. The gas may be nitrogen. The gas may be a gas which is reactive to the nanoparticulate material.

In one embodiment there is provided a process for preparing a nanoP$^3$ material, the process comprising:
  i) providing a gas in a reaction chamber at a pressure of from about 1 to about 1500 Pa absolute;
  ii) supplying radio frequency (rf) power at about 1 to about 50 MHz and 5-500 W to a first electrode in said reaction chamber so as to generate a plasma in the reaction chamber;
  iii) applying a pulsed negative bias voltage at a frequency of about 1 Hz to about 50 kHz and pulse duration of about 1 to about 150 microseconds to a second electrode in said reaction chamber, said second electrode being about 5 to about 20 cm from said first electrode; and
  iv) collecting the resulting nanoparticulate material;
wherein the gas comprises a hydrocarbon gas, nitrogen and a noble gas.

In one embodiment the voltage in step iii) is a self-bias, where the electrode acquires a floating potential by accumulation of charge from the plasma.

In one embodiment the voltage in step iii) is a pulsed bias voltage.

In another embodiment there is provided a process for preparing a nanoP$^3$ material, comprising:
  i) providing a gas in a reaction chamber at a pressure of from about 6 Pa to about 67 Pa absolute;
  ii) supplying radio frequency (rf) power at about 60 to about 20 MHz and 5-200 W to a first electrode in said reaction chamber so as to generate a plasma in the reaction chamber;
  iii) applying a pulsed negative bias voltage at a frequency of about 1 to about 5 kHz and pulse duration of about 10 to about 30 microseconds to a second electrode in said reaction chamber, said second electrode being about 5 to about 20 cm from said first electrode;
  iv) collecting the nanoparticulate material in a sealable vial disposed between the first and second electrodes and in close proximity to the second electrode; and
  v) exposing the nanoparticulate material in the sealable vial to an organic species so as to covalently bond said organic species to the nanoparticulate material and thereby produce a functionalised nanoparticulate material,
wherein the gas comprises a hydrocarbon gas, nitrogen and a noble gas.

In another embodiment there is provided a process for preparing a nanoP$^3$ material, comprising:
  i) providing a gas in a reaction chamber at a pressure of from about 6 to about 67 Pa absolute;

ii) supplying radio frequency (rf) and power at about 10 to about 15 MHz and 5-200 W to a first electrode in said reaction chamber so as to generate a plasma in the reaction chamber;

iii) allowing a second electrically isolated electrode to acquire a floating potential that is determined by charging of the electrode in the discharge in said reaction chamber, said second electrode being about 5 to about 20 cm from said first electrode;

iv) collecting the nanoparticulate material in a sealable vial disposed between the first and second electrodes and in close proximity to the second electrode; and v) exposing the nanoparticulate material in the sealable vial to an organic species so as to covalently bond said organic species to the nanoparticulate material and thereby produce a functionalised nanoparticulate material, wherein the gas comprises a hydrocarbon gas, nitrogen and a noble gas.

Also disclosed herein is an apparatus for producing a nanoP$^3$ material, said apparatus comprising: an evacuable reaction chamber; a first electrode disposed in said reaction chamber and coupled to an rf power supply; a second electrode disposed in said reaction chamber and coupled to a pulse generator or electrically isolated from the chamber; a vacuum pump coupled to the reaction chamber so as to at least partially evacuate said chamber; and at least one gas inlet for supplying one or more gases or a mixture thereof to the reaction chamber. The pulse generator may be DC or may be AC.

The apparatus may additionally comprise collectors for collecting the nanoP$^3$ material. The collectors may be disposed between the first electrode and the second electrode. The first and second electrodes may be between about 5 and about 60 cm apart.

Figure 4:
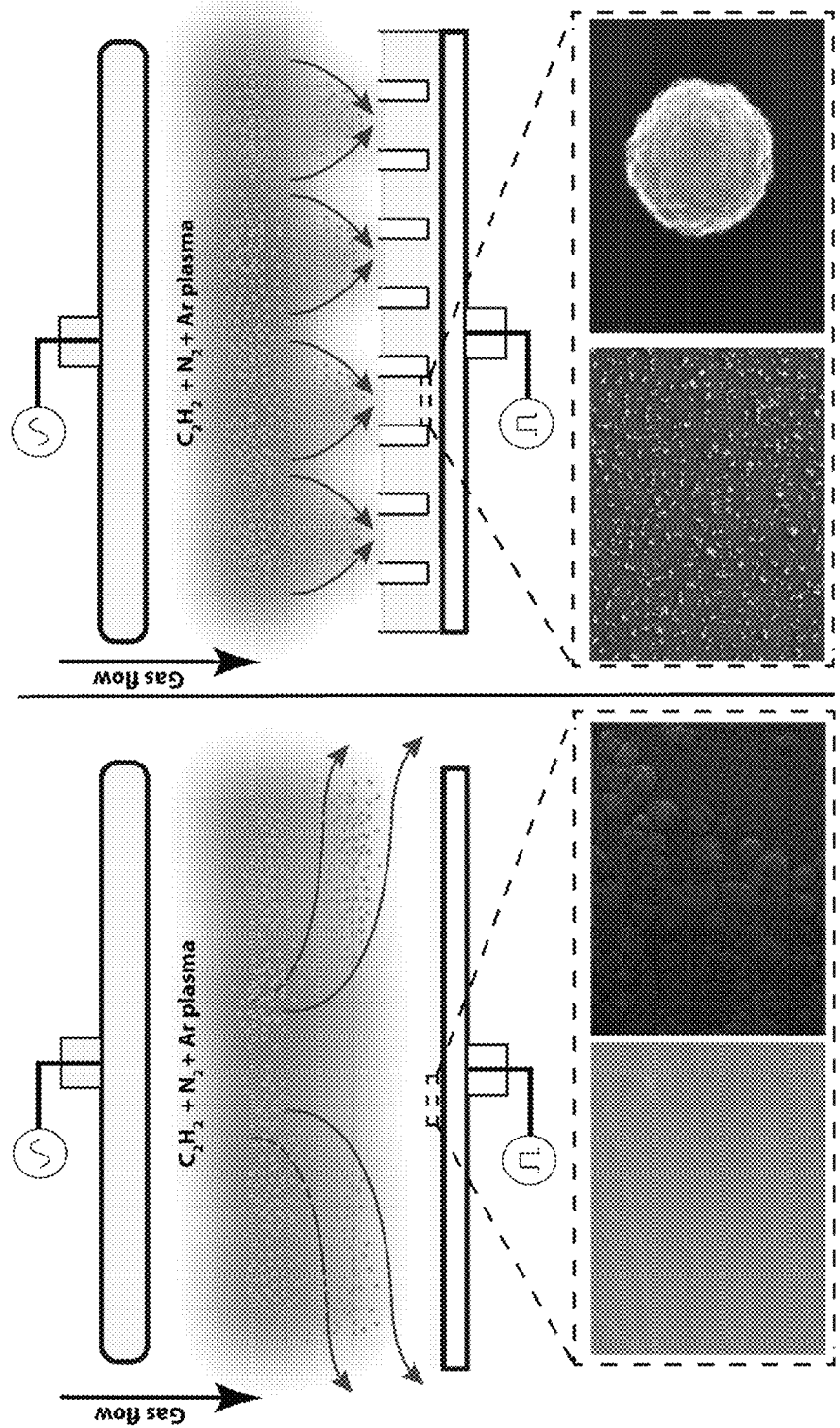
FIG. 4—Schematic of apparatus that may be used to obtain nanoP$^3$ material using different collection vessels.

FIG. 4 outlines a schematic of an apparatus that may be used to collect nanoP$^3$ material. The schematic exemplifies the collection mechanism of nanoparticles in a capacitively-coupled radio-frequency plasma sustain in a $C_2H_2$, $N_2$ and Ar gaseous mixture. On the left, the negatively charged nanoparticles remain in the plasma positive potential and are repelled from the substrate by ion drag forces and the potential drop along the plasma sheath. In this embodiment, a thin-film plasma coating is deposited on a flat substrate supported by the bottom electrode without evidence of nanoparticles (see insets below). On the right, the well-shaped nanoparticle collector coupled to the bottom electrode modifies the plasma potential. The plasma positive potential infiltrates into the collector, allowing the nanoparticles to be trapped inside the wells (see inset below). In one embodiment the nanoP$^3$ material is collected in an apparatus as described herein, for example utilising a collector as depicted in FIG. 4.

Also disclosed herein is the use of an apparatus defined herein for producing nanoP$^3$ material as defined herein.

In one embodiment of the process of preparing a nanoP$^3$ material, a first electrode is supplied with rf (radio frequency) power so as to generate a plasma within a reaction chamber and a second electrode that is allowed to float and attain a floating potential determined by its spontaneous charging in the discharge in said reaction chamber. The rf power applied to the first electrode should be sufficient to generate and sustain a plasma discharge. It should be sufficient to fragment, dissociate or ionize the gas, for example a mixture of hydrocarbon gas, reactive non-polymerisable gas and an additional gas, such as nitrogen, fragments of which may incorporated into the resulting polymeric material. It should be sufficient to produce radical species in the plasma discharge resulting from the dissociation and fragmentation of the gas. It should be sufficient to sustain a plasma discharge in the reaction chamber during the formation of the nanoparticulate material in the reaction chamber.

Figure 3:
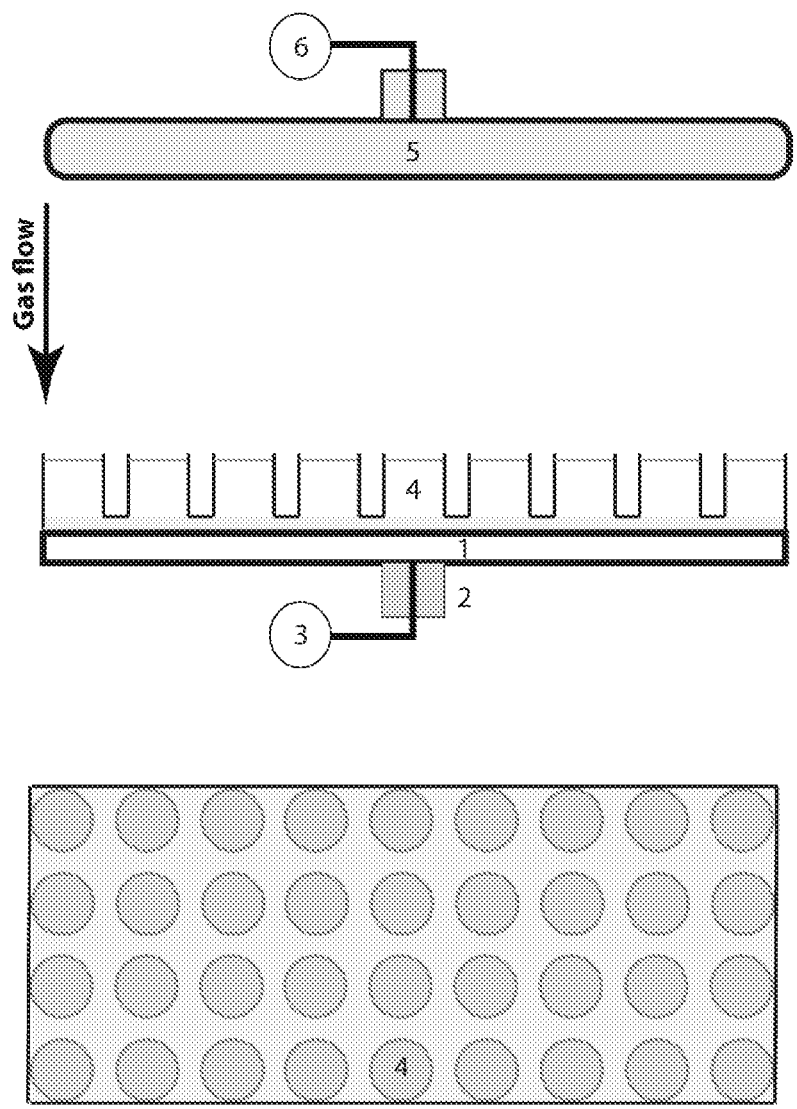
FIG. 3—Schematic of apparatus which may be used to produce nanoP$^3$ material.

FIG. 3 outlines apparatus that could be utilised in the formation of the nanoP$^3$ material. The figure shows the bottom electrode (1), electrode support (2), high voltage power supply connection for bottom electrode (3), well-shaped nanoparticle collector (4), top electrode (5) and high voltage power supply connection for top electrode (6). Combinations of (3) and (6) may be used herein. In one embodiment: (3) would be connected either to a pulsed high voltage power supply, or be at a floating potential (i.e., not connected to a power supply) and (6) would be connected to a radio-frequency power supply.

The rf frequency may be about 1 to about 200 MHz, or about 1 to 25, 1 to 50, 1 to 75, 1 to 100, 1 to 125, 1 to 150, or 1 to 175 MHz, e.g., about 1, about 2, about 3, about 4, about 5, about 10, about 11, about 12, about 13, about 14, about 15, about 16, about 17, about 18, about 19, about 20, about 21, about 22, about 23, about 24, about 25, about 26, about 27, about 28, about 29, about 30, about 40, about 50, about 60, about 70, about 80, about 90, about 100, about 110, about 120, about 130, about 140, about 150, about 160, about 170, about 180, about 190, or about 200 MHz.

It may have a power of about 5 to about 500 W, or about 5 to 100, 5 to 200, 5 to 300, or 5 to 400 W, e.g., about 5, 10, 20, 30, 40, 50, 60, 70, 80, 90, 100, 120, 140, 160, 180, 200, 250, 300, 350, 400, 450 or 500 W.

The pulsed bias voltage may have a frequency of about 1 Hz to about 50 kHz, or about 1 Hz to 20 kHz, 1 Hz to 10 kHz, 1 Hz to 5 kHz, 5 Hz to 50 kHz, 10 Hz to 50 kHz, 20 Hz to 50 kHz, 10 Hz to 20 kHz or 20 Hz to 30 kHz.

The bias voltage may be from about −1000V to about 1000 V, or −500 to 500, −200 to 200, −100 to 100, −50 to 50, −1000 to 0, −500 to 0, −200 to 0, −100 to 0, −50 to 0, 0 to 50, 0 to 100, 0 to 200, 0 to 500 or 0 to 1000V, e.g., about −1000, −900, −800, −700, −600, −500, −400, −300, −200, −100, −50, 0, 50, 100, 200, 300, 400, 500, 600, 700, 800, 900 or 1000 V.

In some embodiments the bias voltage is non-zero. It may therefore be either positive or negative and in each case may have an absolute value of from 10 to 1000, or 20 to 100, 50 to 1000, 100 to 1000, 200 to 1000, 500 to 1000 or 100 to 500 V. The pulsed voltage may be with respect to the chamber.

The chamber may be earthed. The second electrode may be earthed. Alternatively the voltage may be a self-bias, a result of charging of a floating electrode defined by the drop of the potential across the plasma sheath. The pulse duration may be from about 1 to about 150 microseconds, or about 1 to 100, 1 to 50, 1 to 20, 1 to 10, 10 to 150, 20 to 150, 50 to 150, 100 to 150, 10 to 100, 10 to 50 or 50 to 100 microseconds, e.g., about 1, 2, 3, 4, 5, 10, 15, 20, 25, 30, 35, 40, 45, 50, 60, 70, 80, 90, 100, 110, 120, 130, 140 or 150 microseconds.

The ratio between off time and on time of the pulses may be from about 10 (i.e., 10:1) to about 20, or about 10 to 15, 15 to 20 or 13 to 17, e.g., about 10, 13, 15, 17 or 20. In some instances it may be greater than 10, optionally up to 100, or up to 90, 80, 70, 60, 50, 40 or 30.

The first and second electrodes are suitably spaced apart, for example at a distance of about 5 to about 60 cm, or about 5 to 50, 5 to 40, 5 to 30, 5 to 20, 5 to 10, 10 to 60, 20, to 60, 30 to 60, 40 to 60, 10 to 30 or 20 to 40 cm, e.g., about 5, 10, 15, 20, 25, 30, 35, 40, 45, 50, 55 or 60 cm. Commonly the first electrode will be disposed above the second electrode.

During plasma generation the pressure within the reaction vessel is commonly between about 1 to about 1500 Pa absolute (about 7.5 mTorr to about 115 Torr), or about 10 to 1500, 100 to 1500, 200 to 1500, 500 to 1500, 600 to 1500, 700 to 1500, 800 to 1500, 900 to 1500, 1000 to 1500, 1100 to 1500, 1200 to 1500, 1300 to 1500, 1400 to 1500 Pa, e.g., about 10, 20, 30, 40, 50, 60, 70, 80, 90, 100, 150, 200, 250, 300, 350, 400, 450, 500, 600, 700, 800, 900, 1000, 1100, 1200, 1300, 1400, or 1500 Pa. Commonly to attain this pressure, the reaction vessel is initially evacuated to below this pressure, for example below about 10 mPa, or less than about 5, 2, 1, 0.5, 0.2 or 0.1 mPa. The desired pressure is then achieved by allowing the gas, or its individual component gases, to bleed into the chamber at a sufficient rate, which is adjusted together with the pumping speed, to attain the desired pressure and the desired monomer residence time in the chamber. The residence time of the gas molecules in the chamber determines the degree of fragmentation of the monomer and other gas molecules in the plasma. It will be understood that the required flow rate will depend on the size of the reaction chamber, however by monitoring the pressure within the reaction chamber (e.g., by means of a pressure gauge coupled to the internal space of the chamber), it is a simple matter to adjust the flow rate(s) and pumping speed to achieve the desired pressure and gas residence time. The gas may be prepared from the individual component gases before being introduced into the chamber or else the individual component gases of the gas may be introduced separately into the chamber. In the latter case the ratio of the component gases in the gas may be controlled by controlling the different flow rates of the different components. In the event that the gas comprises more than two individual components, at least one of the gases introduced into the chamber may be itself a mixture, or else each separate component gas may be introduced discretely. Component gases include an organic gas and may also comprise one or more carrier gases, one or more non-polymerisable gases and optionally other component gases.

The gas comprises at least one gas which is organic, i.e., contains carbon and is not carbon dioxide. At least one gas is a monomer as defined herein. It may comprise a carbon-carbon double bond and/or a carbon-carbon triple bond. It may be an alkene or an alkyne. It may be a mixture of such gases. The organic gas may be polymerisable under the conditions of the process. The gas may comprise more than one organic gas. In the present context, a gas is taken to be a substance which is in the gaseous state at the temperature and pressure prevailing at the time in the reaction chamber. Therefore, for example, pentane at standard temperature and pressure is a liquid, however at the reduced pressures of the present process it is regarded as a gas. In some instances, the gas may also be a gas at standard temperature and pressure, e.g., acetylene (ethyne).

The flow rate of the organic gas (or the sum of the flow rates of all organic gases) may be from about 0.1 to about 4000 sccm (standard cubic centimetre/minute), or about 1 to 4000, 10 to 4000, 50 to 4000, 100 to 4000, 500 to 4000, 1000 to 4000, 2000 to 4000, 0.1 to 2000, 0.1 to 1000, 0.1 to 500, 0.1 to 200, 0.1 to 100, 0.1 to 50, 0.1 to 10, 0.1 to 1000, 0.1 to 100, 0.1 to 10 or 0.1 to 1 sccm, e.g., about 0.1, 0.2, 0.5, 1, 2, 3, 4, 5, 10, 15, 20, 25, 30, 35, 40, 45, 50, 60, 70, 80, 90, 100, 150, 200, 250, 300, 350, 400, 450, 500, 600, 700, 800, 900, 1000, 1500, 2000, 2500, 3000, 3500 or 4000 sccm. The flow rate of the carrier and reactive non-polymerisable gas(es) may then be adjusted to achieve the desired pressure and residence time within the reaction chamber. The collection time may be from less than 1 minute to about 30 minutes, or from 1 to 20, 1 to 10, 1 to 50, 5 to 30, 10 to 30, 20 to 30, 5 to 20, 5 to 10 or 10 to 20 minutes, e.g., about 1, 2, 3, 4, 5, 6, 7, 8, 9, 10, 15, 20, 25 or 30 minutes or may be longer than 30 minutes. The collection time may be in the range of about 30 seconds to about a minute.

It will be appreciated that any of the flow rate, pressure and power may be varied according the specifically desired properties of the nanoP$^3$ material to be produced. Thus, any of the numerical values or ranges exemplified herein for each of the flow rate, pressure and power may be used together, in any combination. For example, in one embodiment, a flow rate of from about 0.5 to about 10 sccm, a pressure of about 20 Pa and a power of about 50 W to about 100 W may be used. All other possible combinations are envisaged herein.

In one embodiment the method further comprises the introduction to an organometallic compound in step i). Examples of organometallic compounds include: iron oxide and gadolinium compounds.

In one embodiment, the nanoP$^3$ material produced from the plasma as described above may be collected in one or more collectors, for example a collector as described in FIG. 4. The collector(s) may be disposed close to the second electrode. It (they) may be disposed below the first electrode. It (they) may be disposed vertically below the first electrode between the first and second electrodes. It (they) may allow the capture of the nanoparticulate material in the active plasma region. This is important since it controls particle agglomeration. The collector(s) may allow the collection of the nanoparticulate material in the active glow plasma region. In one embodiment the collector(s) are or comprise vials or a plurality of vials. Alternatively or in addition, the collector(s) are or comprise one or more wells. The plurality of vials may be in the form of wells in a plate. In another embodiment the vials or wells may have a depth of from about 2 to about 20 mm, or from about 2 to 10, 2 to 5, 5 to 20, 10 to 20 or 5 to 10, for example about 2, 3, 4, 5, 6, 7, 8, 9, 10, 11, 12, 13, 14, 15, 16, 17, 18, 19 or 20 mm. In some instances the vial(s) may be deeper than 20 mm.

The base of the collector may be completely planar or may be substantially planar (e.g., the edges of the base may be rounded at their point of contact with the side walls of the collector, or may be rounded up to form the side walls of the collector). The surface area of the base of the collector may be tailored as desired in order to collect nanoP$^3$ materials of preferred geometries. Similarly, the height of the side walls of the collector (i.e., their distance from the base of the collector) may be tailored as desired in order to collect nanoP$^3$ materials of preferred geometries.

In one example, the height of the side walls of the collector may be from 1 mm to 50 mm, such as 1 mm to 40 mm, such as 1 mm to 30 mm, such as 1 mm to 20 mm. Thus, the height of the side walls of the collector may be from 3 mm to 17 mm. Alternatively, the height of the side walls of the collector may be from 2 mm to 20 mm, or from 5 mm to 15 mm, or from 7 mm to 12 mm, or any other suitable range. In another example, the height of the walls of the collector may be about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm or about 20 mm. In one preferred embodiment, the height of the side walls of the collector is about 17 mm. Other heights can be selected according to the desired geometric properties of the nanoP³ material. The height of the side walls can be selected according to the monomer(s) used to synthesise the nanoP³ material.

The shape of the circumference of the well-shaped collector may also be tailored according to the desired geometric properties of the nanoP³ material. The shape of the circumference of the well-shaped collector may also be tailored according to the monomer(s) used to synthesise the nanoP³ material. By way of example only, the shape of the circumference of the well-shaped collector may be circular, square, oval, rectangular, triangular, pentagonal, hexagonal, etc., or substantially circular, substantially square, substantially oval, substantially rectangular, substantially triangular, substantially pentagonal, substantially hexagonal, etc.

Where the base of the collector is generally circular, the radius may be chosen based on the desired size and yield of the intended nanoP³. In one example, the radius may be from 1 mm to 50 mm, such as from 1 mm to 40 mm, or from 1 mm to 30 mm, or from 1 mm to 20 mm, or from 1 mm to 10 mm, or from 2 mm to 8 mm, or from 3 mm to 7 mm, or from 4 mm to 6 mm. Alternatively, the radius may be about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm.

The ratio of the height of the side walls of the collector to the radius of the collector may be tailored according to the desired size and yield of nanoparticulate material. In one example, the ratio of the height of the side walls of the collector to the radius of the collector is from about 5:1 to 0.1:1. For example, the ratio of the side walls of the collector to the radius of the collector may be from about 3:1 to 1:1, or from about 1.8:1 to 1:1, or from about 1.6:1 to 1:1. The ratio of the side walls of the collector to the radius of the collector may be about 5:1, or about 4:1, or about 3:1, or about 2:1, or about 1:1, or about 0.8:1, or about 0.6:1, or about 0.4:1, or about 0.2:1.

The collector may be sealable. Thus, the vial(s) or well(s) may be sealable. Since exposing the vial or well to a plasma effectively sterilises it, collecting the nanoparticulate material directly in the vial or well provides a convenient way to both collect and sterilise the vial or well in a single step. Since, as discussed elsewhere herein, the nanoparticulate material may be used for therapeutic purposes, or in the formation of conjugates and pharmaceutical compositions for therapeutic uses, sterilisation may be important in their final use. The collector may be made of a non-conducting material or it may be made of a conducting material. It may be made of a material capable of withstanding a plasma. It may for example be made of glass.

Once the nanoP³ material has been generated and collected, the reaction chamber may be vented (i.e., brought to about ambient pressure) with nitrogen. The nanoP³ material may then be exposed to a reactive gas. This may be by removing them from the plasma chamber or by allowing the reactive gas to enter the chamber. The nanoP³ material, commonly radical sites in the nanoparticle material, may then react with the reactive gas. This may result in formation of functional groups which may be used to react the nanoP³ material with organic species, such as a second species as defined herein, so as to attach those organic species to the nanoP³ material. Commonly the gas will be air or nitrogen, however other gases may be used. The gas may be an oxygen containing gas. It may be a water vapour containing gas. It may contain both water vapour and oxygen. Alternatively or additionally the nanoP³ material may be reacted with a second species such as an organic or organometallic species, e.g., an imaging reagent, a protein, a siRNA, an RNA, a biomolecule, a catalyst, a drug, whole cells, cell fragments, micelles, liposomes, hydrogels, polymer particle, semiconductor particle, ceramic particle, metal particle, or mixtures of any two thereof, so as to attached, for example covalently attach, the second species to the nanoP³ material.

The present disclosure provides a convenient means to access a wide range of functionalised nanoparticles. The size of the nanoparticles, and the functional density, may be tailored by adjusting the conditions under which they are generated. For example, by generating and collecting the nanoP³ material within a plasma chamber, the particles may be sealed inside a sterilised container. They may be then functionalised at will with a suitable second species, such as an organic species, optionally shortly before use, by injecting a suitable reagent containing the organic species into the sealed vial.

Where particles of the nanoP³ material are synthesised inside a vacuum chamber where a reactive mixture of gases, containing at least one hydrocarbon precursor and at least one buffer (or carrier) gas, is used to generate a low pressure and low temperature plasma discharge. The plasma discharge is generated by coupling, either inductively or capacitively, the power generated and delivered to the system by a power supply or a combination of power supplies, such as radio-frequency (rf) generator, dc power supply or pulsed dc power supply. The exceptional power transfer within the plasma gaseous discharges together with the high energy excitation thresholds of the buffer gases, provides a very efficient mechanism to ionize and dissociate the hydrocarbon precursor molecules via collisions between the latter and other species present in the plasma (either charged species such as electrons and ions or neutral species, including atoms and molecules available from the buffer gases). The interaction between the precursor molecules and the other species initiate a chain of chemical reactions, leading to the formation of radicals and high-order hydrocarbons and ultimately to the formation of the nanoparticles via nucleation and aggregation processes. The production of carbon-based nanoparticles using hydrocarbon containing plasma discharges allows for definite controllable and scalable process windows where the size, production rate, surface chemistry, morphology and radical concentration of the nanoparticles are defined by tuning the various process parameters—applied power, plasma excitation frequency, gas mixture, precursor residence time, system pressure and discharge time. Additionally, the inclusion of gases such as nitrogen not only allows tailoring of the nanoparticle surface chemistry but also modulates particle dispersion and aggregation in aqueous solution.

The Inventors consider that the nanoP³ material results from the dissociation and fragmentation of the monomer (e.g., a hydrocarbon) and other gases (such as nitrogen) in the plasma discharge. Radical species resulting from such dissociation mechanisms recombine in the plasma volume to form nanoP³ material containing unpaired electrons. The unpaired electrons trapped in the nanoparticulate structure may then be used to covalently immobilize biomolecules.

The present disclosure includes a collection process that utilises a pulse biased nanoparticle collector wherein the growth and removal phases, collection yield and size monodispersity of nanoparticles can be tightly controlled. The electrical pulses provided to the nanoparticle collector can be modulated with a variety of temporal profiles and a wide range of negative and positive applied voltages. Pulse temporal profiles include square waves. These may have a duty cycle of at least 1%. They may have a frequency ranging from 1 Hz to 3 kHz and applied voltage in the range −1000 V-1000 V. Additionally, the collector features a well-like geometry that readily allows an efficient and high yield recovery of the nanoparticles in the active glow plasma region. The shape, depth and spacing between different wells determine nanoparticle collection yields and aggregation. Particularly, nanoparticle yield rates of 14.4 g/hr m2 may be achieved using a collector featuring 24 circular wells with a well radius of 0.8 cm, or using a collector featuring 96 circular wells with a well radius of 0.635 cm. Other suitable well plates can be chosen as desired.

Figure 2:
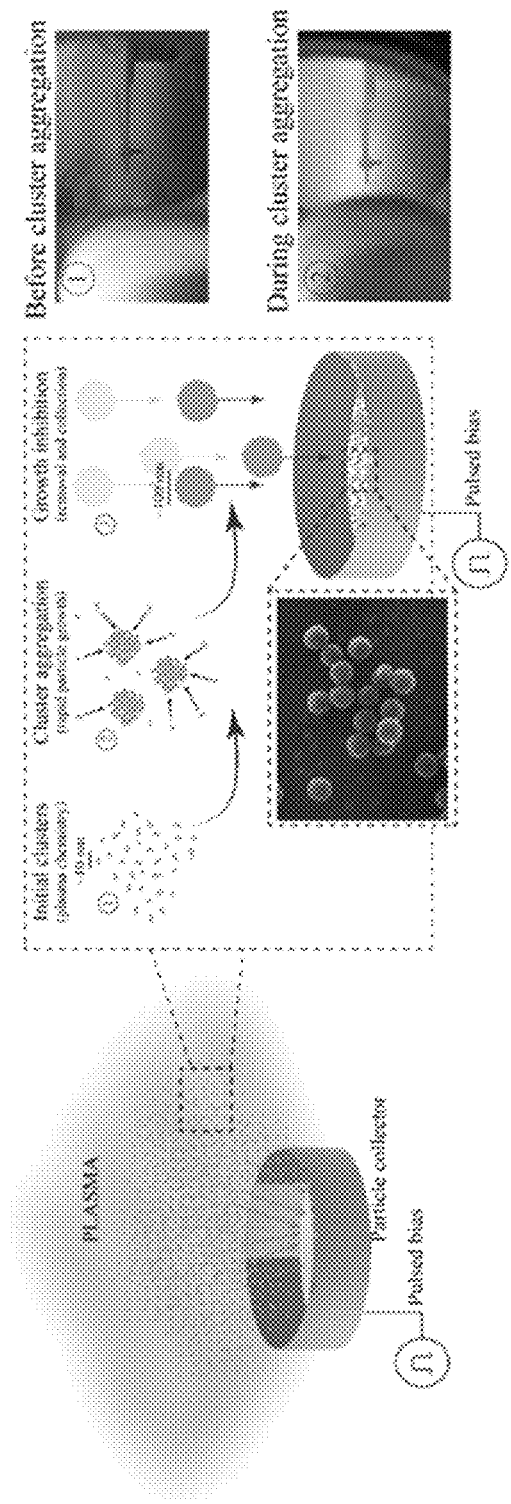
FIG. 2—A schematic depicting the formation, growth and collection of nanoP$^3$ particles in a plasma discharge.

FIG. 2 briefly depicts proposed mechanisms involved in the formation and growth of the nanoparticles. During the fabrication process two groups of particles with distinctive size ranges are formed in different growth phases: a first group of particles with a size of up to around 10 nm and a second group comprising particles with diameters ranging from about 100 nm up to about 500 nm. Analysis of the morphology of the particles by scanning electron microscope (SEM) imaging (see inset in FIG. 2) suggests that the second group of particles (larger spherical-shaped particles) are aggregates of the nanoparticulate polymers from the first group. The nanoparticulate polymers are formed in an initial phase and their growth is ruled by the plasma chemistry (phase 1). The latter is essentially dependent on the type of monomer and other gases present used to produce the discharge as well as their degree of fragmentation, dictated by the species residence time and energy input to the plasma discharge. The mechanism of formation of these initial nanoparticulate polymers may follow different paths and can be dominated by growth reactions involving either neutral radicals or negative or positive ions. The number density of these initial nanoparticulate polymers in the plasma normally exceeds the electron and the ion densities. According to the principle of quasi-neutrality, this may indicate that the mean charge of the nanoparticulate polymers is near to zero.

When the nanoparticulate polymers reach a critical size in the plasma (of about 5 nm up to about 10 nm) the negatively and positively charged clusters start to come together to form the second group of larger particles, the aggregates (phase 2). During this phase, all the growing particles behave as a sink for electrons and ions present in the plasma, with the diffusion of charged species towards them ruled by plasma sheath dynamics. This phenomenon is confirmed in FIG. 5 (images B and C) where the time evolution of the ratio between emission bands associated with molecular ions and other non-charged species are shown to be in opposite phase with the overall plasma spectrum. Particularly, a rapid decrease in the ion populations during the aggregation and growth phases is observed, indicating that ionic species could be further consumed during phase 2. During the aggregation and rapid growth phases a spherical sheath is formed around the growing particles. The development of this spherical sheath is most likely the reason leading to the formation of aggregates with a spherical shape such as those shown in FIG. 2. Because of their higher mobility the electrons diffuse more rapidly towards the particles when compared to the positive ions. Consequently, the growing particles are charged negatively and their growth is enhanced by attracting more positively charged clusters and positive ions. After reaching a critical size (which is dependent on the plasma parameters) and a critical density, the assembled negative charge on the particles surface inhibits further nanoparticulate polymer aggregation.

Because the particles are negatively charged, they are confined to the positive plasma potential zone due to the electrostatic forces. Once the particles reach a critical size and mass other forces acting on the particles become more dominant (e.g., ion drag force, thermophoretic force, gas viscous force and gravity force) and overcome the electrostatic forces, forcing the particles to be pushed away from their creation and growth zones. The removal of the particles leads to the formation of a particle-free zone and gives room for a new creation and growth cycle and subsequent removal and collection of the newly formed particles (phase 3). During this phase the overall emission intensity of the discharge decreases. Additionally, the relative ionic fraction in the plasma increases again indicating that ions are no longer consumed due to their diffusion towards the particles.

The applied voltage in the nanoP$^3$ collector may modulate the dynamics of particle formation and removal phases. While the aggregation and removal phases have the same duration if no bias is applied, increasing negative voltages up to −500 V promotes longer nanoparticle removal phases. Increasing the bias intensifies the electrical force that is applied to the growing nanoparticles. Therefore, a further increase in the nanoparticle mass is necessary in order for the gravitational force to overcome the sustaining electrical forces and push the particles away from the discharge. Consequently, longer aggregation phases result in further aggregation of the nanoparticulate polymers, and therefore their consumption, to form the bigger nanoP3 material. A controlled biasing of the nanoparticle collector provides a method of filtering the smaller nanoparticulate polymers away the collector, enhancing therefore the size monodispersity of the collected nanoP$^3$ material. Further increase in the applied bias deters nanoparticulate polymer aggregation and subsequent particle formation as shown by the abrupt decrease in aggregation and removal phases and by a decrease in the nanoparticle yields.

Figure 5:
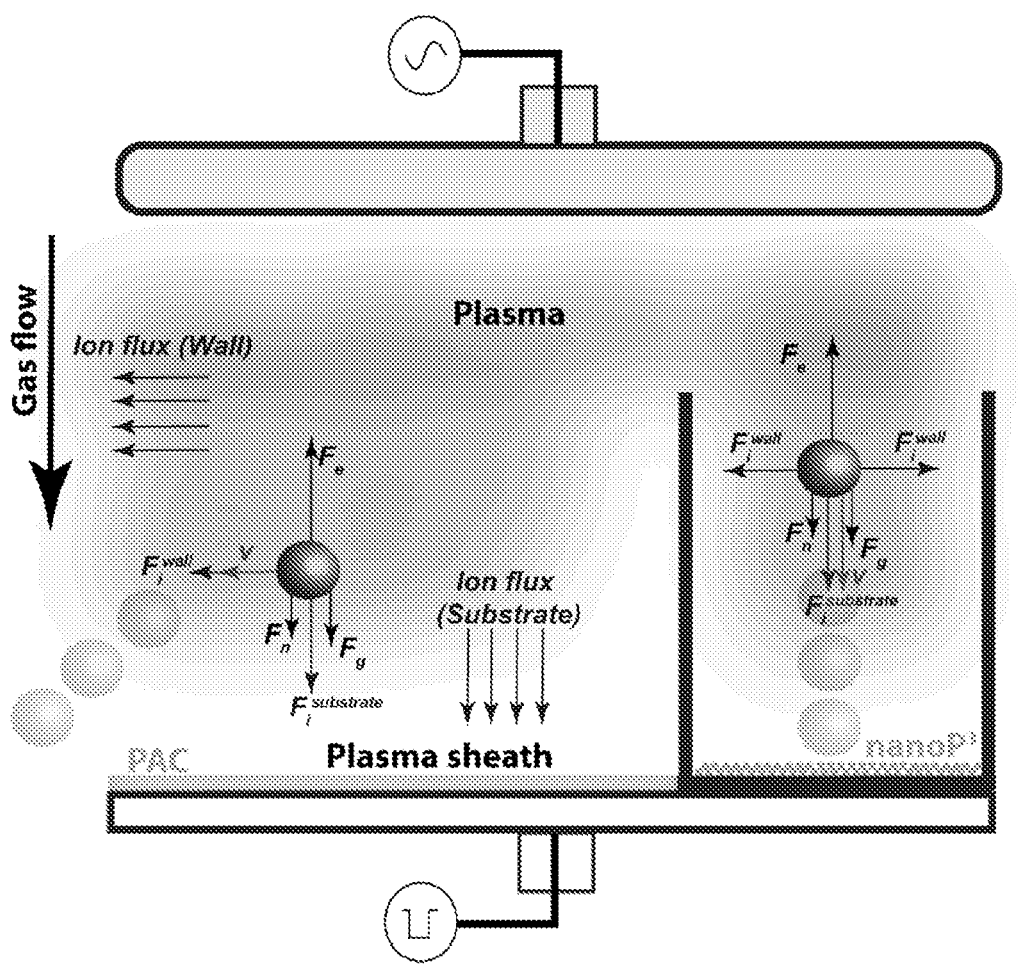
FIG. 5—Schematic illustrating the forces acting on nanoP$^3$ outside and inside a collector well.

The formation of nanoP$^3$ can be shown to be a periodic process where consecutive generations of particles with the same characteristics can be created and continuously collected during a single run. This periodic behaviour of particle formation can be directly observed, for instance, by collecting the radiation emitted by the plasma and analysing it by means of optical emission spectroscopy (OES), as shown in FIG. 5.

The method disclosed herein can return a nanoparticle yield rate of 14.4 g/hr m$^2$ using a collector featuring 24 circular wells with a well radius of 0.8 cm.

Producing Conjugates

Disclosed herein is a method of forming a conjugate, the method comprising:
  providing:
    i) a nanoparticulate polymer, an aggregate, or a mixture thereof; and
    ii) at least one second species; and
  contacting the nanoparticulate polymer or aggregate and the at least one second species such that the nanoparticulate polymer or aggregate and the at least one second species become physically or chemically associated with one another.

The nanoparticulate and/or aggregate may be made by a method described herein.

During the formation of the conjugate the at least one second species may be covalently or electrostatically bound to the nanoparticulate polymer or aggregate.

The process of forming a conjugate may comprise reacting the nanoparticulate polymer or aggregate with at least one second species such as an organic or organometallic species so as to bond, for example covalently bond, said second species to said nanoparticulate polymer or aggregate, and thereby produce a conjugate in the form of a functionalised nanoP$^3$ material. The step of reacting the nanoparticulate polymer or aggregate may comprise exposing the nanoparticulate polymer or aggregate to said second species at a temperature of from 0 to about 30° C. The process may comprise exposing the nanoparticulate material to said second species for a times ranging from about 1 minute to about 24 hours. The nanoparticulate material may be collected in a collector, in which case the step of reacting may comprise introducing the second species into the collector. The second species may be in solution or in dispersion or in suspension.

In one embodiment a conjugate comprising a nanoP$^3$ material and at least one second species, is formed in a one-pot reaction.

More than one second species can be combined with the nanoP$^3$ material to form a conjugate. The addition of two or more second species to a nanoP$^3$ material can occur in a single one pot reaction or in sequential separate reactions. In one embodiment a conjugate is formed between a nanoP$^3$ material and at least two second species, in a one-pot reaction. In another embodiment a conjugate is formed between a nanoP$^3$ material and at least two second species, in two separate reactions, which may be consecutive.

Following the formation of a conjugate, additional sites capable of binding one or more further second species, may remain on the conjugate, for example in the form of unbound electrons or functional moieties which may have been introduced onto the conjugate via attachment of a second species. This is advantageous if two second species cannot be introduced in a single step due to different chemical properties such as disparate solubility profiles, or where protecting group chemistry is required to retain specific moieties.

Once a conjugate has been formed it is possible that functional groups incorporated into the monomers of the nanoparticles, or present on a second species introduced following formation of the conjugate, can be used in subsequent steps for attaching further second species.

The coupling of the nanoparticulate polymer or aggregate to a second species may be rapid and may be conducted under mild conditions. The coupling conditions may be temporally altered to facilitate binding of charged species. Thus the reaction may be essentially complete (e.g., 90, 95 or 99% complete) within 30 minutes, or within 20, 25, 10, 5 minutes, 1 minute or less. The reaction may be conducted at ambient conditions, or at a temperature of between about 0 and about 50° C., or about 0 and 30, 0 and 20, 10 and 50, 20 and 50, 30 and 50, 10 and 30 or 20 and 30° C., e.g., about 0, 5, 10, 15, 20, 25, 30, 35, 40, 45 or 50° C. It will be recognised that higher temperatures will encourage more rapid reactions; however the reactions should be conducted at a temperature at which the second species, for an organic species such as a biomolecule, is stable. This temperature will depend on the nature of the second species, or the mixture of second species being utilised in the conjugation process.

Thus a nanoparticle-based technology that allows the chemical conjugation of a range of different molecular cargos, tailored to the functional requirements of specific applications, is described herein. The functionalisation of the nanoP$^3$ material may be readily achieved by direct bonding of the molecular cargos to radicals and/or functional moieties embedded within the particles. The immobilisation of biomolecules onto the nanoP$^3$ material may be a one-step process, achieved by simple incubation without the need for intermediate coating, pre-functionalisation and passivation steps with organic molecules or other chemical intermediates. Thus, the methods of producing the nanoP$^3$ material disclosed herein may not comprise any coating, pre-functionalisation, passivation steps, or any mixture of these steps. The favourable surface chemistry of the nanoP$^3$ material is a result of the fabrication process by plasma discharges, involving the diffusion and aggregation of monomer radicals and functional groups onto the growing particle during the formation and growth phases in the discharge volume. Furthermore, the proposed fabrication and collection process allows control over the nanoP$^3$ material properties, in particular their size, radical content, morphology, surface chemistry, aggregation and production yield rates can be controlled by adjusting the plasma parameters.

The processes and methods disclosed here may comprise the step of setting plasma parameters (gas pressure, power, frequency, pulse length, voltage etc.) so as to achieve a desired property or combination of properties for the nanoP$^3$ materials.

Immobilised biomolecules can maintain their bioactivity after being immobilised onto the surface of the nanoP$^3$ materials. Both bare nanoparticles and biomolecule conjugated nanoparticles can be readily internalised by various cell types and do not induce cytotoxicity in cells at all tested concentrations. Additionally, drug-conjugated nanoparticles may maintain cytotoxic capacity after internalisation by cancer cells. Importantly, the covalent immobilisation capability of the nanoparticles and the bioactivity of biomolecule conjugated nanoP$^3$ materials are shown to be maintained after long-term freeze-dried storage, e.g., for at least about 1 month, or at least about 2, 3 or 6 months, or at least about 1, 2, 5 or 10 years. The processes and methods disclosed herein are convenient ways of producing and using plasma nanoparticles, as a new class of multifunctional and versatile nanocarriers for nanomedicine applications.

Present nanoparticle functionalisation strategies rely on several methods of surface modifications to add active surface chemistry, comprised mostly of non-ionic polymers and specific targeting ligands for targeted drug delivery. This represents, however, additional intermediate, complex, time-consuming and costly steps in the fabrication process. Moreover, the coatings that are presently used on the nanocarriers provide only very poor drug loading capacities. The unique surface chemistry of nanoP$^3$ materials, as described herein, allow for a strong covalent bond with the cargo without the need for intermediate functionalisation strategies. This means the defined nanoP$^3$ materials have a great potential to overcome one of the major limitations of currently available platforms. The particles produced by methods recited herein may be functionalised in a simple one-step process directly after manufacture and sold with tailored functionalities suited to a particular application in therapeutics, imaging and diagnostics.

It has been shown that the nanoP$^3$ can covalently immobilise different molecular cargos via radical attachment and/or via functional moieties, while maintaining the bioactivity of the molecules. Further in vitro assays have been performed to evaluate the uptake by different types of cells. Results show that the nanoP$^3$ can be easily taken up by cells without the need of any particular cell penetrating agent. The nanoP$^3$ materials are biocompatible and well tolerated, with no signs of cell toxicity after up to 4 days post uptake, while drug conjugated nanoP$^3$ is effective in inducing cytotoxicology in cancer cells. Additionally, nanoP$^3$ can deliver siRNA inside cells, significantly reducing protein expression 48 hours after cellular uptake.

Conjugates involving molecular cocktails may involve targeting ligands such as antibodies or proteins to target the diseased tissue; imaging agents to enable real-time tracking of the particles to the target tissue and/or therapeutic proteins or small molecules such as drugs, enabling the formation of a multifunctional nanocarrier. The radical-mediated binding capacity of nanoP$^3$ materials disclosed herein dictates the concentration of proteins and drugs to inject into the vial of nanoP$^3$ material, in such a manner that all ligands bind to the nanoparticles, leaving no free proteins or drugs. After a rapid 5-minute incubation, the resulting solution of drug loaded conjugates may be injected into the patient with no time consuming wet-chemistry, pre-conjugation, washing or purification steps. This facilitates the upscaling and translation of the technology for clinical use in hospitals.

The Inventors have shown that it is possible to successfully conjugate biomolecules to nanoparticles stored in air (at room temperature) at least 2 months after nanoparticle fabrication and that the ability of nanoP$^3$ to immobilize cargo remains virtually constant during the first 6 months of storage in air at room temperature. NanoP$^3$ samples stored up to 16 months also retained the capacity to bind significant amounts of cargo, and any slight decrease in binding efficiency observed after that storage time could be overcome simply by increasing the concentration of the cargo in solution. When stored in water (at room temperature) the radical density in the nanoparticles is reduced by 70% 1 to 2 weeks after fabrication. The radical density in the nanoparticles is only reduced by 44% if the nanoP$^3$ materials are stored in air at room temperature 1 to 2 weeks after fabrication. The pre-conjugation shelf-life could be significantly improved to many months or some years by sealing the vials inside the plasma chamber, under vacuum conditions immediately after collection and by storing the nanoparticles at lower temperatures.

EXAMPLES

The present disclosure is now described further in the following non-limiting examples.

Materials and Methods:

Synthesis of NanoP$^3$

Nanoparticles were synthesised using the procedure outlined in FIG. 2.

NanoP$^3$ particles were synthesised in a cylindrical stainless steel capacitively coupled radio-frequency (rf) reactor. The reactor was pumped down to a base pressure of ~10$^{-6}$ Torr using a dual dry vacuum pump system comprised of an Ebara PDV250 and a turbomolecular pump (Edwards NEXT400). Reactive gaseous mixtures of argon, nitrogen and acetylene were used to sustain the plasma discharge and were introduced through a shower-head like apparatus located at top part of the chamber. The flow rate of each gas was individually controlled by Allicat Scientific mass flow controllers and the working pressure, measured by a full range gauge (PFEIFFER PKR251), prior to plasma generation was maintained constant at 150 mTorr unless stated otherwise. A butterfly-type valve was placed between the chamber and the pumping system and was adjusted to control the pumping efficiency and therefore the residence time of the species in the active plasma. Plasma discharges were generated and sustained by coupling the rf power, supplied by a 13.56 MHz (Eni OEM-6) frequency generator, to the top electrode using a purpose built matching network. The nanoparticle collector was placed in a second electrode (10 cm distant from the rf electrode) which was electrically connected to a DC high voltage pulse generator (RUP 6-25) to provide a specific bias voltage in the range −1000 V-0 V. Pulse frequency and time width was chosen to be 3 kHz and 20 µs respectively.

Optical Emission Spectroscopy

The radiation emitted by the plasma was captured by an optical fibre placed in line of sight with the plasma region immediately above the nanoparticle collector. Discharge spectra were monitored by a UV-VIS-NIR spectrometer (Ocean Optics HR 4000 with a spectral resolution of ~0.2 nm) and recorded by a personal computer covering a wavelength range of 200-1000 nm. For an improved signal-to-noise ratio the integration time was set to 300 ms at 10 scans to average for each acquisition. High resolution spectra were obtained using an Acton SpectraPro 2750 spectrometer (Princeton Instruments, USA) equipped with a 1200 grooves mm$^{-1}$ grating, resulting in a nominal resolution of 0.014 nm for an entrance slit opened at 50 µm. Discharge emission spectra were captured by a PI-MAX (Princeton Instruments, USA) intensified charge-coupled device (ICCD) with a 1024×1024-pixel array optically coupled with the spectrometer's exit plane. The ICCD exposure time was 300 µs and the number of averaged acquisitions was varied between 25 and 150. The entire optical setup was kept unchanged throughout the experiments. Particular measurements were performed in order to obtain the temporal profile of the intensities associated with specific radiative transitions involving several species in the plasma (FIG. 2).

X-Ray Photoelectron Spectroscopy

Chemical characterisation of the nanoparticles was studied by means of X-ray photoelectron spectroscopy (XPS) using a SPECS-XPS (Germany) equipped with a hemispherical analyser and an Al Kα monochromatic X-ray source. The system was operated at a constant pressure of ~10$^{-9}$ torr, with a takeoff angle of 90° at a power of 200 W. Survey spectra of the samples were scanned in the energy range of 50 eV-1400 eV using an energy step of 1 eV and an energy pass of 30 eV. High resolution scans for C1s, N1s and O1s were recorded with an energy step of 0.03 eV and an energy pass of 23 eV. Peak analysis was performed using CasaXPS software. The atomic fraction of these elements in the particles was determined by calculating the integrated areas of the C1s, N1s and O1s peaks and assuming that they sum to 100% (i.e., neglecting hydrogen and traces of other elements). Peak fitting was carried out by adopting a Shirley background and convoluted Lorentzian (30%)-Gaussian (70%) line shapes with identical full-width half maximum for each component. Charge compensation was applied in all spectra by assigning the C—C/C—H component in the C1s peak at a binding energy of ~285 eV.

Fourier Transform Spectroscopy

Infrared spectra were recorded by means of Fourier transform spectroscopy in attenuated total reflectance mode (FTIR-ATR) using a Bruker Hyperion FTIR microscope integrated in Vertex v70 system and equipped with a 20×ATR objective with a germanium crystal. Each spectrum resulted by averaging a total of 500 scans at a spectral resolution of 4 cm$^{-1}$ in the wavenumber range of 4000 cm$^{-1}$-750 cm$^{-1}$. Spectral subtraction and baseline was applied so as to eliminate background signal from the underlying substrate.

Scanning Electron Microscopy and Energy Dispersive X-Ray Spectroscopy.

Nanoparticles were imaged with a Zeiss ULTRA PLUS scanning electron microscope at acceleration voltages ranging 3 kV-10 kV and at working distances between 4 and 8.5 mm.

Electron Spin Resonance Spectroscopy

The detection of unpaired electrons in the nanoparticles was carried out by means of ESR spectroscopy using a Bruker EMXplus X-band spectrometer. Spectra were collected with a centre field of 3490 G, sampling time of 90 ms, modulation amplitude of 3 G, modulation frequency of 105 Hz and microwave frequency and power of 9.8 GHz and 25 mW respectively. The nanoP$^3$ material was suspended in ultra-pure water and transferred inside quartz glass Suprasil flat cells with a sample volume capacity of 150 μL. Quantitative EPR analysis was carried out by comparing the double integrated spectra of nanoparticles with a standard sample of known spin linear density (~$10^{13}$ spins/cm).

Zeta Potentials

The surface charges of nanoP$^3$ and conjugated-nanoP$^3$ materials were determined by measuring the zeta-potential in a disposable folded capillary cell (Malvern, DTS1070) using a Zetasizer Nano ZS (Malvern Instruments, Germany). The average values and the corresponding S.D. were calculated; n=3.

In Vivo Imaging

NanoP$^3$ was conjugated to Luciferase from Photinus pyralis (abcam, L9506) at 2.5 μg/ml in nuclease-free water for 1 hour at 4° C., gently agitated using Bio RS-24 mini-rotator. Conjugation of Luciferase to 200 nm gold nanoparticles (Cytodiagnostics; G-200) was performed in an identical fashion. After incubation, the nanoP$^3$ samples were washed 3 times via centrifugation at 16,100 g, 5 minutes per wash in nuclease-free water, whereas, gold nanoparticles were washed equally 3 times per manufacturer's instructions. Each sample was then resuspended in 100 μl saline and transferred into 1 ml syringe.

The animals were divided into 4 different groups:
(1) no intervention;
(2) nanoP$^3$ only;
(3) gold nanoparticles with luciferase and
(4) nanoP$^3$ with luciferase.

A wound was then created at the back of the mice prior to tail vein injections. For detection of luciferase, at each determined time points, D-Luciferin (Sigma-Aldrich; A1888) was subcutaneously injected into each animal. Bioluminescence was then detected (Exposure time: 3 mins) at the wound side via an IVIS system.

General Method for Synthesising Conjugates

NanoP$^3$ was collected from the nanoparticle collector under sterile conditions in a tissue culture hood with RT-PCR Grade water (Life technologies, 4387936). The concentration of nanoP$^3$ was measured by NanoSight NS300. NanoP$^3$ was incubated with desired second species to form conjugates for 1 hour at 4° C., and gently agitated using Bio RS-24 mini-rotator. After incubation, the samples were washed via centrifugation at 16,100 g, for 5 mins.

Example 1—Synthesis of NanoP$^3$

Nanoparticulate polymers and aggregates were prepared using the method outlined in the "Synthesis of NanoP$^3$" section above. It will be appreciated that other nanoparticulate polymers and aggregates can be formed from other monomers than acetylene.

By controlling the polymerisation of hydrocarbon monomers in the plasma volume, for example by using alkyne discharges, the Inventors were able to engineer and collect functional nanoparticulate polymers and aggregates and demonstrate their immobilisation capability, facilitating multifunctional nanocarriers. The nanoparticulate polymers and aggregates can, in one example, be synthesised in a plasma polymerization reactor, previously developed to deposit plasma polymer thin films (M. Santos, et al., *ACS Appl. Mater. Interfaces,* 8, 9635-9650, 2016; G. Yeo, et al., *ACS Biomater. Sci. Eng.,* 2 (4), 662-676, 2016; the content of which is incorporated herein by reference). The formation of the nanoparticulate polymers and aggregates can be monitored in real time using non-invasive, in-situ optical emission spectroscopy (FIG. 2). The formation of small nanoparticulate polymers (~10 nm) was initially revealed by a 32% increase in the overall plasma emission intensity (FIG. 2 "Before cluster aggregation"). While electrostatically suspended in the discharge, the nanoparticulate polymers then rapidly condensed to form highly spherical aggregates (~100 nm). The aggregation phase coincides with a rapid upsurge in the discharge emission and a 5-fold increase in the density of collected aggregates (FIG. 2 "During cluster aggregation"). When the net force acting on the particles pushes them out of the plasma, the discharge emission returns to baseline values registered at the beginning of the growth cycle. During this removal phase the falling particles are attracted to a well-shaped, pulsed biased collector, which allows controlled collection of nanoP$^3$ with well-defined and monodispersive size. While previously reported oscillations in alkyne discharge feature damping over time (J. Winter, et al., *Plasma Sources Sci. Technol.,* 18 034010 (8 pp), 2009), the Inventors stabilised nanoparticle formation by adding N$_2$ into the reactor (see methods), allowing an uninterrupted formation and collection of nanoparticles.

FIG. 2 depicts a schematic showing formation, growth and collection of nanoparticulate polymers and aggregates in the plasma/gas phase. Insets show images of the plasma before and during nanocluster aggregation and a SEM micrograph of aggregates as collected.

To modulate the properties of the nanoparticulate polymers and aggregates and optimise collection yields the plasma was sustained in a series of different conditions of gas flow, rf power and pressure. The Inventors maximised the yield rate of nanoparticulate polymers and aggregates by modulating the:
(i) power coupled to the discharge;
(ii) discharge pressure;
(iii) monomer flow rate; and/or
(iv) collector dimensions.

The nanoparticulate polymers and aggregates surface area/volume ratio was maximised at higher monomer flow rates due to a decrease in the size of the initially formed nanoparticulate polymers that condense to form the spherical, solid and amorphous aggregates. Increasing the if power also allowed production of higher yields of nanoparticles and smaller aggregates while keeping low polydispersity indices. The forces understood to be acting on nanoP$^3$ outside and inside the collector wells during nanoP$^3$ synthesis are illustrated in FIG. 5. The schematic of the particle on the left assumes a vertical equilibrium position near the plasma sheath formed above the substrate holder. This position is defined by a balance between the electrostatic force and gravitational, neutral drag, and the vertical component of the ion drag force. The horizontal component of the ion drag force, due flux of ions towards the lateral walls of the reactor, eventually drags the nanoparticle out of the active plasma before they can reach the substrate surface. Contrarily, the particle on the right is trapped as the positive plasma potential penetrates into the well. The gravity and drag forces overcome the electrostatic force as the particle increases in size, dragging it towards the bottom of the well. The horizontal components of the ion drag forces cancel each other inside the well.

Figure 6:
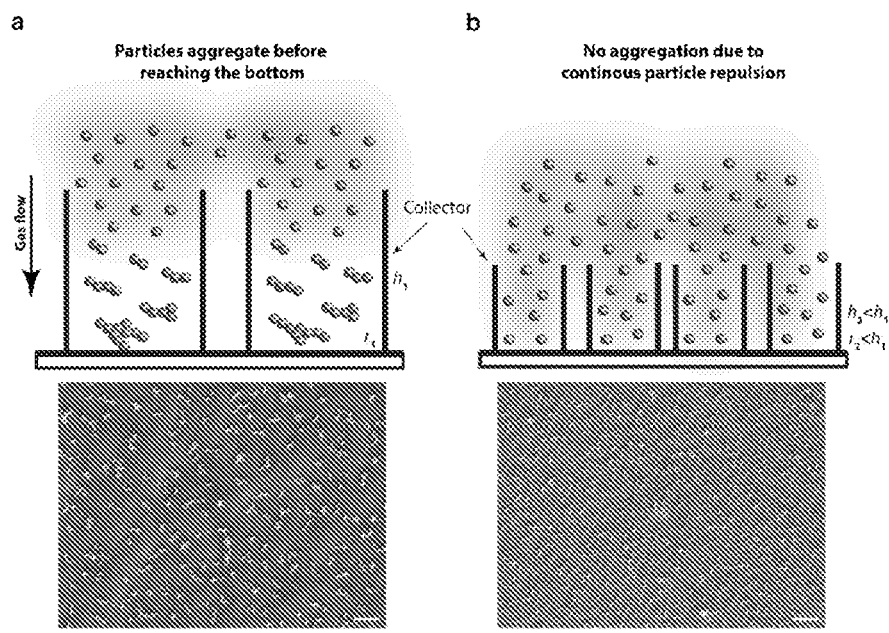
FIG. 6—Schematic illustrating the formation of nanoP$^3$ in collector wells of different dimensions.

Particle aggregation may be modulated by the height (h) and radius (r) of the wells. FIG. 6 part A shows that the plasma positive potential is not able to fully infiltrate towards the entire well. While the particles repel each other in the active plasma via Coulomb repulsion, the development of an afterglow region inside the well triggers particle aggregation before they reach the bottom. The inset shows an SEM image of nanoP$^3$ aggregates collected in wells with $h_1$=17 mm and $r_1$=7.8 mm. FIG. 6 part B shows the extension of the afterglow region was reduced in wells with $h_1$=11 mm and $r_1$=3.4 mm, allowing to collect nanoP$^3$ with minimal aggregation. Thus, the dimensions of the collector can be varied in order to produce nanoparticles and aggregates of a preferred size.

Figure 7:
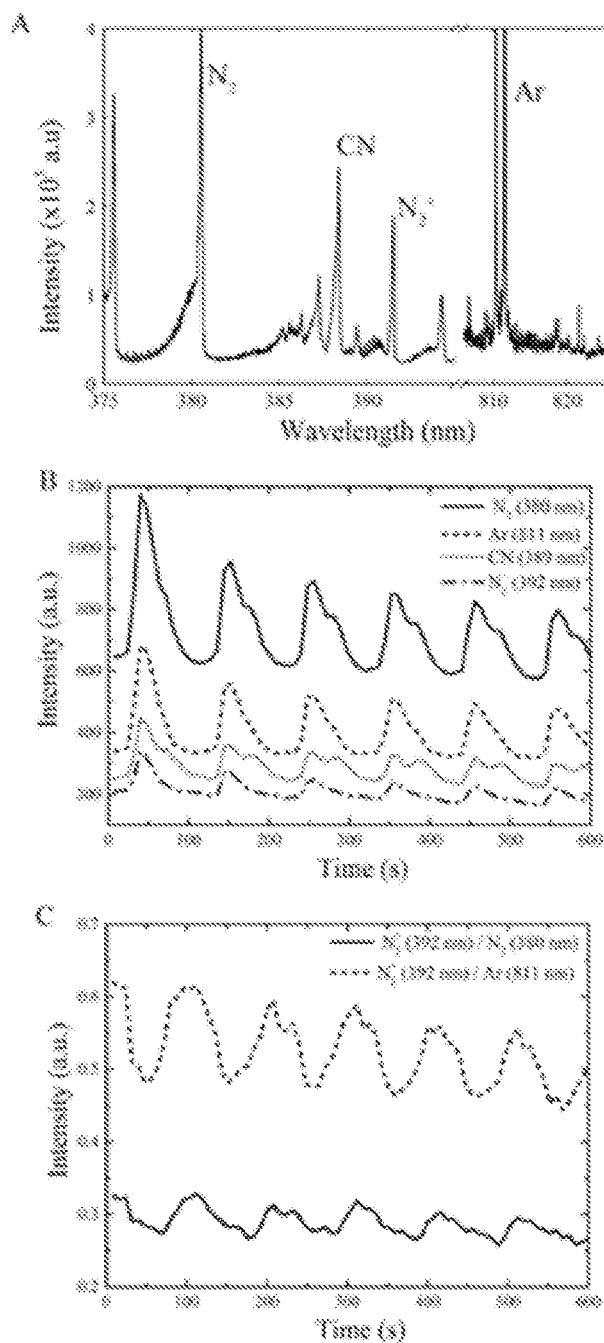
FIG. 7—Spectra indicating: optical emission spectrum of plasma (A); temporal profile of molecular emission bands (B); and temporal profiles of the ratios between emission intensities related to molecular ions and other non-charged species (C).

FIG. 7 image A shows an overall optical emission spectrum of the plasma acquired during the fabrication of nanoP$^3$. Here the particles were produced using a reactive mixture of acetylene (carbon precursor), nitrogen and argon in a capacitively-coupled radio-frequency reactor at an excitation frequency of 13.56 MHz, applied power of 50 W and a total gas pressure of 80 mTorr. The particle collector was biased using 20 μs pulses at a voltage of −500 V and a frequency of 3 kHz.

Temporal profiles of molecular emission bands and atomic lines related with several radiative transitions in the discharge are indicated in FIG. 7, image B. The time evolution of the plasma spectrum does not follow a steady-state behaviour but exhibits well-defined long time scale fluctuations. The observed oscillations are related with the cycles of formation and growth of the nanoparticles and their subsequent removal from the plasma volume (the numbers correspond to the different phases depicted in FIG. 2). Temporal profiles of the ratios between emission intensities related to molecular ions and other non-charged species are shown to be in opposite phase with the temporal profile of the plasma spectrum (FIG. 7, image C). This shows that ions may be further consumed during cluster aggregation and rapid growth phases.

Figure 8:
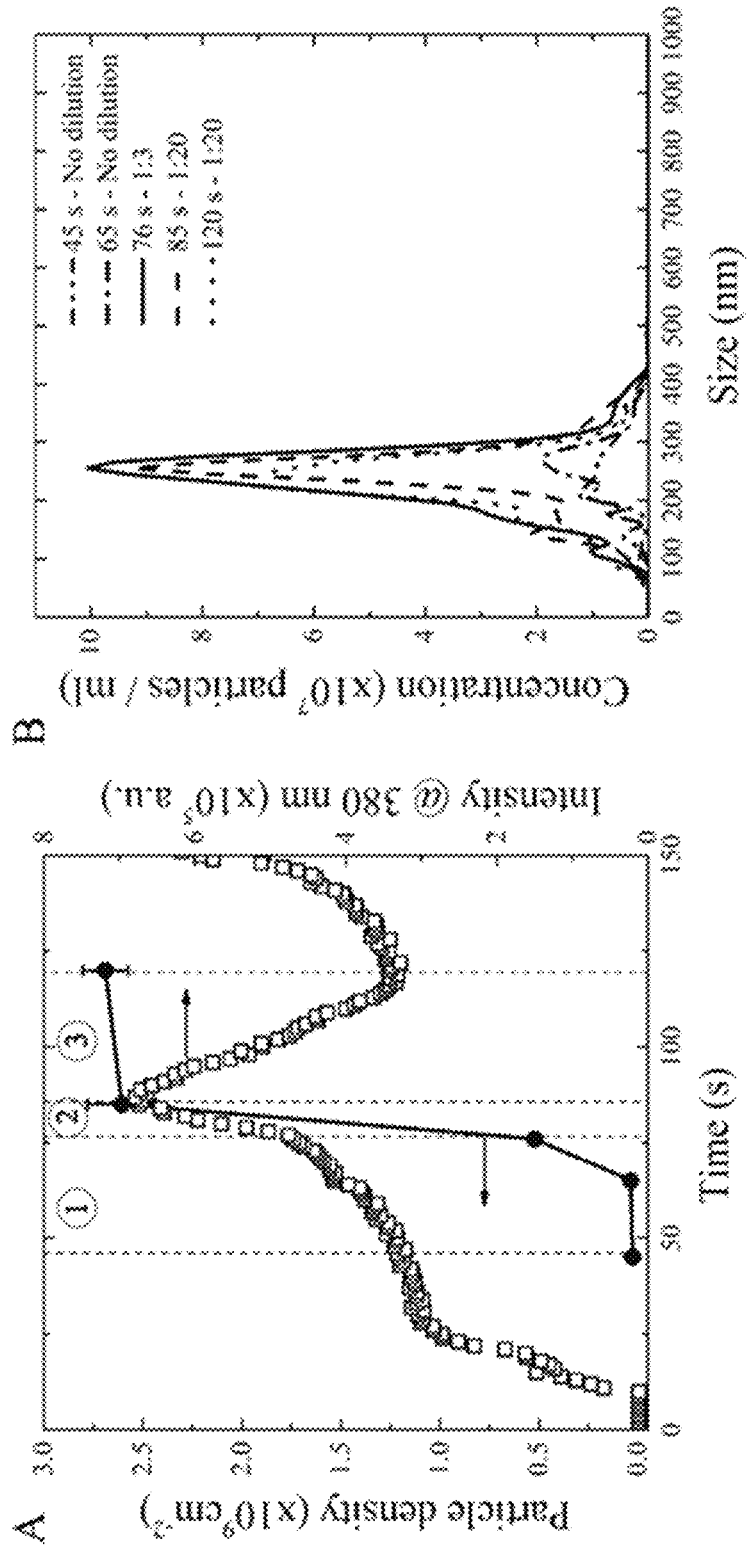
FIG. 8—Graphs depicting: number of nanoparticles per unit area of the collector and emission intensity measured at 380 nm at different time points during nanoparticle formation (A); and size distribution of nanoparticles collected at different time points in the discharge measured by dynamic light scattering (B).

FIG. 8 image A shows the number of nanoparticles per unit area of the collector and emission intensity measured at 380 nm at different time points during nanoparticle formation and growth in the discharge volume. The abrupt increase between 76 seconds and 85 seconds (phase 2 in FIG. 2) in both nanoparticle density and emission intensity indicates a rapid aggregation phase where small clusters nucleate to form larger and spherical nanoparticles. The emission intensity decreases during the removal phase (3), where no further particles are created as suggested by the unchanged number of collected nanoparticles. FIG. 8 image B shows the size distribution of nanoparticles collected at different time points in the discharge measured by dynamic light scattering. Nanoparticles collected during and after the rapid aggregation phase (≥76 seconds) feature a narrower size distribution due to a complete nucleation of the smaller clusters.

Figure 9:
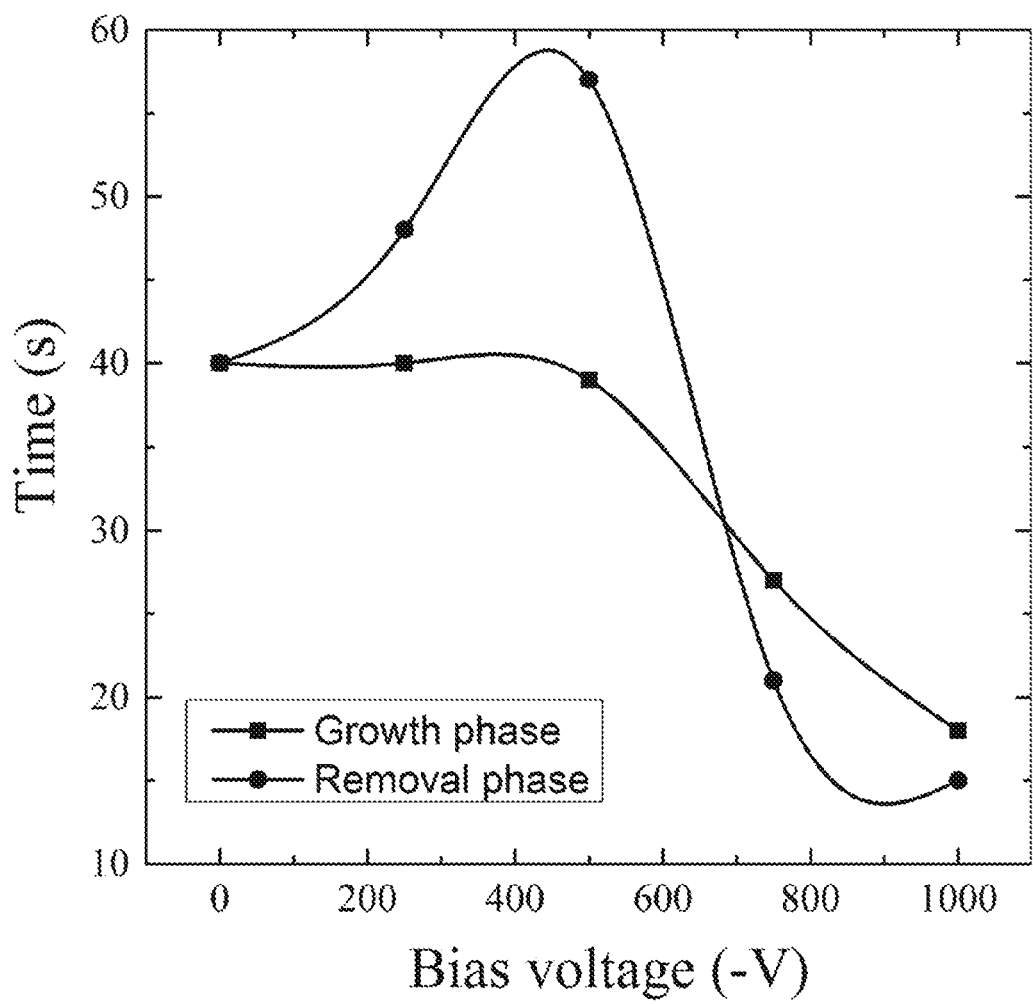
FIG. 9—Graph depicting duration of cluster aggregation (phase 2) and particles removal (phase 3) as a function of the applied bias in the nanoparticle collector (B).

FIG. 9 also shows the duration of cluster aggregation (phase 2; Growth phase) and particle removal (phase 3; Removal phase) as a function of the applied bias in the nanoparticle collector.

Figure 10:
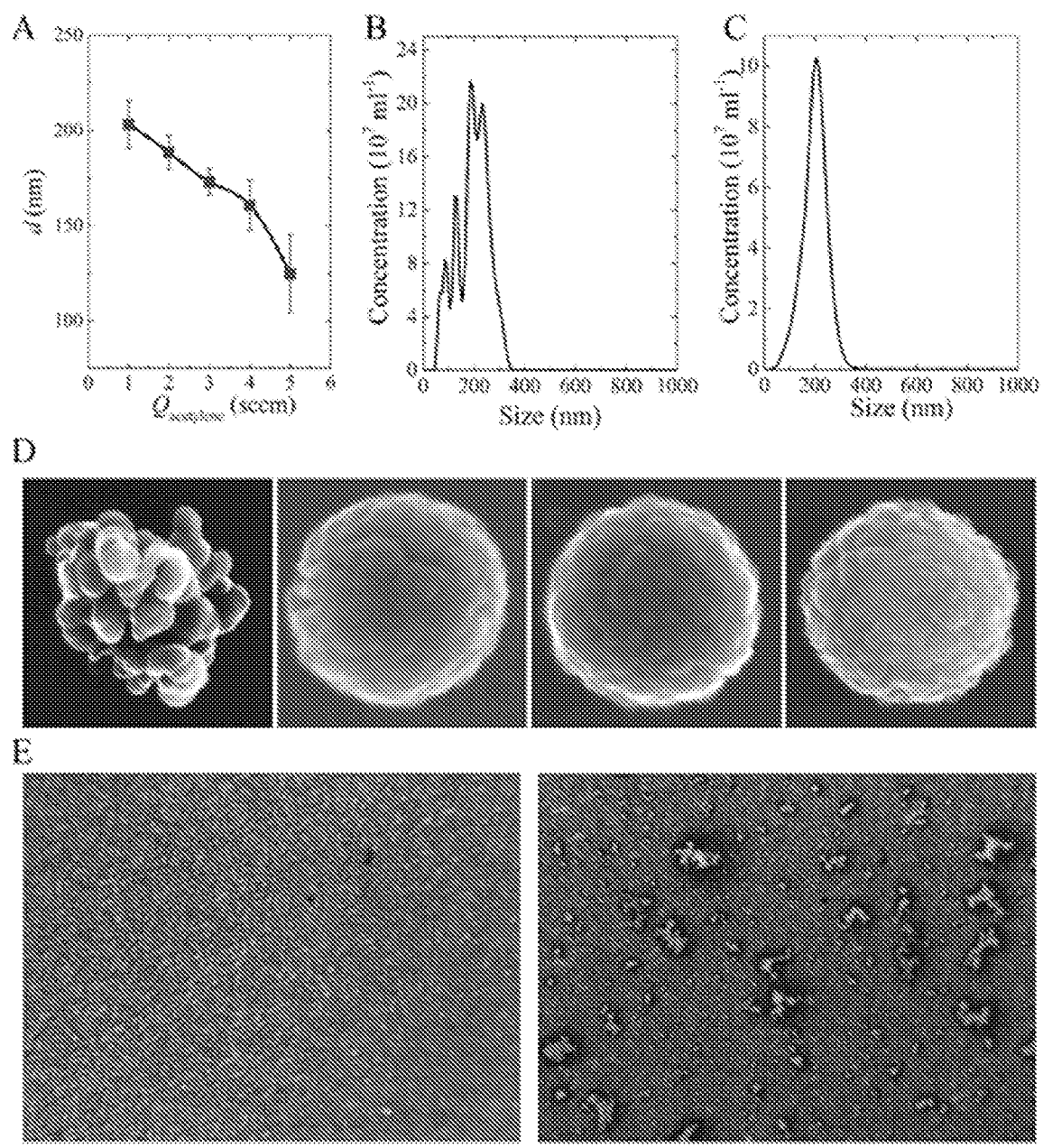
FIG. 10—Size analyses of nanoparticulate and aggregate products, and the morphology of the obtained particulate material.

The production of nanoparticles using the methods described herein allows fine control of a particle growth rate, dependent on one or more process parameters and the time at which the particles are collected after the plasma is ignited. FIG. 10 image A shows the particle diameter measured by SEM as a function of the monomer flow rate. Thus, the size of the nanoparticulate polymers and aggregates disclosed herein can be modulated by varying one or more parameters of the process by which they are made. For example, the size of the nanoparticulate polymers and aggregates disclosed herein can be increased by decreasing the flow rate. Conversely, the size of the nanoparticulate polymers and aggregates disclosed herein can be decreased by increasing the flow rate. It will be appreciated that the size of the nanoparticulate polymers and aggregates disclosed herein can be modulated by varying one or more other parameters of the process by which they are made. For example, the size of the nanoparticulate polymers and aggregates disclosed herein can be increased by decreasing the radio frequency power. Conversely, the size of the nanoparticulate polymers and aggregates disclosed herein can be decreased by increasing the radio frequency power.

Controlling the nanoparticle size is important for specific tailoring in different nanomedicinal applications. For instance, it is known that the biodistribution and the pharmacokinetics after particle injection are dependent on the size of the nanoparticles.

The importance of using a pulsed bias particle collector in the size distribution of the collected nanoparticles is further exemplified in FIG. 10, image B. Biasing the collector (FIG. 10, image B) is found to improve size selectivity of the collected nanoparticles when compared to the more polydispersive size of nanoparticles retrieved in an unbiased collector (FIG. 10, image C). Another beneficial feature of the products defined herein is the ability to tightly regulate size distribution of the nanoparticulate materials. SEM imaging shows that nanoparticles have a very narrow size distribution, all with approximately the same diameter (FIG. 10, image D). The monodisperse size distribution of the particles is an inherent characteristic of nanoparticles produced by the presently described methodology.

Additionally, the nanoparticles are characterised by a large surface to volume ratio when compared to currently available spherical nanoparticle platforms (for example, spherical gold nanoparticles and other spherical metallic or polymeric platforms). The increased surface area, when compared with smooth spherical surfaces, results directly from the fabrication process which involves the aggregation of small clusters to form larger spherical, cauliflower-like particles. By tuning the plasma parameters it is possible to tailor the surface area of the nanoparticles. FIG. 10, image D shows nanoparticles synthesised in distinct plasma runs where different carbon precursor flow rates were used. In this experiment all other plasma parameters (e.g., pressure, power and flow rates of buffer gases) remained constant. Increasing monomer flow rate (from left to right) led to the creation of nanoparticles with rougher surfaces, i.e., particles with a larger surface area. Thus, the surface roughness of the nanoparticulate polymers and aggregates disclosed herein can be modulated by varying one or more parameters of the process by which they are made. For example, the surface roughness of the nanoparticulate polymers and aggregates disclosed herein can be increased by increasing the monomer flow rate. Conversely, the surface roughness of the nanoparticulate polymers and aggregates disclosed herein can be decreased by decreasing the monomer flow rate.

Increasing the carbon-source molecules' flow rate leads to an increase in their density which results in higher neutral drag forces that drag the clusters away from the plasma. Additionally, a reduction in the dissociation and ionization of these carbon species is also expected due to a reduction of their residence time in the plasma. Consequently, the growth of the initial clusters is suppressed in earlier stages before they are allowed to aggregate and form bigger particles. Therefore, higher flow rate regimes trigger an even more rapid aggregation of clusters to form nanoparticles featuring smaller sized but a higher quantity of clusters. It will be appreciated that smaller nanoparticles or aggregates as disclosed here in, and/or nanoparticles or aggregates with a rougher surface, can increase the surface area/volume ratio of the nanoparticles and/or aggregates. Thus, the surface area/volume ratio of the nanoparticles and/or aggregates disclosed herein can be modulated by varying one or more parameters of the process by which they are made. For example, the surface area/volume ratio of the nanoparticles and/or aggregates disclosed herein can be modulated by varying the monomer flow rate.

A large surface to volume ratio is a desirable feature for nanoparticles, especially in therapeutic applications, allowing higher drug-loading capacity per nanoparticle, increasing drug efficiency and therefore reducing toxicity. Improving the effective surface of the nanoparticle also leaves additional room for further surface functionalisation (without compromising drug loads) with targeting ligands for the recognition of targeted cells, stimulus-sensitive agents for controlled delivery, imaging and therapeutic agents or even multiple drugs in a single stable construct. In the field of medical imaging for instance there is an increasing demand for multimodality imaging. Multimodal imaging techniques aim to combine anatomical imaging technologies (for structural details) with functional imaging technologies (for functional and morphological details) into a unique platform for synchronous image acquisition in time and space. Therefore, there is a need to incorporate all the necessary imaging contrast agents into a single platform. The surface of nanoparticulate polymers or aggregates can be functionalised with several contrast agents and due to its larger surface area, enhanced signals and resolutions can be achieved. Finally, nanoparticle agglomeration during the removal and collection phase can be controlled by choosing the appropriate collector geometry. Micron-size aggregates were found to be formed when using a collector with a well depth of 17 mm (FIG. 10, image E, right-hand side) while aggregate-free samples were collected if using a well depth of only 3 mm (FIG. 10, image E, left-hand side).

Analysis of Surface Chemistry and Chemical Conjugation Ability

Results show that nanoparticles and aggregates produced using acetylene in the presence of nitrogen are mainly composed of carbon and nitrogen (FIG. 11), for nanoparticles produced in acetylene/nitrogen/argon plasma discharges. Hydrogen is also expected to be present, however it cannot be detected using this technique. The surface elemental composition and bonding configuration of the nanoparticles was analysed in more detail with X-ray photoelectron spectroscopy. Results reveal the presence of carbon, nitrogen and oxygen in relative concentrations of 65.6%, 27.6% and 6.8%, respectively. Thus, the nanoparticles and/or aggregates disclosed herein may comprise carbon, nitrogen and oxygen in relative concentrations of from 60-70%, from 20-30% and from 5-10%, respectively (e.g., as determined by X-ray photoelectron spectroscopy).

Figure 11:
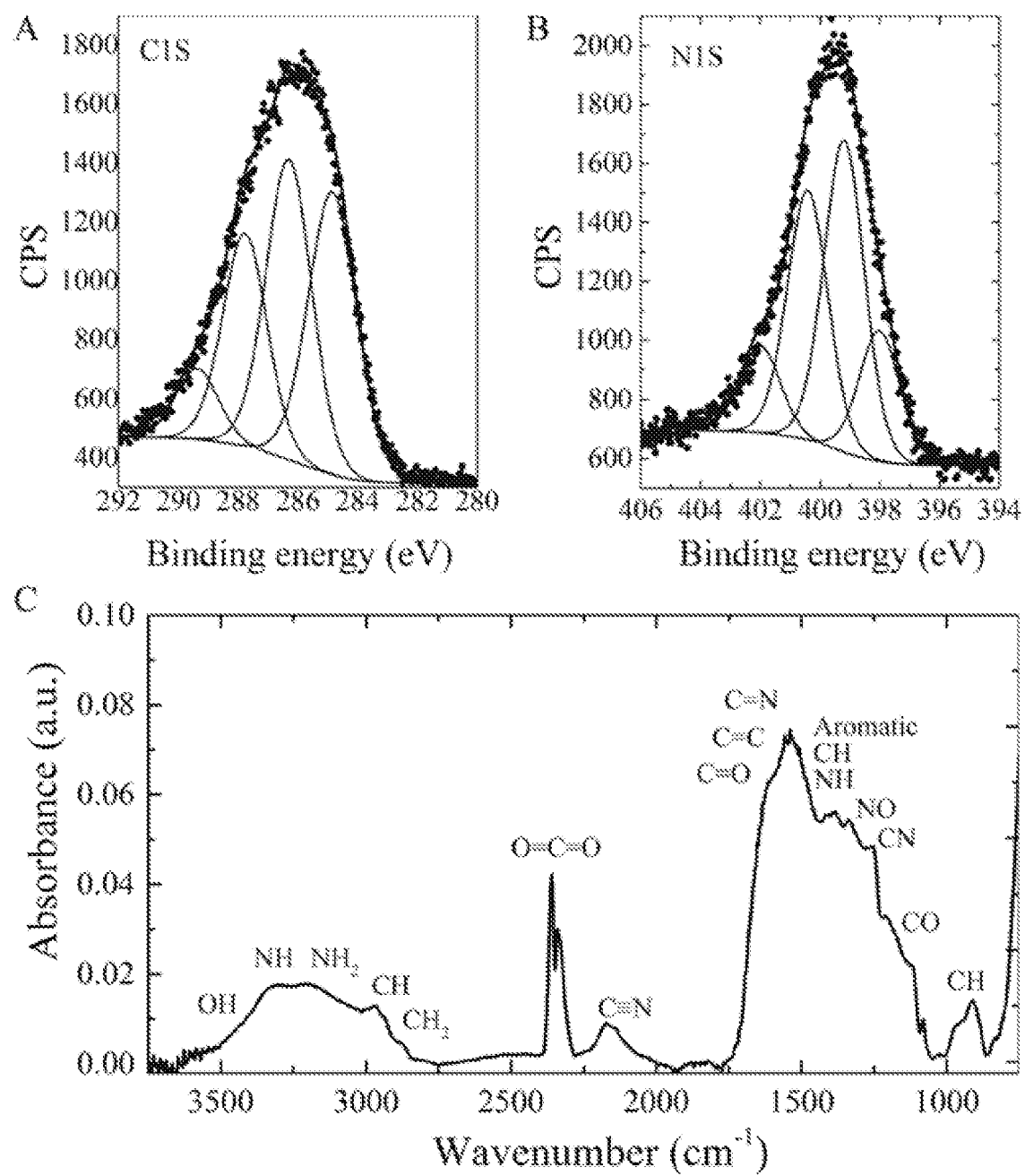
FIG. 11—Graphs showing: typical C1s (A) and N1s (B) peaks of nanoparticles fabricated when using an acetylene flow rate of 2 sccm and measured by XPS; and a FTIR spectrum of the nanoparticles (C).

Images A and B in FIG. 11 detail the high resolution XPS C1s and N1s core-levels with their corresponding deconvolutions, respectively. Four components can be assigned to the C1s peak located at 284.9 eV, 286.3 eV, 287.8 eV and 289.4 eV. The first peak corresponding to the lowest energy electron binding energy corresponds to pure carbon configurations in an amorphous network as well as C—H bonds, the second and third peaks correspond to different carbon hybridizations with nitrogen and oxygen atoms such as C—O, C=O, C—N, C=N and nitrile groups in various environments and the fourth peak to various COO compounds. The XPS N1s peak (FIG. 11B) can also be deconvoluted into 4 distinct components. The first peak is located at 398 eV and is assigned to nitrogen bonded to two carbon atoms, such as those found in pyridinic-N form compounds; or to $sp^3$ nitrogen atoms bonded to $sp^3$-hybridized carbon atoms. The second component with a peak centred at 399.2 eV is assigned to both nitriles and amine groups. The third peak centred at 400.4 eV is attributed to nitrogen trigonally bonded to three $sp^2$ carbon atoms, like in graphitic-N structures, or to nitrogen atoms bonded to two $sp^2$ and one $sp^3$ carbon atoms in an amorphous CN network. The fourth peak at 402.0 eV is attributed to nitric oxide compounds.

Fourier transform infrared spectroscopy measured in attenuated total reflectance mode (FTIR-ATR) confirms the results obtained by XPS. Image C in FIG. 11 shows a typical infrared spectrum obtained in the wavenumber range of 3750 $cm^{-1}$-750 $cm^{-1}$. The spectrum features two broad absorption bands located between 3600 $cm^{-1}$-2800 $cm^{-1}$ and 1750 $cm^{-1}$ and 1050 $cm^{-1}$. The first band is attributed to O—H (~3500 $cm^{-1}$), N—H (~3300 $cm^{-1}$ and ~3200 $cm^1$) and C—H (~2880 $cm^1$, ~2935 $cm^{-1}$ and ~2970 $cm^1$) stretching vibrations while the second and broader band is assigned to C=O (~1715 $cm^{-1}$), C=C (1640 $cm^{-1}$-1680 $cm^{-1}$), C=N (1640 $cm^{-1}$-1690 $cm^{-1}$) stretching vibrations as well as to N—H (~1500 $cm^{-1}$) and C—H (~1450 $cm^{-1}$ and ~1380 $cm^{-1}$) bending vibrations, C—C stretching vibrations in aromatic rings (~1450 $cm^{-1}$), and N—O (~1340 $cm^{-1}$), C—N (~1250 $cm^{-1}$) and C—O (1200 $cm^{-1}$-1000 $cm^{-1}$) stretching vibrations. The peak located at ~2170 $cm^{-1}$ is attributed to stretching vibrations of nitrile groups and the peak at ~900 $cm^{-1}$ to out-of-plane vibrations in unsaturated carbon assemblies.

The XPS and FTIR spectra measured for the nanoparticles resemble the spectra measured on carbon-based thin films deposited and grown on metallic substrates and prepared in similar process conditions. These thin films have been deposited on various implantable biomedical devices and are used to cloak the foreign material, enhancing the biocompatibility of the implants coated in this way. Furthermore, it was also shown that these films are capable of the covalent immobilisation of bioactive proteins and other biomolecules by means of embedded radicals.

Figure 12:
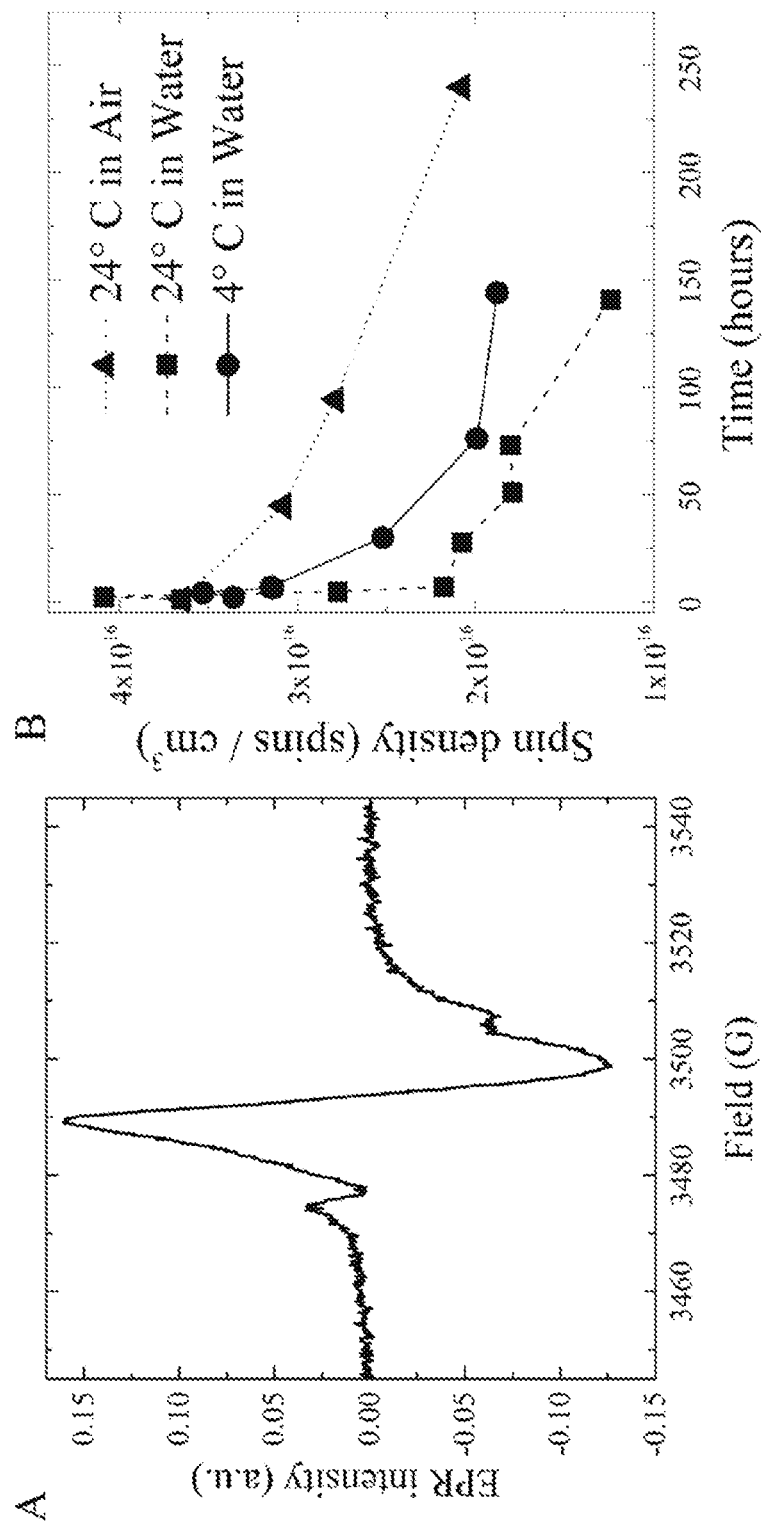
FIG. 12—EPR spectrum of nanoparticulate polymers and aggregates (A), and kinetics of the radicals in different media (B).

Particle growth is enhanced by the influx of ions, monomer radicals and functional groups formed in the plasma. Furthermore, the presence of CO, NO and OH groups indicates that atmospheric oxygen is reacting with active radicals as soon as the nanoparticles are removed from vacuum and exposed to the laboratory atmosphere. The Inventors hypothesise therefore the presence of unpaired electrons in the CN:H amorphous structure of the nanoparticles. FIG. 12 image A shows a typical EPR spectrum of nanoparticles fabricated when using an acetylene flow rate of 2 sccm. The broad resonance peak centred around 3495 G (g-factor of 2.004) confirms the presence of unpaired electrons (radicals) within the nanoparticles. FIG. 12 image B shows the radical kinetics of nanoparticles stored in different ambient conditions. Nanoparticles stored in water at 24° C. showed a 50% radical decay within the first 24 hours after being collected from the plasma. When stored in water but at 4° C. the same 50% radical decay was only observed after 150 hours. Results suggest a higher radical stability when nanoparticles are stored in air, even at ambient temperatures where the initial radical density was only halved after 240 hours of being collected from the plasma. Thus, the nanoparticles and aggregates disclosed herein are particularly suited to storage in a liquid.

Results suggest that the surface chemistry of aggregates can be transformed upon radical- and/or moiety-mediated reactions. Radical diffusion is temperature-activated and culminates in reactions with oxygen. Surface oxidation is triggered either by producing nanoparticles at higher base pressures in the plasma chamber or by exposure and subsequent storage of nanoparticles in air. The aggregate surface can be further functionalised by simple addition of $N_2$ in a $C_2H_2$/Ar plasma. Nitrogen is incorporated in the nanoparticles in the form of CN hybridizations, a radical molecule found in the plasma/gas phase, as well as in the form of surface amine functional groups.

The presence of unpaired electrons paves the way for using the nanoP$^3$ material as a versatile and biocompatible nanocarrier, by allowing a robust covalent conjugation with various biomolecules in an active form without needing to use chemical linker molecules and multistep wet chemistry to achieve the conjugation. This represents an important process simplification, reduced environmental impact and significant cost reductions in the commercial context. Interestingly, the unpaired electrons in nanoparticulate polymers and aggregates are an intrinsic source of angular momentum that can be explored in the context of magnetic resonance imaging (MRI) through hyperpolarization techniques. Hyperpolarisation exploits the highly spin-polarized unpaired electrons by transferring their angular momentum to specific nuclei, making the compound suitable to be used as an MRI contrast agent. Thus, the nanoP$^3$ material disclosed herein may be used as a contrast agent without further conjugation of any additional contrast agents thereto. Additionally, the versatility of the present production method by plasma discharges allows for the easy introduction of a variety of hydrocarbon precursors, which can be used to introduce further magnetic or other strategic elements into the nanoparticles, depending on the particular application.

In order to tailor the characteristics of the nanoparticulate polymers and aggregates, many variables can be changed and their effect on the resulting materials examined.

Figure 13:
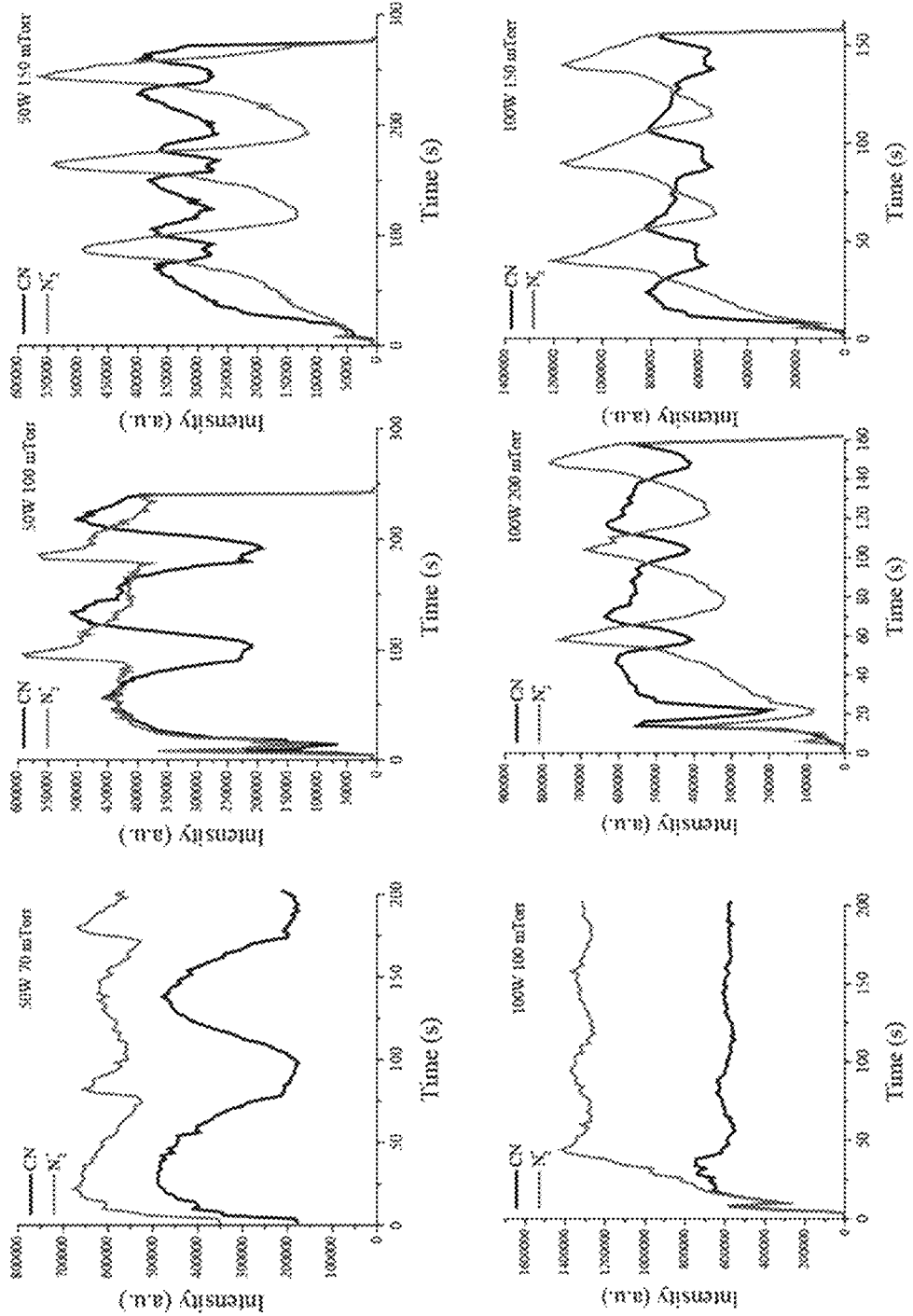
FIG. 13—Monitoring the temporal profile of the emission intensity associated with CN radical molecules and $N_2^+$ molecular ions during formation of products for various working pressures and power coupled to the plasma.
Figure 14:
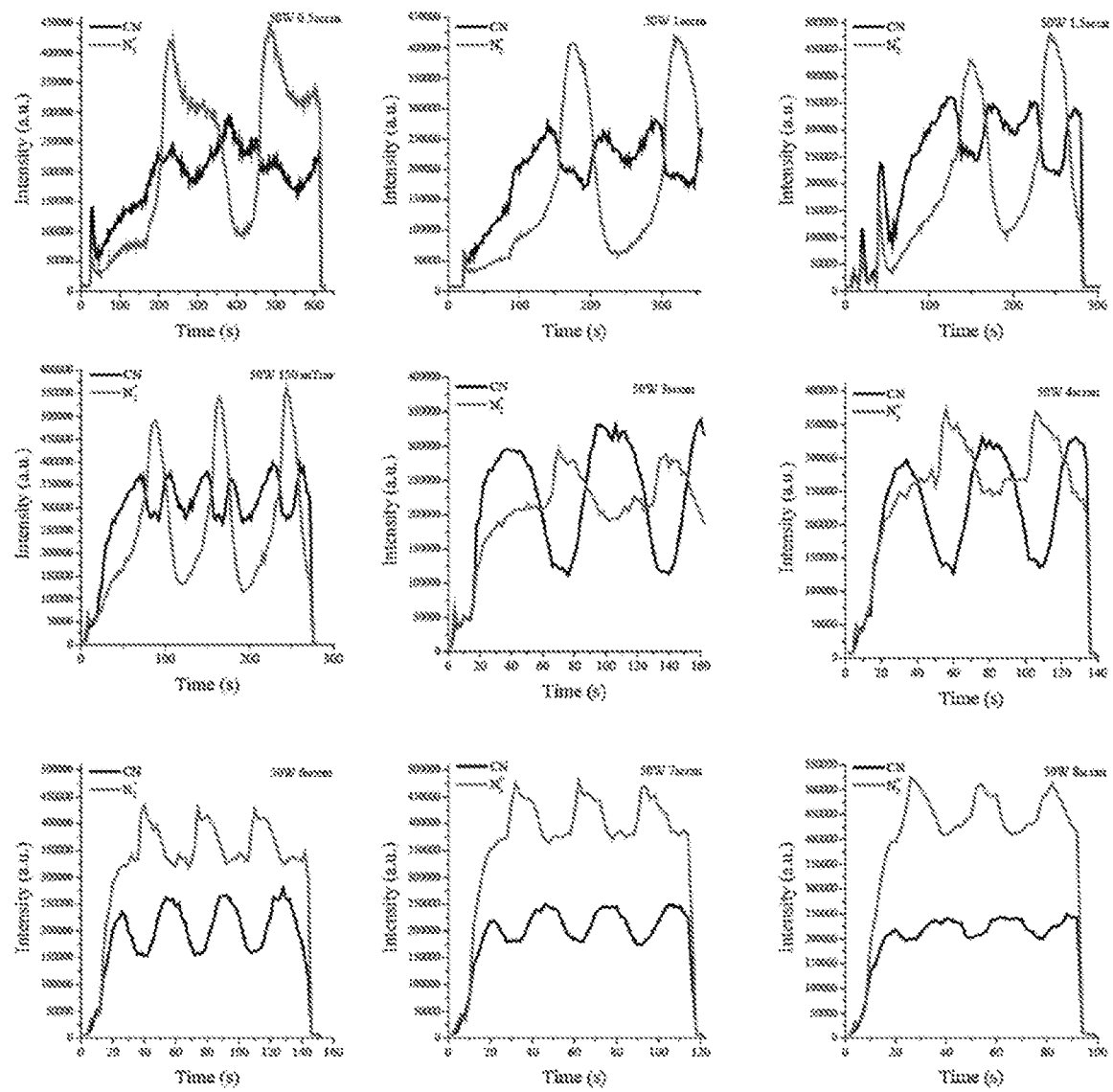
FIG. 14—Monitoring the temporal profile as in FIG. 13 but for various values of acetylene flow rates at a fixed 50 W coupled to the discharge.
Figure 15:
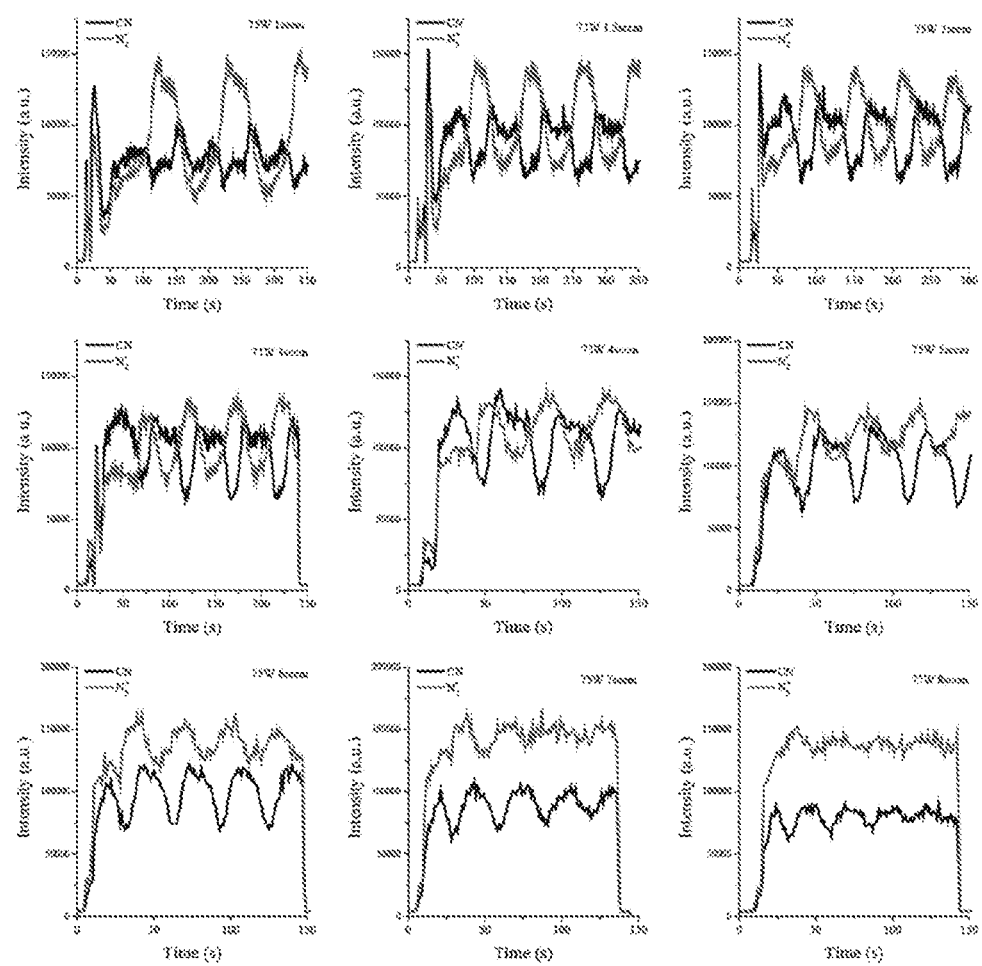
FIG. 15—Monitoring the temporal profile as in FIG. 14 but at a fixed 75 W coupled to the discharge.
Figure 16:
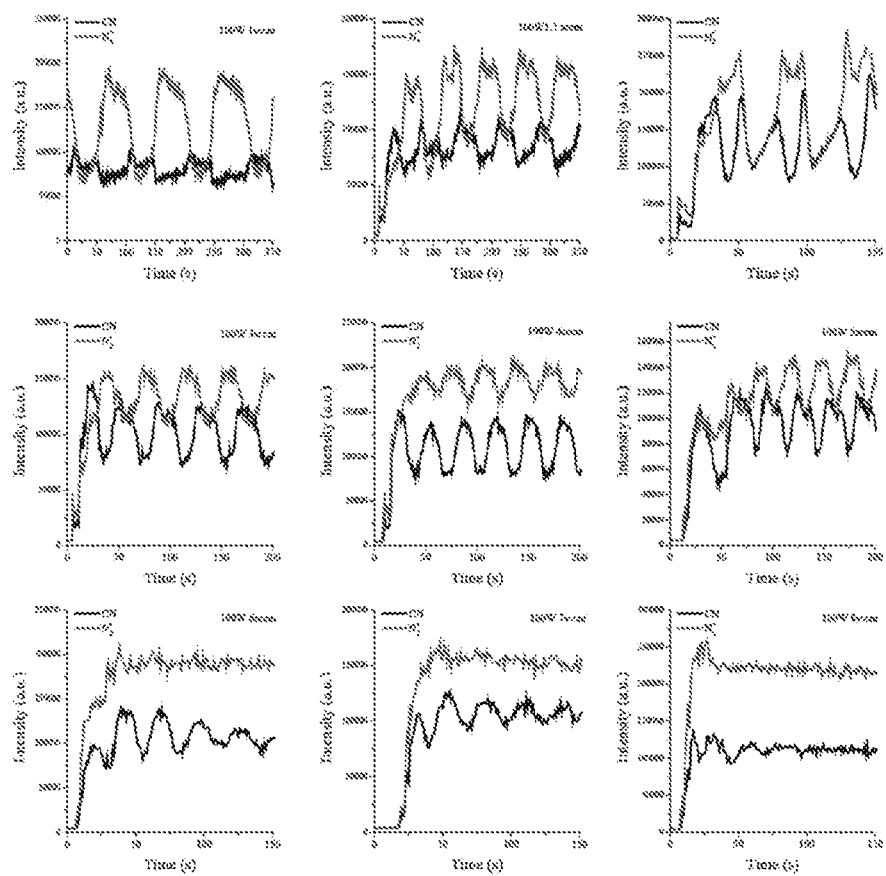
FIG. 16—Monitoring the temporal profile as in FIG. 14 but at a fixed 100 W coupled to the discharge.

In FIG. 13, the temporal profile of the emission intensity associated with CN radical molecules and $N_2^+$ molecular ions during nanoparticle formation for various working pressures and power coupled to the plasma is shown. All other parameters were fixed within this set of experiments. Aggregation occurred for the maximum emission intensity of $N_2^+$ molecular ions and minimum emission intensity of CN populations. Results suggest that CN radical molecules are further consumed during nanoparticle formation. Overall, the frequency of the oscillations increases with increasing power and pressure, indicating that nanoparticles are produced at a higher rate. Similar conditions were utilised in further tests but with: various values of acetylene flow rate (1-8 sccm) used, 150 mTorr and fixed flow rates for Ar and $N_2$ gases of 3 and 10 sccm, and at a fixed 50 W, 75 W or 100 W coupled to the discharge, sccm respectively (FIGS. 14, 15 and 16, respectively).

Figure 17:
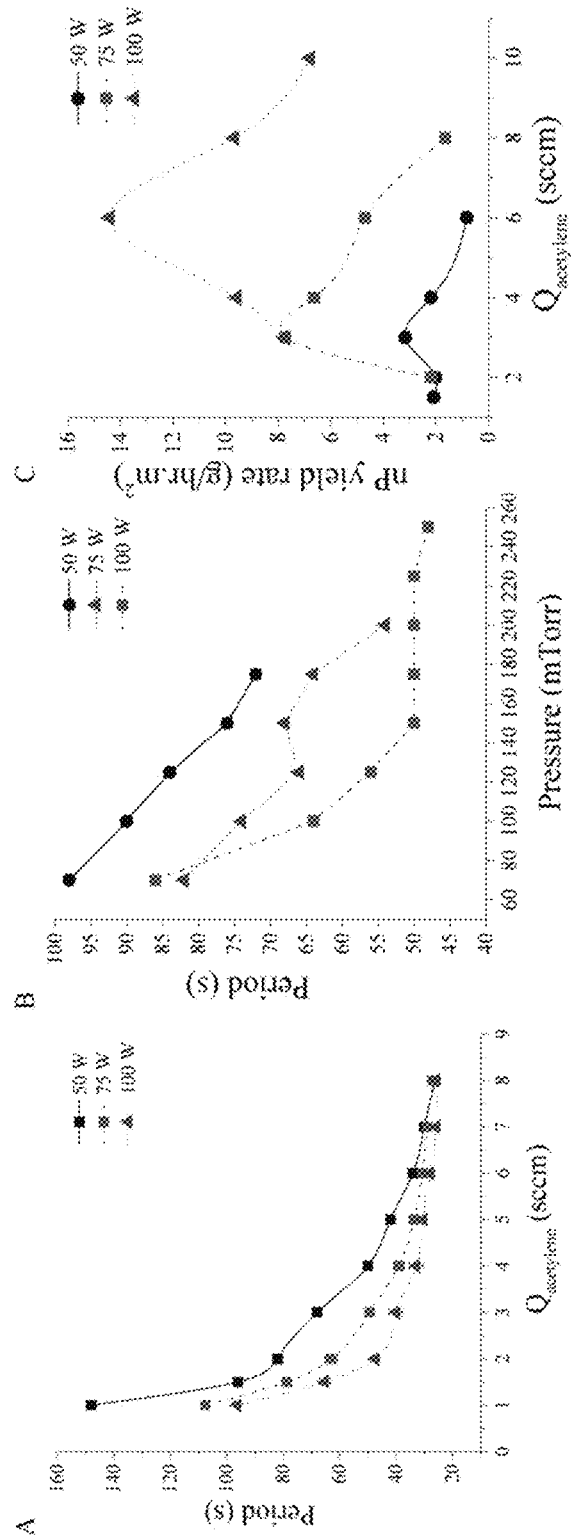
FIG. 17—Period of the oscillations (A and B) and nanoparticle yield rate (C) as a function of the acetylene flow rate and for 50, 75 and 100 W.

FIG. 17 shows the period of the oscillations as a function of the acetylene flow rate (image A) and pressure (image B) for a coupled radiofrequency power of 50, 75 and 100 W. All other plasma parameters were kept constant. The period for each synthesis run was calculated by averaging the time difference between 3 consecutive maxima of the emission intensity of the nitrogen molecular ions. At lower acetylene flow rates the period of the oscillations is highly modulated by the coupled power. Differences in the nanoparticle production rate are less significant with an increase of the monomer flow rate, showing that a further excess in monomer does not contribute to nanoparticle production.

Overall, results show that the relevant macroscopic parameter that describes nanoparticle production is ∝W/F, where W is the power coupled to the discharge and F is the monomer flow rate. Additionally, at higher monomer flow rates the residence time of precursor molecules in the plasma decreases, resulting also in lower fraction of fragmented monomer molecules. An increase in the gas drag force with increasing flow rate would also be responsible for rapid growth cycles as the particles are pushed out of the plasma more rapidly. The period of the oscillations can be further modulated by changing the pressure at which the discharge is maintained during nanoparticle synthesis. The nanoparticle yield rate is shown in FIG. 17 (image C) as a function of the monomer flow rate and if power coupled to the plasma. Overall, results show that the yield rate increases with applied if power, maximising at 14.4 g/hr m$^2$ for 100 W and 6 sccm. For all the studied if powers, the yield rate profile features a maximum before it decreases to smaller values at higher monomer flow rates. The decrease in the number of nanoparticles collected at higher monomer flow rates is related to a transition in the discharge where volume polymerisation is suppressed to surface polymerisation. A key parameter influencing this transition is the residence time of the monomers in the discharge volume. At flow rates below the maximum yield point there is sufficient energy per monomer to effectively fragment all monomers supplied and the increasing gas flow increases the number of available reactive fragments in the discharge volume. At flow rates beyond the maximum yield point however, the power is no longer sufficient for effective fragmentation hence the proportion of the population of fragments reactive enough to form nanoparticles in the volume of the discharge decreases and the presence of an increasing population of non-reactive fragments decreases the rate of particle formation in the volume.

Figure 18:
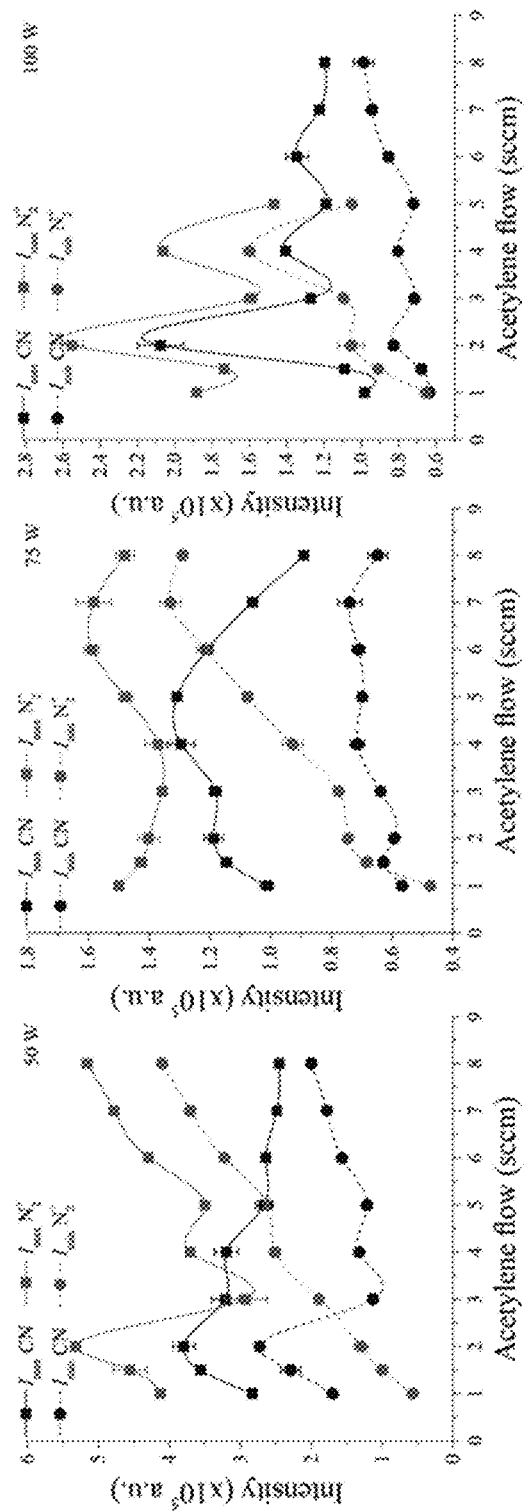
FIG. 18—Maximum and minimum emission intensities of CN radical molecules and $N_2^+$ molecular ions during nanoparticulate polymer and aggregate production within the 1-8 sccm monomer flow rate range at 50, 75 and 100 W.

FIG. 18 shows the maximum and minimum emission intensities of CN radical molecules and $N_2^+$ molecular ions during nanoparticle production within the 1-8 sccm monomer flow rate range at 50, 75 and 100 W. Overall the amplitude of the oscillations decreases with increasing flow rate.

Figure 19:
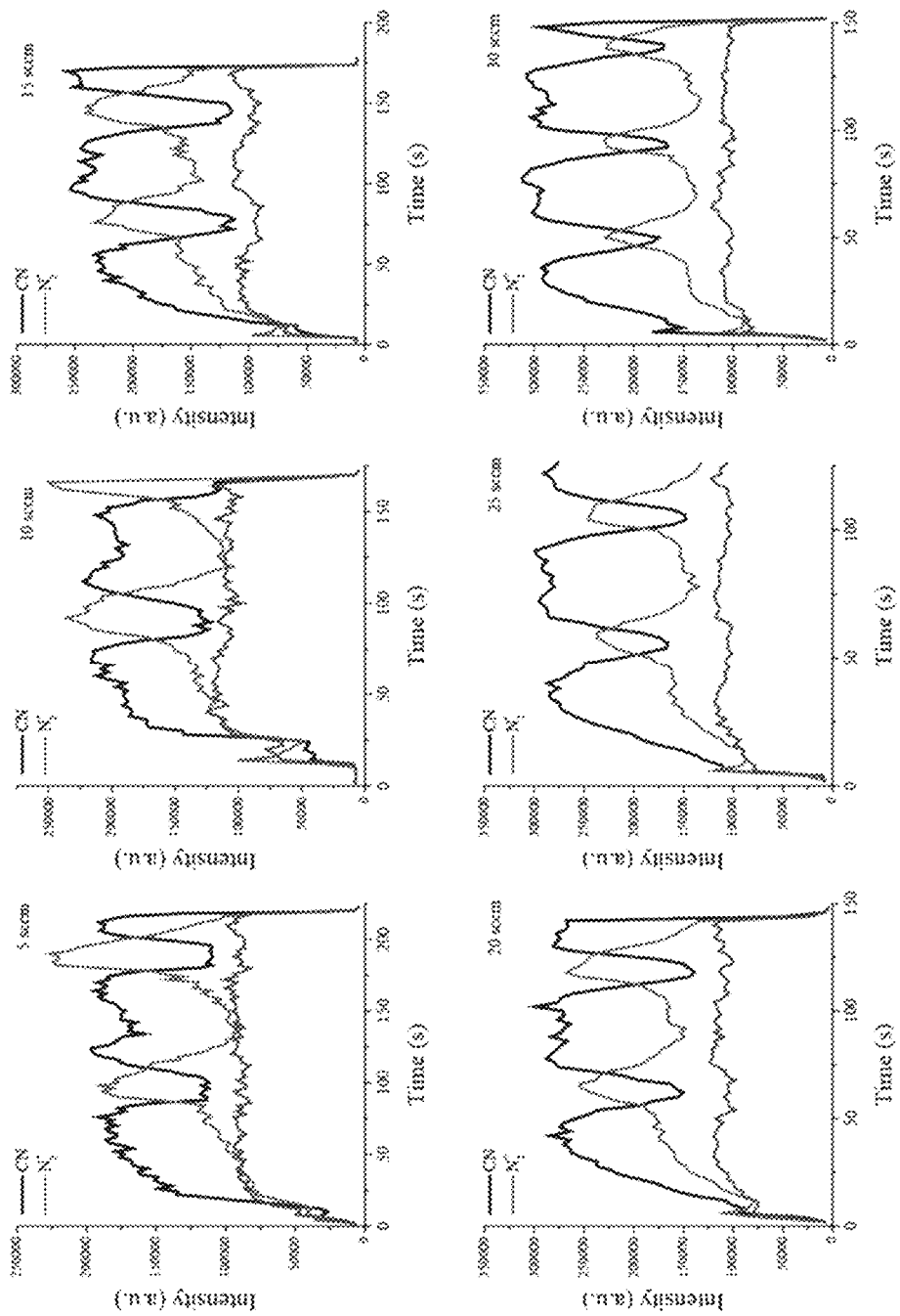
FIG. 19—Temporal profile of the emission intensity associated with CN radical molecules and $N_2^+$ molecular ions during nanoparticulate polymer and aggregate formation for various values of nitrogen flow rate.

FIG. 19 shows the temporal profile of the emission intensity associated with CN radical molecules and $N_2^+$ molecular ions during nanoparticle formation for various values of nitrogen flow rates. All other parameters were fixed within this set of experiments.

Figure 20:
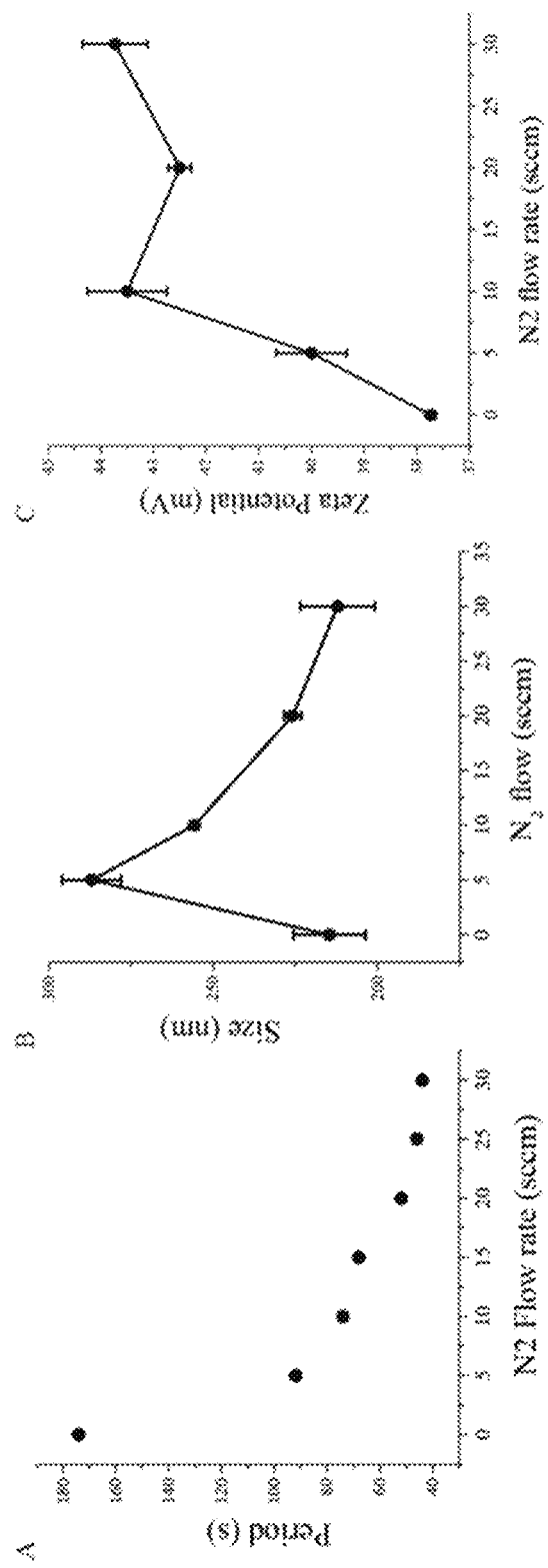
FIG. 20—Influence of $N_2$ in the oscillation period, size and zeta potential during nanoparticulate polymer and aggregate production.
Figure 22:
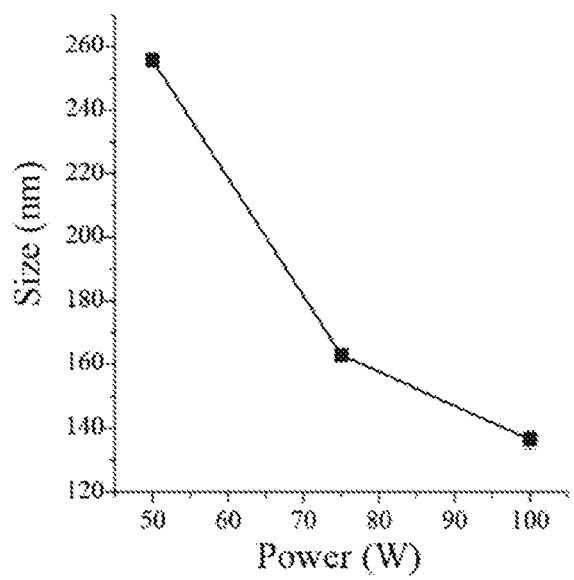
FIG. 22—Effect of coupled power to the discharge in the nanoparticle size (A) and yield rate (B).
Figure 22:
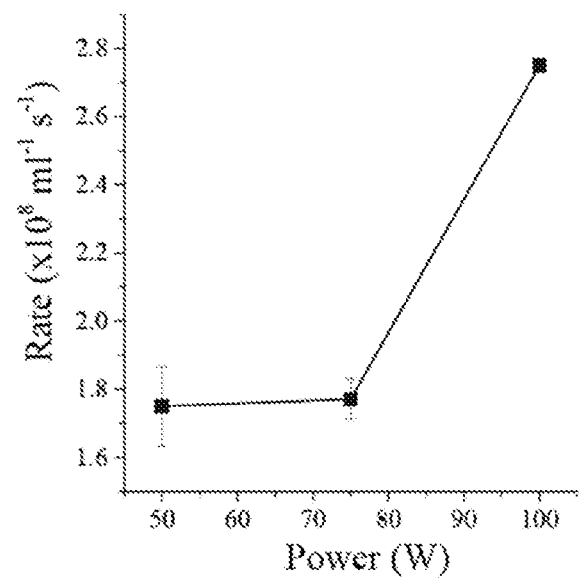
Figure 24:
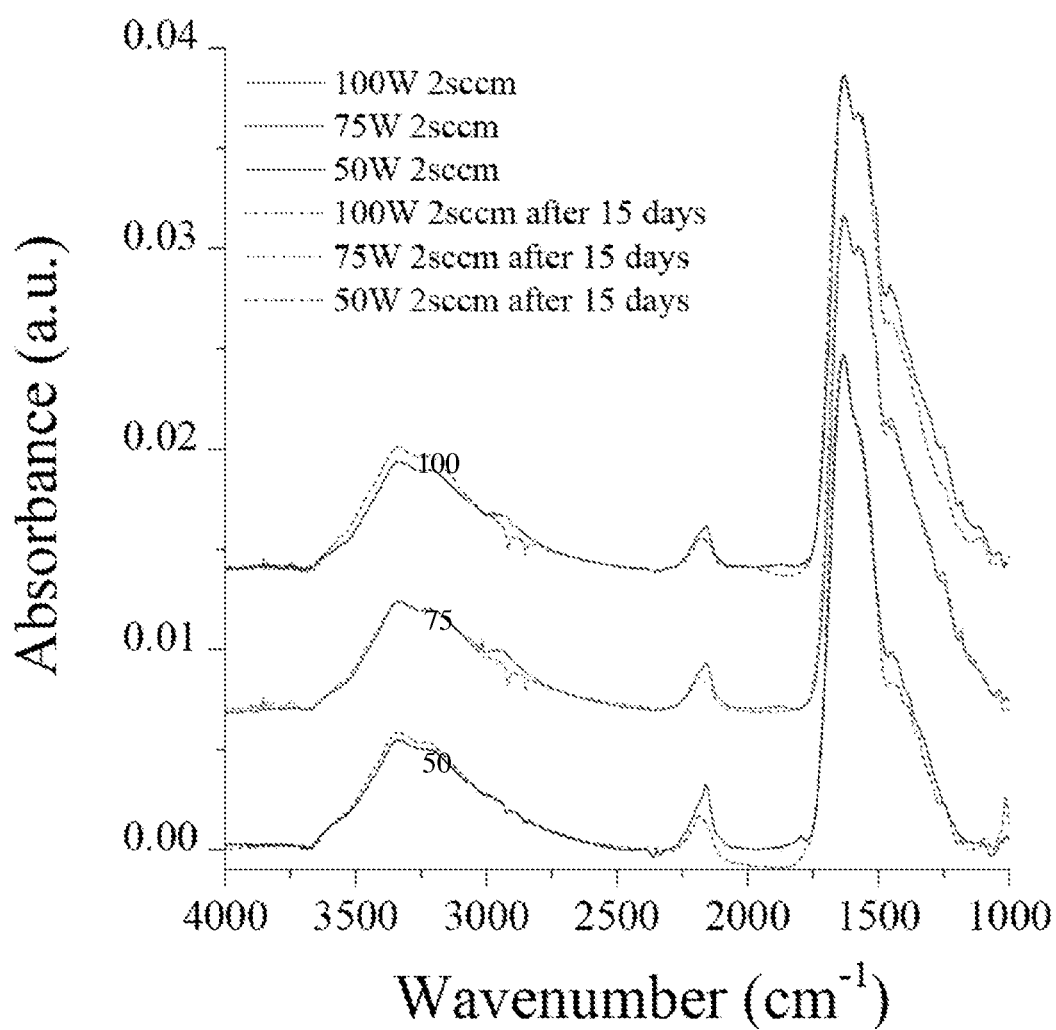
FIG. 24—FTIR measurements on nanoparticles at different storage times.

In FIG. 20, image A, shows the influence of $N_2$ in the oscillation period during nanoparticulate polymer and aggregate production. The period of the oscillations drops significantly with $N_2$ inclusion suggesting that CN radicals play an important role in nanoparticle growth. Image B shows nanoparticle size decreases with increasing nitrogen flow rate as a result of a higher gas drag force acting on the nanoparticles in the plasma reactor. Thus, the size of the nanoparticles and aggregates disclosed herein can be modulated by varying the flow rate of a carrier gas, such as nitrogen. Also, image C shows that the nanoparticle zeta potential increases with a higher nitrogen fraction in the plasma reactor. At higher nitrogen fractions, the overall nitrogen incorporated within the nanoparticle structure (either in the form of CN bonds or amine functional groups) increases. Positively charged amine surface functional groups (for example as shown in FIG. 24), should account for the increased zeta potential observed at higher nitrogen fractions. The effect of coupled power to the discharge in the nanoparticle size (top) and yield rate (bottom) is also shown in FIG. 22.

Figure 21:
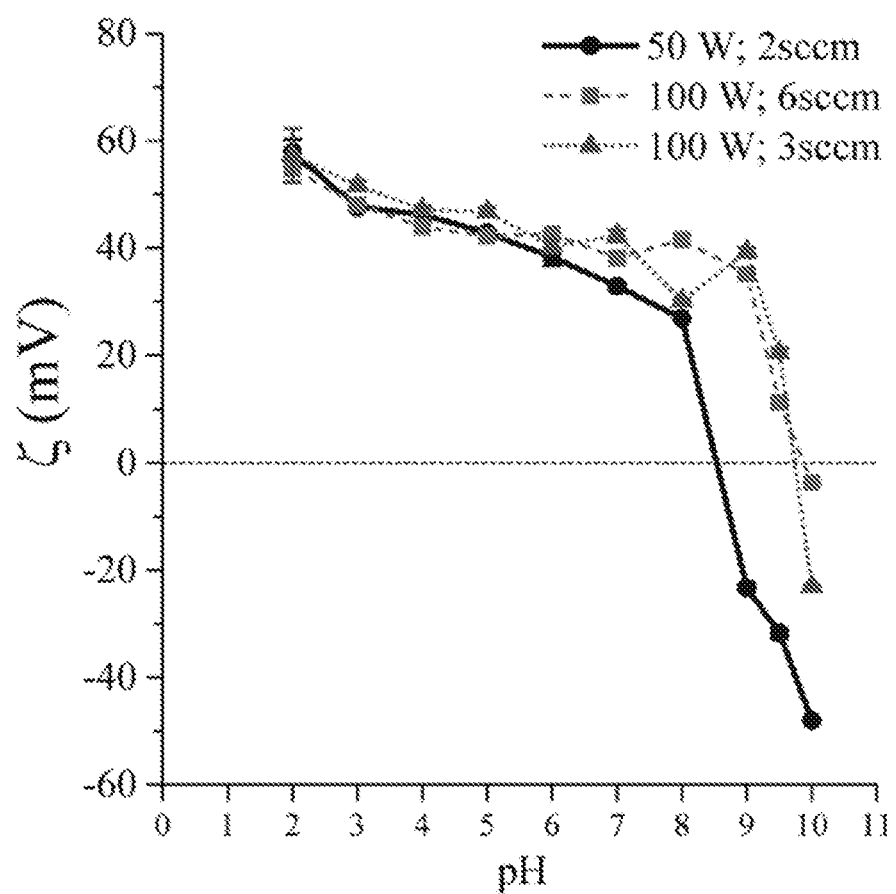
FIG. 21—Zeta potential of nanoP$^3$ particles as a function of pH of the solution containing the particles.

FIG. 21 shows the zeta potential of nanoP$^3$ particles as a function of pH of the solution comprising the particles. The results show that the charge surrounding the nanoP$^3$ material can be readily modulated by tailoring the concentration of positive and negative ions in the solution. This feature is particularly useful when making conjugates between the nanoP$^3$ material and highly charged second species or with strong dipole moments. The isoelectric point can also be tailored by making nanoP$^3$ material under different plasma parameters. Thus, the methods disclosed herein may comprise modulating the pH when conjugating a second species to a nanoparticle or aggregate as disclosed herein. The pH may be increased or decreased, depending on the charge of the second species to be conjugated.

Figure 23:
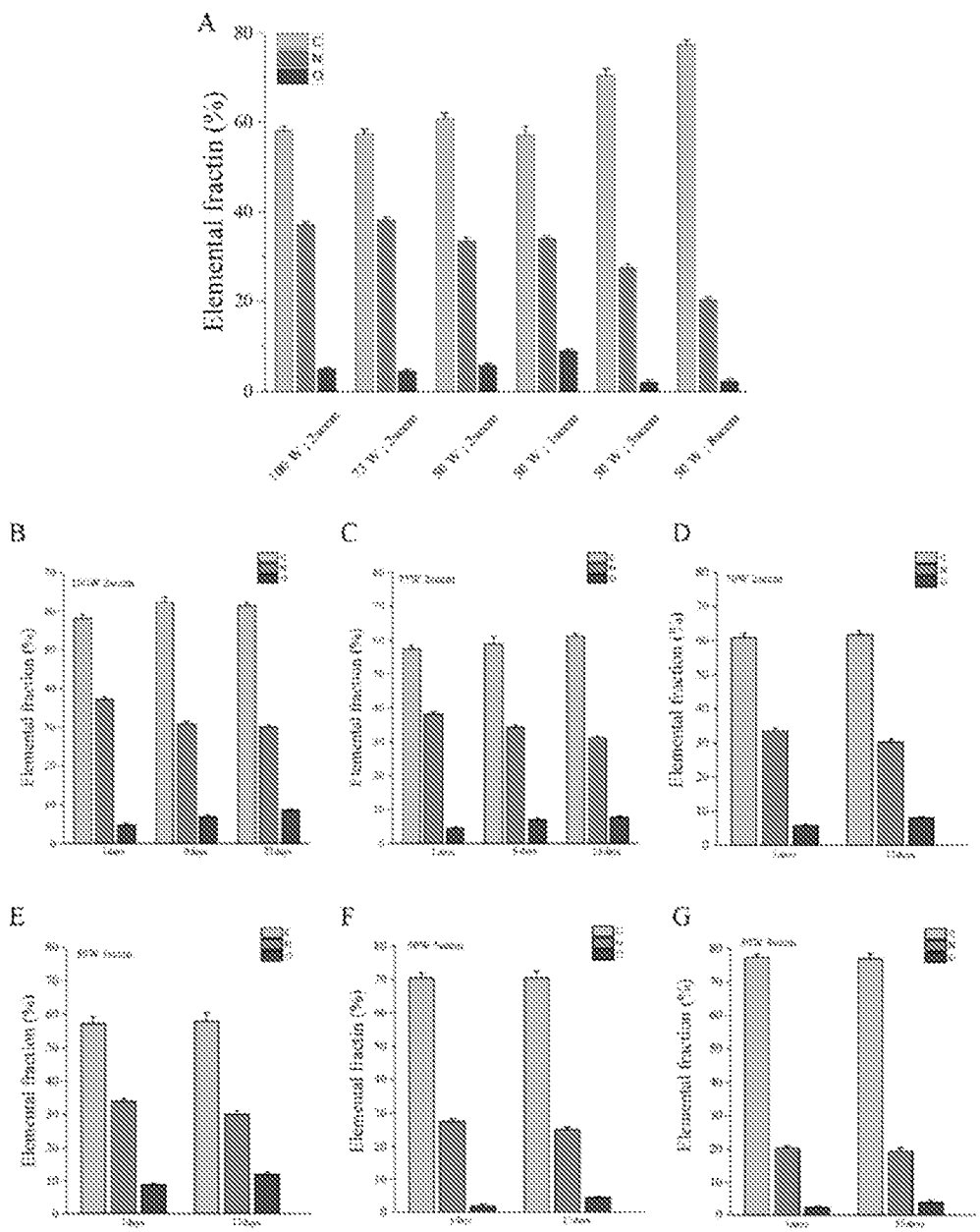
FIG. 23—Carbon, nitrogen and oxygen fractions on nanoparticles prepared with different coupled powers and monomer flow rates.

FIG. 23 shows carbon, nitrogen and oxygen fractions on nanoparticles prepared with different coupled powers and monomer flow rates. Image A shows nanoparticles prepared with 100 W and 75 W at a fixed acetylene flow rate (e.g., 2 sccm) have virtually the same elemental fraction. The results suggest that nanoparticles with the same chemical structure can be fabricated at different yield rates with a size variability range of 12.5% (FIG. 20). The results also show the carbon/nitrogen ratio within the nanoparticles increasing at higher monomer flow rates. Images B to G shows nanoparticle elemental fractions at different time periods following their synthesis. Overall, the results show a decrease in the nitrogen content with storage time (e.g., in FIG. 23 image C from a maximum 38.2% at day 1 to 34.2% at day 9) and an increase in the carbon an oxygen fraction, the latter due to surface oxidation (FIG. 25).

FIG. 24 displays FTIR measurements on nanoparticulate polymers and aggregates at different storage times, revealing that the nitrogen drop observed with XPS is mainly triggered by a decrease in nitrile (C≡N) bonds. The broad peak around 3250 cm$^{-1}$ indicates the presence of surface amine functional groups.

Figure 25:
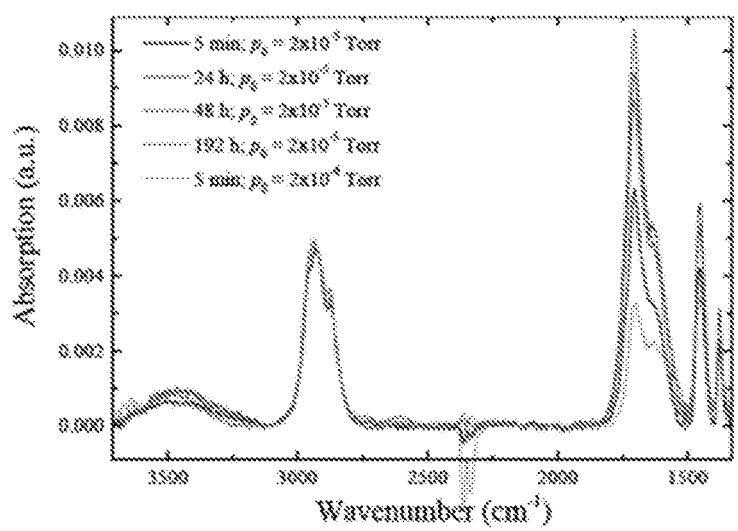
FIG. 25—FTIR measurements on nanoparticles made in acetylene and argon only discharges.

Further FTIR measurements on nanoparticles made in acetylene and argon only discharges (without nitrogen) are shown in FIG. 25. Measurements confirm a significant increase in CO bonds with storage time, also consistent with the decay in the nanoparticle radical density.

Example 2—Fluorescent Properties of nanoP$^3$

Figure 26:
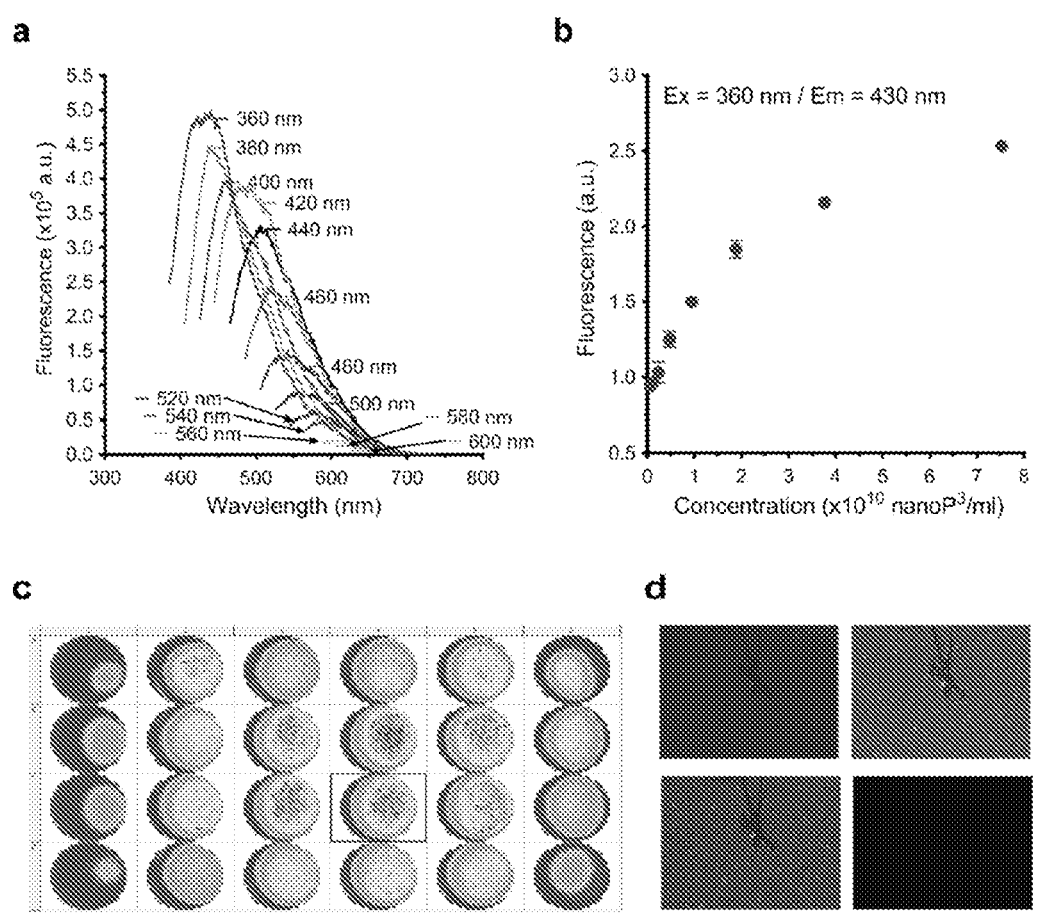
FIG. 26—NanoP$^3$ autofluoresce within the UV-VIS-NIR range.

Using steady-state emission spectroscopy, the Inventors found that nanoP$^3$ dispersed in aqueous solution (or cell media) are auto-fluorescent within the UV-VIS-NIR range. A microplate reader was used to measure the fluorescence emission/excitation spectra of both dry (as synthesized) and resuspended (PCR grade water or cell media) nanoP$^3$. FIG. 26 image A shows that the emission profiles depend on the excitation energy and FIG. 26 image B shows that intensity significantly increases with nanoP$^3$ concentration in solution. FIG. 26 image C shows the fluorescence distribution of as synthesized dry nanoP$^3$ in the well collector. The distribution of nanoP$^3$ in the wells was measured by scanning each well in mapping mode. A 30×30 matrix was used, resulting in a 900 point/well resolution. The excitation and emission monochromators were set to 360 and 430 nm respectively, gain to 2200 and the focal weight to 9 mm. FIG. 26 image D shows that the fluorescence properties of nanoP$^3$ were confirmed by confocal fluorescence microscopy measured in the blue, green, yellow and red channels. For this experiment, the synthesis parameters were set at Q=3, 10 and 3 sccm for acetylene, nitrogen and argon, working pressure of 150 mTorr and radiofrequency power of 50 W.

Example 3—Fluorescent Properties of nanoP$^3$ Part 2

Figure 27:
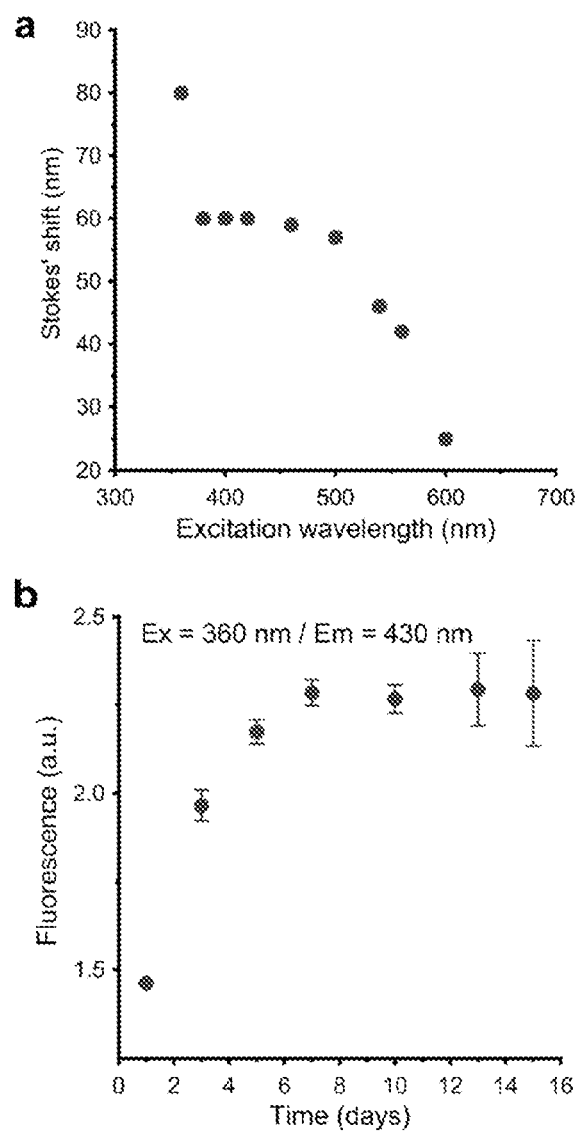
FIG. 27—Intensity of nanoP$^3$ fluorescence increases over time.

A microplate reader was used to measure the fluorescence emission/excitation spectra of both dry (as synthesized) and resuspended (PCR grade water or cell media) nanoP$^3$. FIG. 27 image A shows that the maximum Stoke's shift was 80 nm for an excitation wavelength of 360 nm, decreasing to 25 nm for an excitation at 600 nm. The Stoke's shift was calculated by subtracting the excitation wavelength to the corresponding emission wavelength. FIG. 27 image B shows that the intensity of the nanoP$^3$ fluorescence increases in solution over time, which correlated with a continuous surface oxidation driven by radical diffusion to the particle surface. For this experiment, the synthesis parameters were set at Q=3, 10 and 3 sccm for acetylene, nitrogen and argon, working pressure of 150 mTorr and radiofrequency power of 50 W.

Example 4—Quantification of Molecular Cargo Bound to nanoP$^3$

Figure 28:
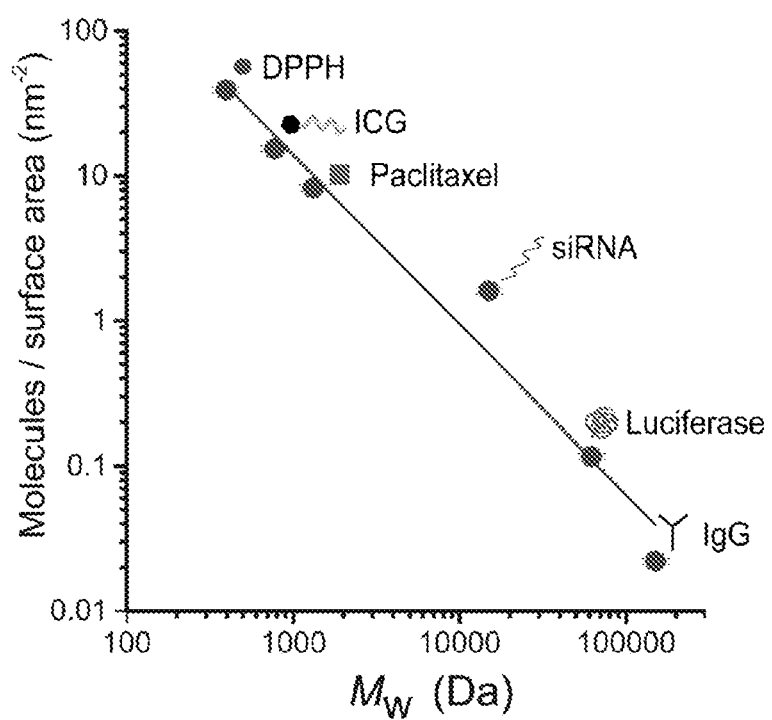
FIG. 28—Number of cargo molecules per unit surface area of nanoP$^3$ for various cargo molecular weights.

The nanoP$^3$ of the invention offer many advantages. One example of an advantage conferred by nanoP$^3$ is that the payload may be adapted or optimised by the number of aggregates used to carry the payload. The Inventors found that the total number of molecules bound to the nanoP$^3$ surface is ultimately dependent on the ratio between the nanoP$^3$ surface area and the molecular weight of the cargo (FIG. 28). The amount of molecular cargo bound to nanoP$^3$ following incubation was calculated using absorbance and/or fluorescence measurements of the nanoP$^3$-cargo samples and their corresponding washes (cargo=2,2-diphenyl-1-picrylhydrazyl (DPPH), indocyanine green (ICG), Paclitaxel-Oregon Green 488 (Paclitaxel), CY5-CPKKKRKV-NH2 and Goat anti-Rat IgG-Alexa647 (IgG)). Overall, the number of molecules bound to nanoP$^3$ decreased significantly with increasing molecular weight. For this experiment, the plasma parameters were set at Q=3, 10 and 3 sccm for acetylene, nitrogen and argon, 150 mTorr and 50 W. The incubation of nanoP$^3$ (10$^9$ nanoP$^3$/mL) with cargo was performed at room temperature, in RT-PCR grade water (pH=7) for 1 hour.

Example 5—Quantification of Molecular Cargo Bound to nanoP$^3$

Figure 29:
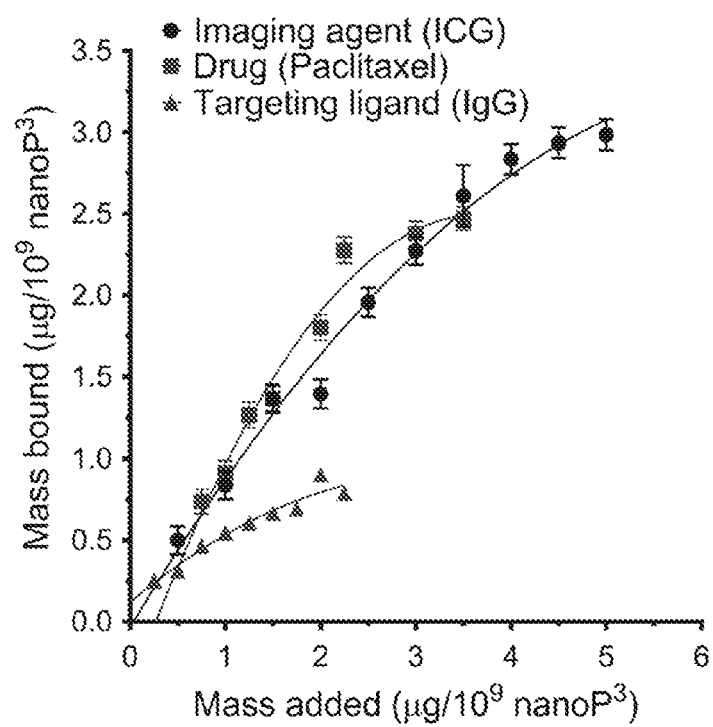
FIG. 29—The total cargo mass bound to nanoP$^3$ increases with the mass added to the solution during the incubation process.

FIG. 29 demonstrates that the amount of bound cargo increases with their concentration in solution. Exemplification with a drug (paclitaxel), imaging agent (indocyanine green; "ICG") and targeting ligand (IgG) demonstrated surface saturation at 2.3 μg, 2.9 μg and 0.8 μg respectively. For this experiment, the plasma parameters were set at Q=3, 10 and 3 sccm for acetylene, nitrogen and argon, 150 mTorr and 50 W. The incubation of nanoP$^3$ (10$^9$ nanoP$^3$/mL) with cargo was performed at room temperature, in RT-PCR grade water (pH=7) for 1 hour.

Example 6—Binding Kinetics of nanoP$^3$

Figure 30:
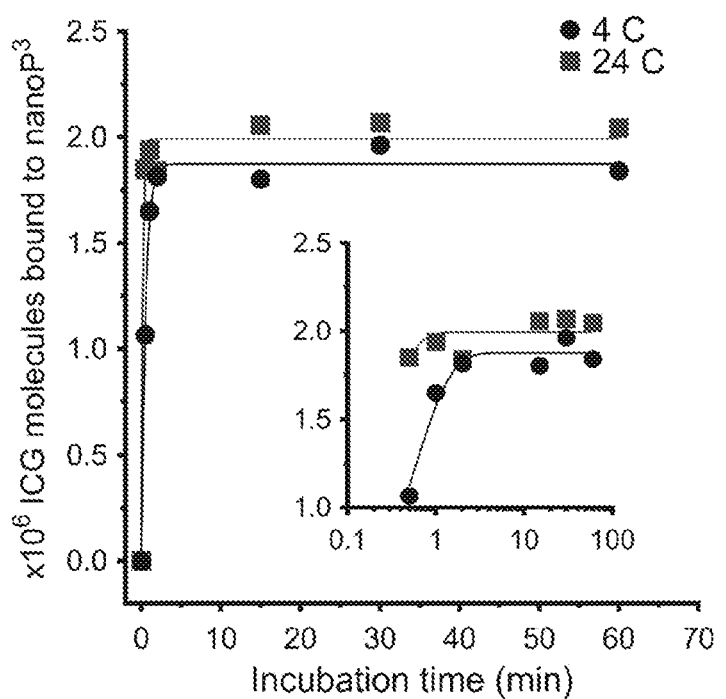
FIG. 30—Binding kinetics experiments using indocyanine green (ICG).

The binding kinetics associated with the simple nanoP$^3$ conjugation process can be assessed by measuring the amount of bound cargo at different incubation time points and temperatures. NanoP³ material was conjugated with the precise amount of indocyanine green (ICG) which was calculated in Example 5 to saturate the nanoparticle surface at a monolayer, i.e. $1.9 \times 10^6$ ICG molecules on a single nanoP³ particle (99 nm radius). FIG. 30 demonstrates that 90% of the total cargo was immobilized on the surface of nanoP³ within the first 30 seconds after incubation at 24° C., while incubation at lower temperature (4° C.) resulted in a 60% binding for the same time point. For both conditions, surface saturation was achieved in less than 5 minutes after incubation. For this experiment, the plasma parameters were set at Q=3, 10 and 3 sccm for acetylene, nitrogen and argon, 150 mTorr and 50 W. The incubation of nanoP³ ($10^9$ nanoP³/mL) with ICG was performed at room temperature, in RT-PCR grade water (pH=7) for 1 hour.

Example 7—Shelf-Life of nanoP³

Figure 31:
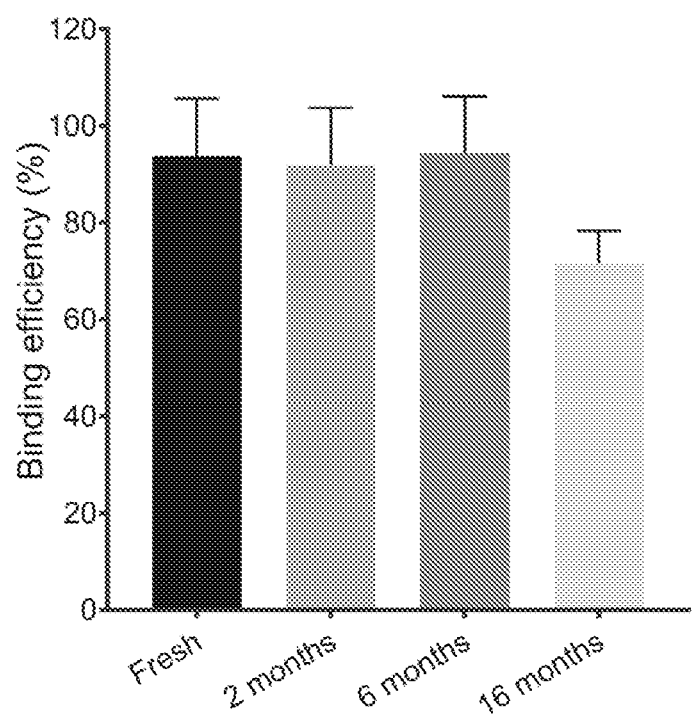
FIG. 31—Shelf-life of nanoP$^3$ exemplified with ICG.

A long shelf-life and easy path to functionalisation are necessary requirements for a nanoparticle platform to be applicable for clinical use. NanoP³ provides a cost and time effective nanoparticle platform that does not require linker chemistry or long incubation periods. The binding efficiency of nanoP³ stored for long periods of time was measured using indocyanine green (ICG) as a template molecule. FIG. 31 demonstrates that the ability of nanoP³ to immobilize cargo remains virtually constant during the first 6 months of storage in air at room temperature (FIG. 31). For samples stored up to 16 months, a decrease of 28% (non-significant) in the binding efficiency was observed. However, it was still possible to fully saturate the surface of nanoP³ by increasing the concentration of ICG in solution. Extended shelf-life could potentially be achieved by employing alternative storage approaches, including low temperature, vacuum or another non-reactive environment. The plasma parameters were set at Q=3, 10 and 3 sccm for acetylene, nitrogen and argon, 150 mTorr and 50 W. The incubation of nanoP³ ($10^9$nanoP³/mL) with ICG was performed at room temperature, in RT-PCR grade water (pH=7) for 1 hour.

Example 8—Cargo Bound to nanoP³ Retains its Activity

Indocyanine green (ICG) is a fluorescent dye with emission and excitation wavelengths at 805 and 830 nm respectively. Due to the low absorbance properties of tissue in this spectral window, ICG is widely used in the clinic for medical diagnostics. However, ICG is characterized by a short half-life circulation in vivo.

Figure 32:
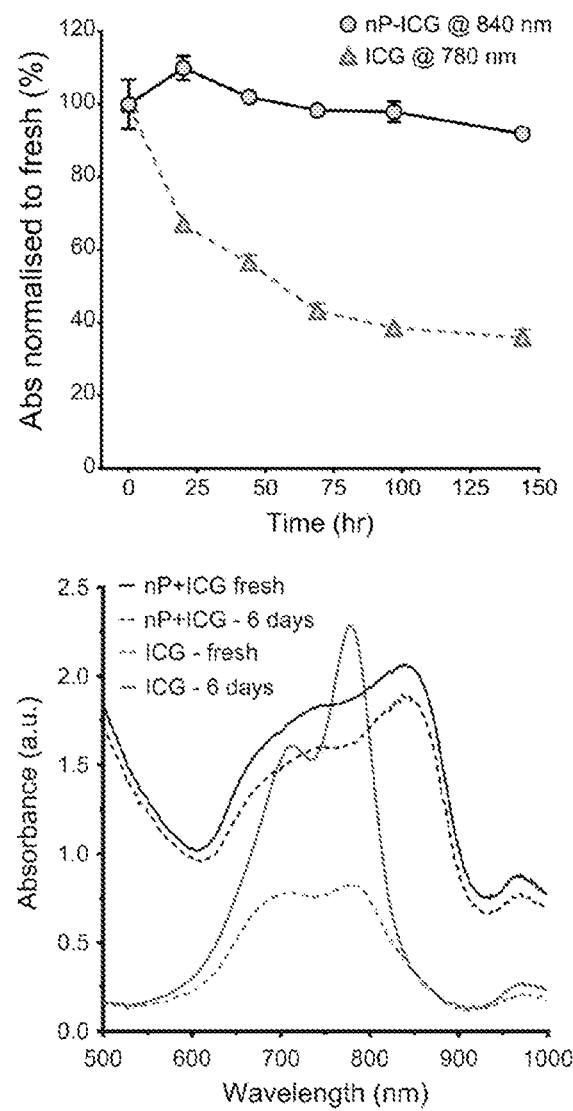
FIG. 32—Kinetics of free indocyanine green (ICG) and ICG bound nanoP$^3$.

FIG. 32 shows that ICG retains its activity for a significantly longer period in aqueous solution if bound to nanoP³. The binding of ICG to the nanoP³ surface was confirmed by a 60 nm red-shift of the absorbance peak from 780 nm to 840 nm compared with free ICG in solution. The VIS/NIR profile of free ICG and ICG conjugated nanoP³ confirmed that degradation of small cargo (<1000 Da) is significantly delayed once immobilized to nanoP³. The plasma parameters were set at Q=3, 10 and 3 sccm for acetylene, nitrogen and argon, 150 mTorr and 50 W. The incubation of nanoP³ ($10^9$nanoP³/mL) with ICG was performed at room temperature, in RT-PCR grade water (pH=7) for 1 hour.

Example 9—Binding of Cargo to nanoP³ May be Modulated by Altering pH

The binding of nanoP³ to a highly-charged cargo was also investigated, using a positively charged peptide sequence bound to a Cy-5 fluorescent tag for detection (Cy-5-CPKKKRKV-NH2).

Figure 33:
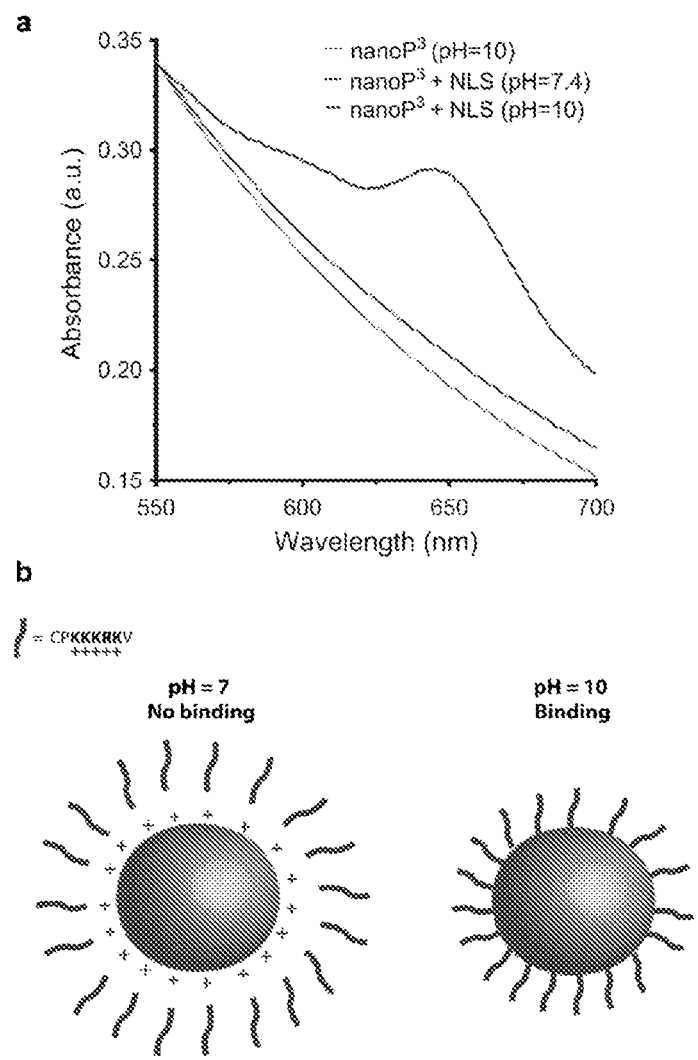
FIG. 33—Binding ability of nanoP$^3$ may be modulated by altering pH.

This peptide sequence is often used as a nuclear localization sequence capable of targeting the cell nucleus. This nuclear targeting ability is mostly driven by the presence of multiple polar (cationic) amino acids, including lysine (K) and arginine (R). FIG. 33 shows that initial incubation of nanoP³ with the peptide at neutral pH did not result in the expected robust conjugation observed for more neutral cargo. Increasing solution pH to 10 was required for binding to the highly positively charged peptide. As pH increases, the surface groups of the nanoparticles are progressively deprotonated and at pH >8, when the solution transitions to highly alkaline media, the particles reach their isoelectric point and then become progressively negatively charged. In such conditions, the peptide is attracted to the surface of nanoP³ and subsequently immobilized upon physical contact. When the pH of the solution containing the bound peptide was returned to neutral, the peptide remained bound. These results generally demonstrate that manipulation of solution pH can be used to enhance the binding of charged ligands and potentially orient them on the surface should they have a dipole moment.

Example 10—Aggregation and Solubility of the Nanoparticulate Polymers

Nanoparticulate polymer aggregation was tested in phosphate buffer (PB) at different pH as follows.

Nanoparticulate material was collected from the particle collector under sterile conditions in the tissue culture hood with filtered PB (0.2 μM syringe filter) in different pH, ranging from pH 2.5 to pH 12. Control nanoparticulate material was collected using filtered water. Using Flow Cytometry (Beckman-Coulter FACSVerse) samples were analysed for 3 minutes, or until a total number of 10,000 events was reached. Aggregation of the nanoparticulate polymers was quantified by gating appropriate fields against a separately validated sample of non-aggregated nanoparticulate polymer, via an observation of forward and sidelight scatter. Each measurement was normalised to 100% total population of nanoparticles.

Figure 34:
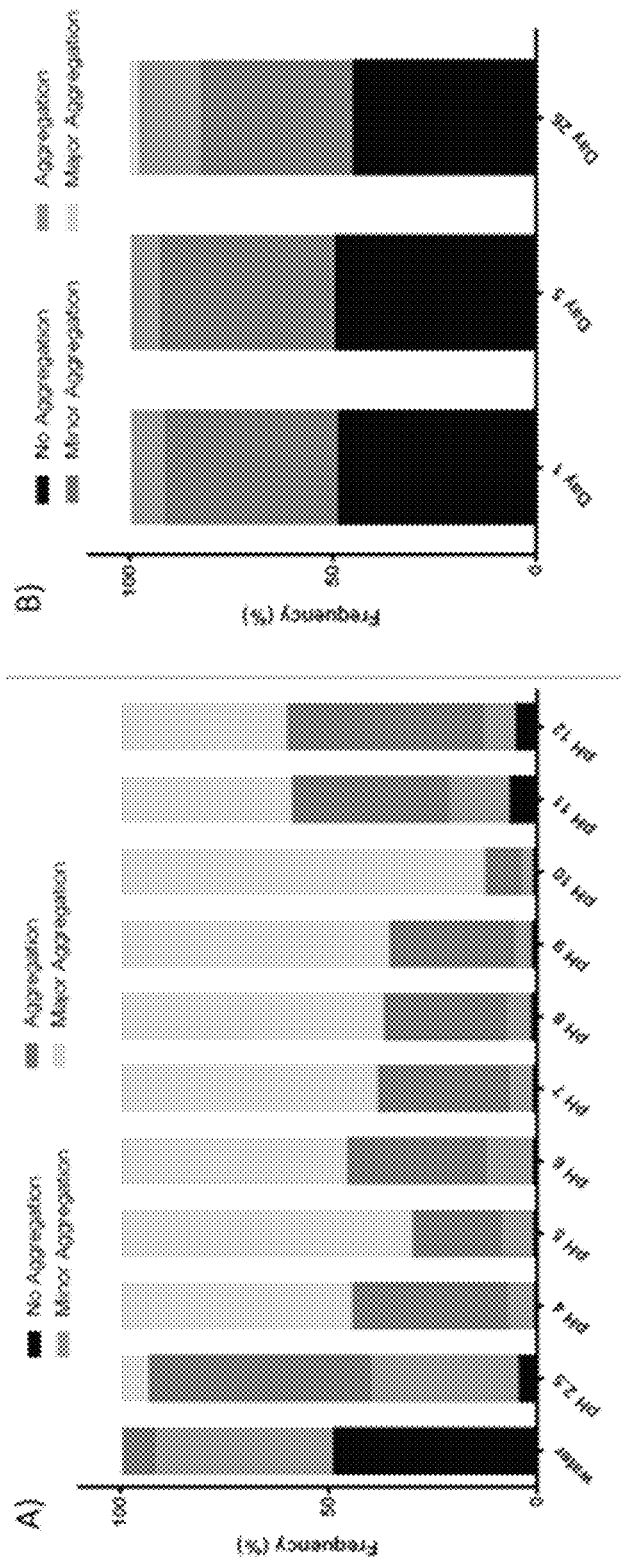
FIG. 34—Aggregation behaviour of aggregated nanoparticulate polymers in different media.

Nanoparticle solubility and dissolution was tested in water and various buffers at different pH values ranging from pH 2.5 to pH 12. Analysis was performed via flow cytometry where populations of 'no aggregation' to 'major aggregation' were gated based on a separately confirmed monodisperse population of nanoparticles resuspended in 10% SDS in water. Analysis of the different nanoparticle suspensions revealed that water was the optimal solution for monodispersity of the nanoparticles (FIG. 34, image A). All salt containing solutions tested showed significantly more aggregation, with good monodispersity observed at pH 2.5 (FIG. 34, image A). Without wishing to be bound by theory, the specific mechanism driving this behaviour is likely to be due to the charge of the nanoparticles and their interaction with the ionic salts in the buffered solutions. Analysis into the stability of the nanoparticles once in solution was also performed.

Results of the nanoparticulate material in water show a monodisperse population of nanoparticles even after 26 days in solution (FIG. 34, image B).

Example 11—Cytotoxicity Studies

In an initial study cytotoxicity was evaluated for 3 different cell types:
1) human Coronary Artery Endothelial cells (hCAEC, passage 4, Cell Applications, 300-05a);

2) human Coronary Artery Smooth Muscle cells (hCASMC, passage 5, Cell Applications, 350-05a); and;
3) Breast cancer cells (MCF7, passage 15, Sigma-Aldrich, 86012803).

Approximately 5,000 cells/cm$^2$ were counted and seeded in a flat-bottomed 96 well culture plate and incubated for 24 hours at 37° C. in a 5% CO$_2$ incubator. After 24 hours, serial dilutions of nanoparticulate polymers, from 5 million particles/well to 9,766 particles/well were then added into the medium, with n=5 replicates for each concentration of nanoparticulate polymer. After 72 hours of incubation, the cytotoxicity evaluation was performed using MTS cell proliferation and cytotoxicity assay kit (Promega, G3580). The MTS reagent was added to each well as per manufacturer's instructions and was further incubated for 2 hours. The formazan dye produced by viable cells was quantified via measuring the absorbance at 490 nm. Untreated cells (no nanoP$^3$) and cells treated with Rapamycin (100 nM, Sigma-Aldrich, R8781) were used as controls.

Figure 35:
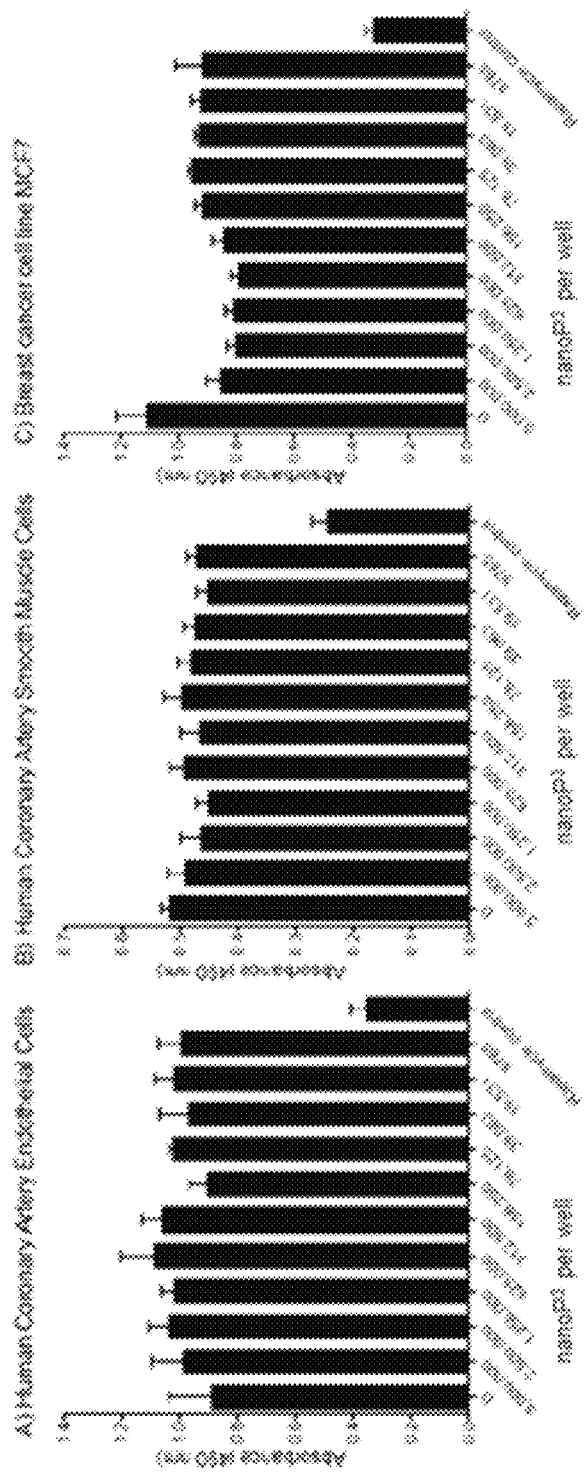
FIG. 35—Cell cytotoxicity in the presence of serially diluted nanoparticulate polymers and aggregates.

FIG. 35 shows the results for cell cytotoxicity studies in the presence of serially diluted nanoparticulate polymers and aggregates in the presence of the: human coronary artery endothelial cells (image A); human coronary artery smooth muscle cells (image B); and breast cancer cell line MCF-7 (image C).

Human coronary artery endothelial cells showed no significant reduction in viability, even in the presence of 5 million nanoparticles per well, relative to cell controls containing no particles. This was mirrored in results for human coronary artery smooth muscle cells. For breast cancer cell line MCF-7, all concentrations of nanoP$^3$ moderately reduced overall cell viability, but not to the extent of the rapamycin positive control.

Example 12—Conjugation Studies Part 1

Figure 36:
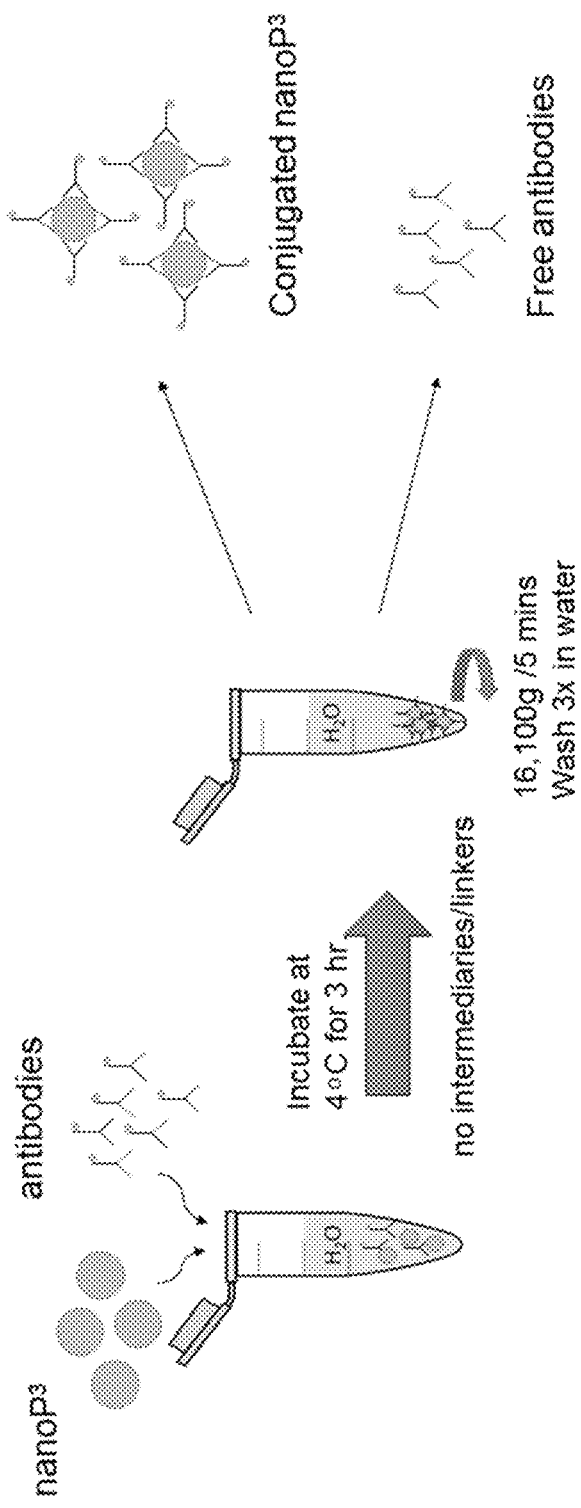
FIG. 36—Schematic illustration of single functionalisation of nanoP$^3$ with an antibodies.
Figure 37:
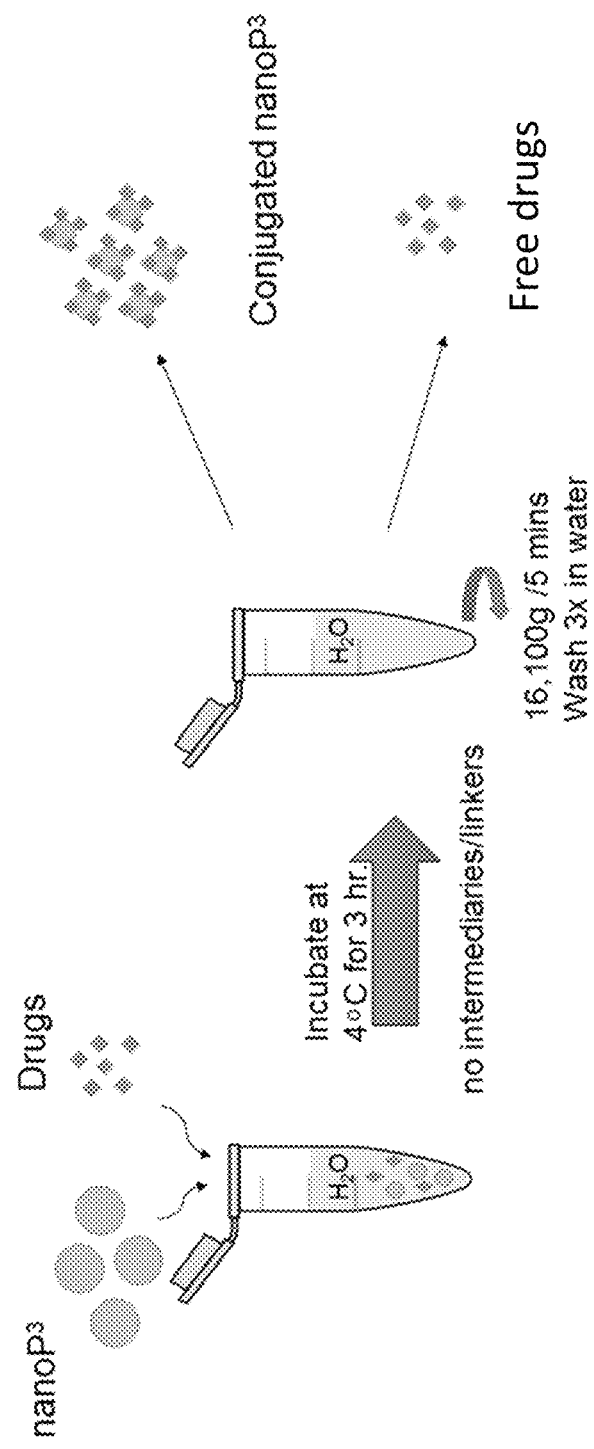
FIG. 37—Schematic illustration of single functionalisation of nanoP$^3$ with a drug.
Figure 38:
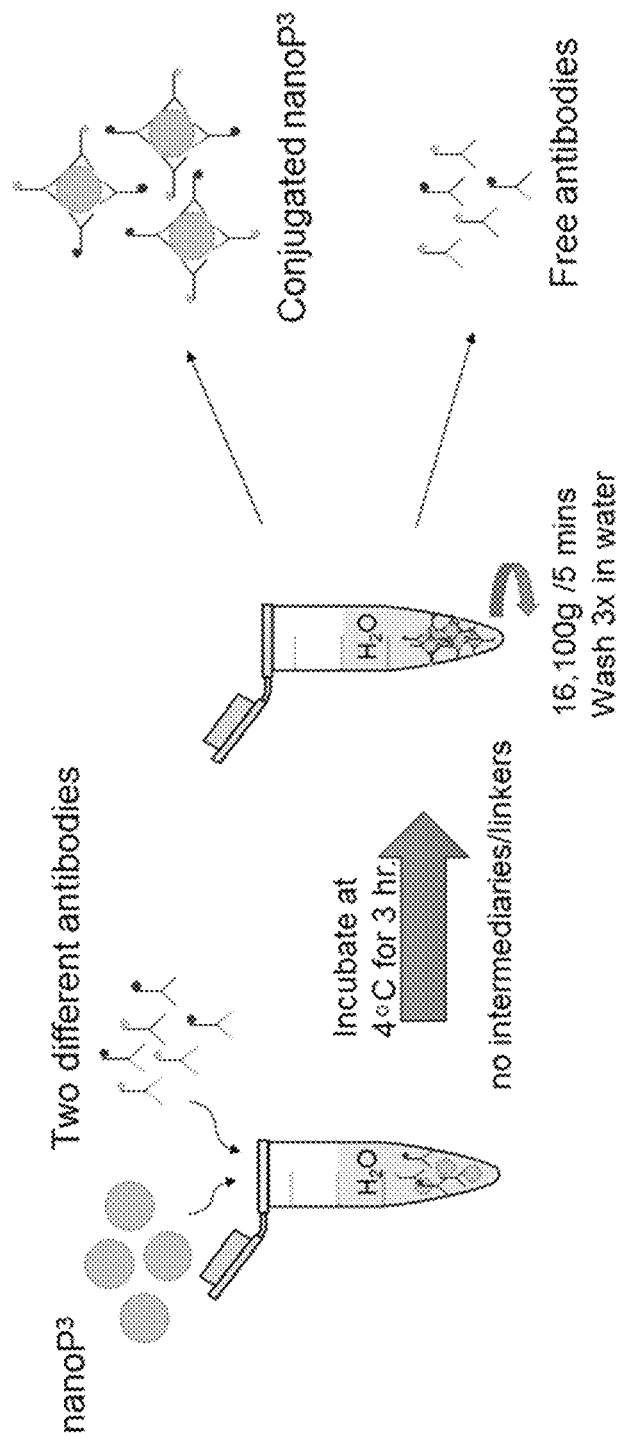
FIG. 38—Schematic diagram illustrates double functionalisation of nanoP$^3$ with an antibody and a drug.

FIG. 36 shows a schematic illustration of single functionalisation of nanoP$^3$ with an antibody. FIG. 37 shows a schematic illustration of single functionalisation of nanoP$^3$ with a drug. FIG. 38 outlines a schematic representation of functionalisation of nanoP$^3$ with an antibody and a drug.

Inter alia, the inventors have successfully covalently bound fluorescently-tagged (e.g., Alexa488, Alexa 594, Cy5, Cy7) and metal-tagged antibodies (e.g., gold and silver) to the nanoP$^3$ disclosed herein.

Conjugation of the nanoP$^3$ to secondary antibodies, drugs and/or proteins was evaluated using the following procedure:

NanoP$^3$ was collected from the nanoparticle collector under sterile conditions in a tissue culture hood with RT-PCR Grade water. The concentration of nanoparticles was measured by NanoSight LM10. Nanoparticles were then conjugated to desired antibodies (Goat anti-Rat IgG-Cy5; abcam ab6565; and Goat anti-Rabbit IgG; abcam ab150089 at 1:100 dilution), drugs (Doxorubicin: Sigma-Aldrich, D1515 at 100 µg/ml and Paclitaxel-Oregon Green 488, Invitrogen P22310 at 5 µg/mL) or proteins (Peroxidase from Horseradish; Sigma-Aldrich HRP; P6782 at 0.5 µg/mL) for up to 16 hours at 4° C., protected from light. Conjugation of HRP to 150 nm gold nanoparticles was performed (Cytodiagnostics; G-150) in an identical fashion. The samples were gently agitated using Bio RS-24 mini-rotator. After incubation, the test samples and appropriate controls were washed equally 5 times via centrifugation at 16,000 g, 5 minutes for the first 4 washes and a 15-minute wash on the 5th wash. The fluorescent intensity was measured using a plate reader, the Ex/Em were set in accordance to the fluorescent dye tag on each antibody or drug. For example, Alexa 488 and Oregon Green488, Ex/Em is at 494/517, whereas Cy5 Ex/Em is at 650/667 nm. Ex/Em of doxorubicin is at 470/585. For detection of HRP, conjugated nanoparticles and respective controls were incubated with ABTS (Sigma-Aldrich; A1888) and hydrogen peroxide (Merck; 386790) until colour was visible and measured at 405 nm.

Preliminary tests were performed to evaluate cell behaviour when in contact with the nanoparticles. Secondary FITC conjugated antibody was incubated with nanoparticles for 2 hours to allow for conjugation. Following a thorough washing of the antibody-conjugated nanoparticles in water, this material was added to a monolayer of endothelial cells (hCAEC), smooth muscle cells, monocytes (J774A) and lung cancer cells (LLC) and left to incubate for 24 hours. Images were taken at 5 minute intervals on a live cell imaging apparatus in bright field for cell morphology, and green fluorescence filters for detection of nanoparticles. The results indicated clear uptake of the nanoparticles by all cell types within the first 2 hours of the experiment. After uptake of the fluorescently labelled nanoparticles, the cells remained active for the whole 24 hours of the experiment, without demonstrating any obvious signs of stress or toxicity, as previously confirmed in our cytotoxicity study. Furthermore, cells readily divided despite the large amount of nanoparticles contained around the cell nucleus and in the cell cytoplasm. Chromosome condensation and separation, cytokinesis and subsequent re-attachment of the cells to the tissue culture plate were all unimpeded, indicating the benign nature of the nanoparticles with the cell types tested.

Figure 39:
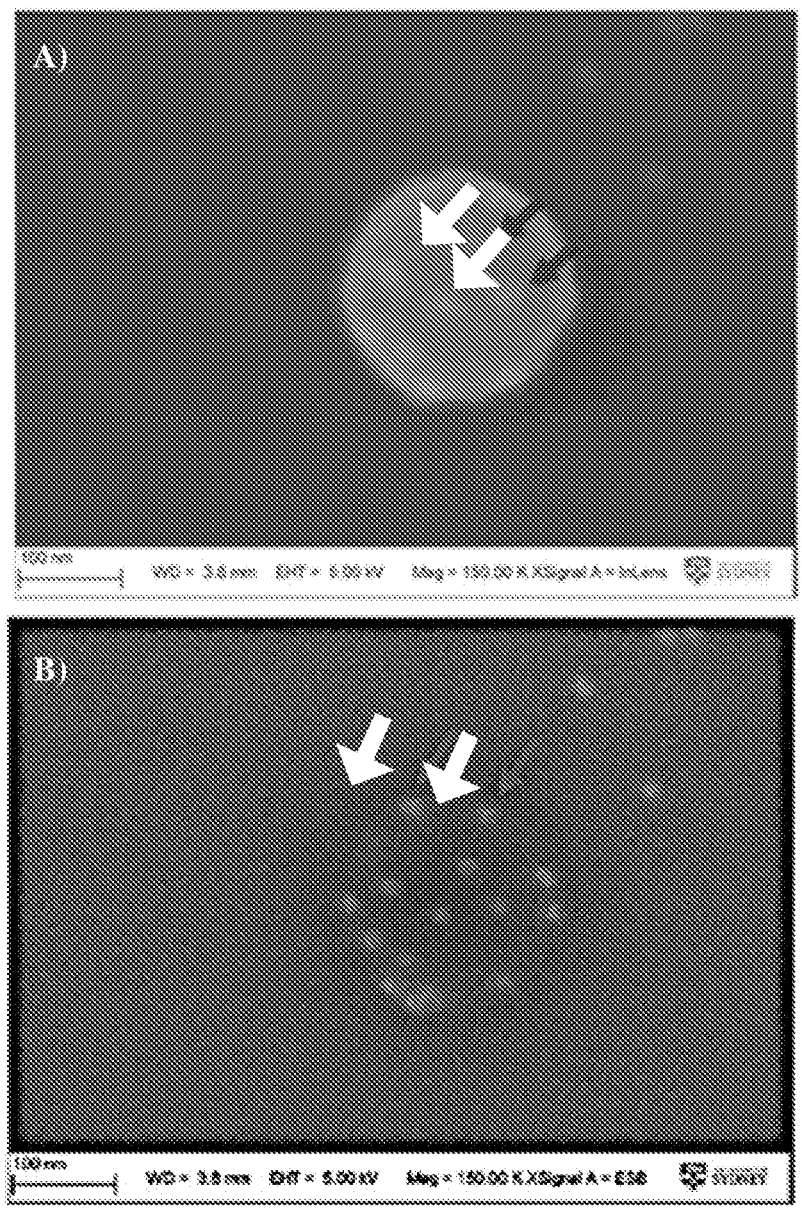
FIG. 39—Scanning electron microscopy images of nanoparticulate polymers incubated with gold tagged IgG antibodies in secondary electron (A) and backscattering modes (B).

FIG. 39 shows scanning electron microscopy images of nanoparticulate polymers incubated with gold tagged IgG antibodies and imaged using scanning electron microscopy. In the images, the largest circle in each is the nanoparticulate material, while the antibodies are much smaller (arrows) shown with secondary electron (image A) and backscattered electron (image B) modes.

Example 13—Conjugation Studies Part 2

Methods and Materials
Actin Staining

After fixation, the cell types listed in Example 11 were permeabilized with 0.1% x-triton 100 in PBS for 5 minutes. The samples were then washed 3 times in PBS. Cells were then incubated in Actin Red 555 ReadyProbes reagent (Life technologies, R37112) for 30 minutes, a dilution of 20 µl of the reagent to 500 µl of PBS.

DAPI Staining

After fixation, cells were incubated with DAPI Solution (1:1000 dilution in PBS, SAPBIO, NBP2-34422R) for 5 minutes at room temperature. The samples were washed 3 times in PBS prior to mounting with an aqueous fluorescent-shield mounting medium. After coverslipping, the images were taken within 24 hours under a fluorescent microscope.

Conjugation of Nanoparticles to Doxorubicin to Calculate the Fluorescent Quenching Nanoparticles were collected from the particle collector under sterile conditions in the tissue culture hood with RT-PCR grade water. For the nanoparticle control with no doxorubicin, equal volumes of water were added to the wells as a substitution for doxorubicin. Similarly, in the doxorubicin control wells, water was added as a substitution for nanoparticles. When nanoparticles were added to the well containing doxorubicin at 50 µg/mL (Sigma-Aldrich, D1515), the time course measurements were initiated immediately via plate reader (Ex/Em: 470/585) every 30 seconds starting from 0 mins to 5 minutes. The loss of fluorescence of doxorubicin was calculated against time 0.

MCF7 cells were seeded at 8,000 cells/cm² on a 96 well-plate a day prior to the experiment. 24 hours after seeding, the doxorubicin conjugated nanoparticle (prepared as previously described) were added into the wells and further incubated for another 24 hours. The viability of the cells was measured using MTS cell proliferation assay kit (Promega; G3580). The MTS reagent was added to each well as per manufacturer's instructions and was further incubated for 2 hours. The formazan dye produced by viable cells was quantified via measuring the absorbance at 490 nm. Untreated cells and cells treated with doxorubicin non-wash were used as controls.

Results

The experiments confirmed that the nanoparticles penetrate the cell wall in all cell types tested, without the need for cell penetrating agents. Furthermore, non-conjugated nanoparticles at concentrations up to 15 million nanoparticles/mL were shown to be non-toxic to endothelial cells and smooth muscle cells, whilst being mildly inhibitory to the proliferation of breast cancer cells.

In order to evaluate the drug conjugation capacity of nanoparticles, incubation with two commonly used chemotherapeutic drugs, paclitaxel and doxorubicin was performed. The ability of nanoparticles to conjugate to antibodies was also tested. The conjugation to antibodies represents an important facet for both therapeutic applications as well as particle tracking and imaging.

For conjugation with paclitaxel, nanoparticles were left to incubate with fluorescently labelled paclitaxel overnight at 4° C. After washing of the nanoparticles to ensure removal of all free paclitaxel, the particles were added to the supernatant of breast cancer cells. After 24-hour incubation, cells were fixed and counterstained with phalloidin for visualisation of the cell cytoskeleton. Interestingly, this experiment highlights that the particles are auto-fluorescent in the green channel, in the absence of any conjugates.

In a separate experiment, Cy5 secondary antibody was conjugated to nanoparticles and added to a monolayer of breast cancer cells (MCF-7) for 24 hours.

MCF7 cells were seeded at a density between 5,000 to 8,000 cells/cm² on Lab-Tek glass chamber slides suitable (Lab-Tek, 154534, and 155380) for cell culture for images. 24 hours after cell-seeding, test nanoparticles samples and controls were incubated with MCF7 and further incubated for another 24 hours. The cells were then fixed with 3.7% paraformaldehyde for 10 minutes at room temperature. The samples were then washed 3 times with PBS prior to the cell staining.

Cells were subsequently fixed and counterstained with DAPI for visualisation of the cell nuclei to observe the distribution of nanoparticles within the cells. The distribution appears to be uniform within the cytoplasm, however slightly more concentrated around the cell nuclei. There are no nanoparticles visible in the nucleus. The Cy5 antibody control shows no fluorescence anywhere within the cell, confirming the need for nanoparticle conjugation to enable its cell penetration. This experiment was repeated with lyophilised nanoP³ and Cy5 antibody, and results similarly show a ready uptake of the Cy5 conjugated nanoparticles. This experiment shows the potential for long-term storage of the nanoparticles alone or after conjugation with a bioactive molecule by means of lyophilisation.

Figure 41:
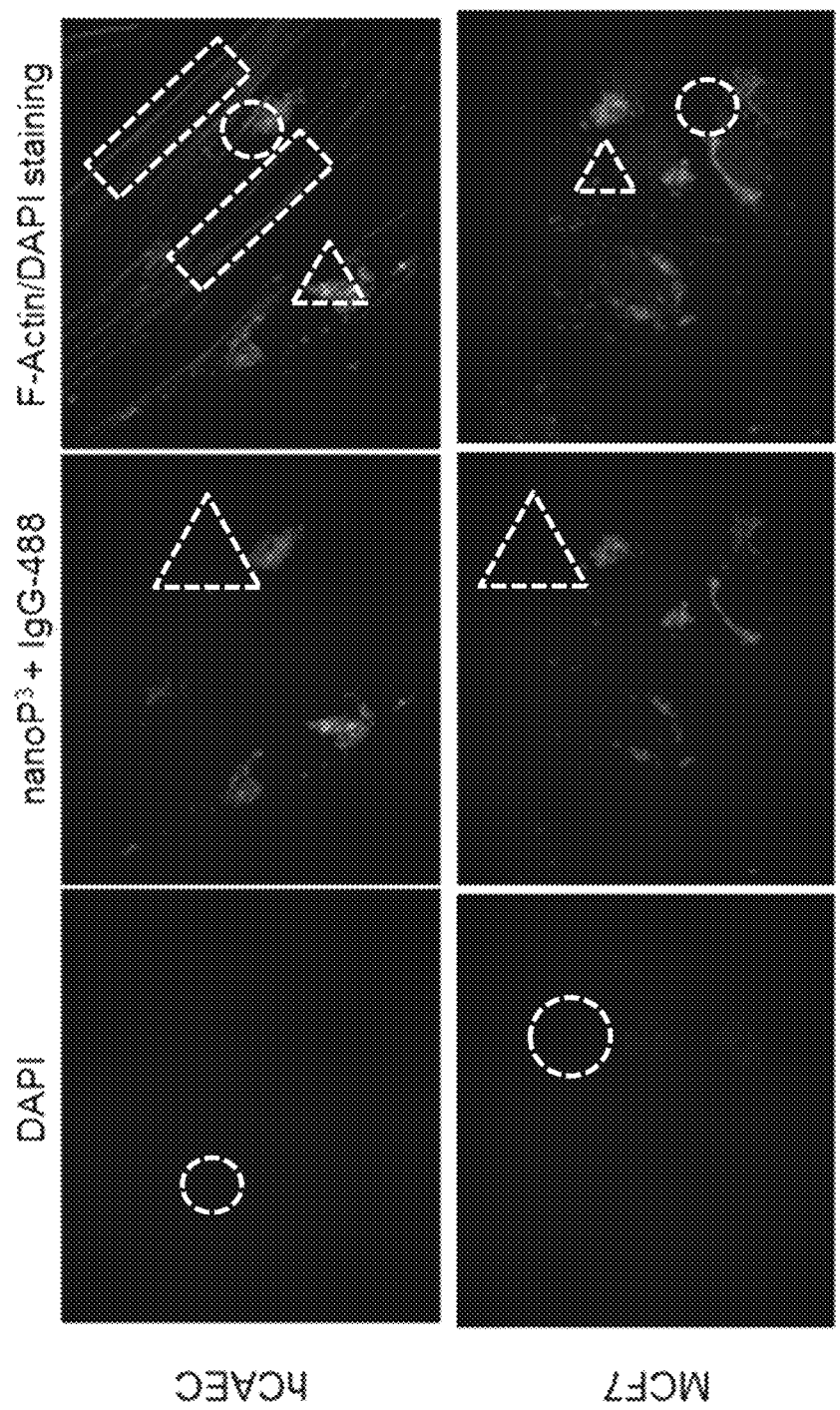
FIG. 41—Antibody functionalised nanoP$^3$ incubated with human coronary artery endothelial cells (hCAEC, top row) and breast cancer cell line MCF7 (bottom row), before fluorescent imaging.

FIG. 41 shows antibody functionalised nanoP³ incubated with human coronary artery endothelial cells (hCAEC, top row) and breast cancer cell line MCF7 (bottom row), before fluorescent imaging. Cell nuclei were stained blue with DAPI (for clarity certain cell nuclei are outlined with circular frames) and antibodies tagged green with Alexa 488 (for clarity some of these antibodies are outlined with triangular frames). Actin fibres were stained red (for clarity some of these fibres are outlined with rectangular frames). Fluorescence from the nanoP³ and Alexa 488 antibody conjugate was observed in the cell cytoplasm concentrated around the nucleus in both cell types.

Figure 40:
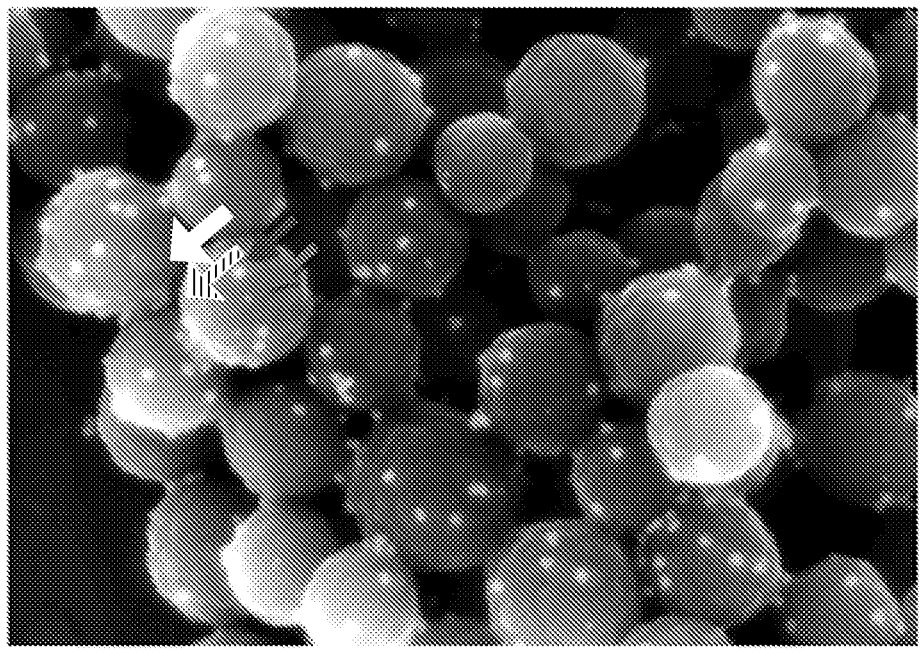
FIG. 40—NanoP$^3$ and two gold antibodies of different sizes (solid arrows 20 nm, striped arrow 6 nm) imaged using the detection of secondary electrons in the scanning electron microscope.
Figure 40:
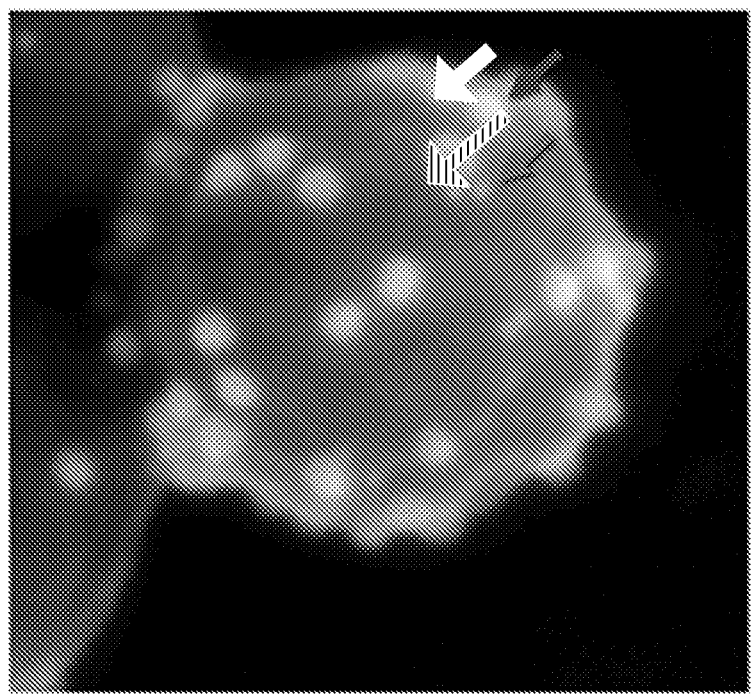

FIG. 40 provides SEM images of nanoP³ and 2 different sizes of gold antibodies (solid arrows 20 nm IgG-gold secondary antibody, striped arrow 6 nm one IgG-gold secondary antibody) imaged using the detection of secondary electrons in the SEM.

In order to confirm the bioactivity of conjugated molecules to nanoparticles, the inventors conjugated Horseradish Peroxidase (HRP), a heme-containing enzyme known to be particularly sensitive to conformational changes when immobilised. For this, nanoparticles were incubated with a 0.5 µg/mL solution of HRP and left homogenising for 4 hours. Controls of nanoparticles alone and HRP alone at equal concentrations were also performed, the latter showing below background levels of activity. In order to compare to the current gold standard of nanoparticles, commercially available gold nanoparticles were also incubated with HRP and treated as per the nanoparticles test group. After thorough washing of the nanoparticles (and controls) to remove all free HRP, the samples were incubated with ABTS, a well described substrate of HRP which yields a green product upon catalysis. Measurement of the absorbance at 405 nm shows a clear signal of HRP product formation, proving the maintained bioactivity of nanoparticles conjugated HRP. The commercial gold nanoparticles also showed some level of HRP activity, albeit at significantly lower levels. This may be due to a higher HRP loading on nanoparticles when compared to gold nanoparticles, or alternatively to a higher activity of the nanoparticles conjugated HRP, as the loss of HRP activity after conjugation to gold nanoparticles has been well documented.

Figure 42:
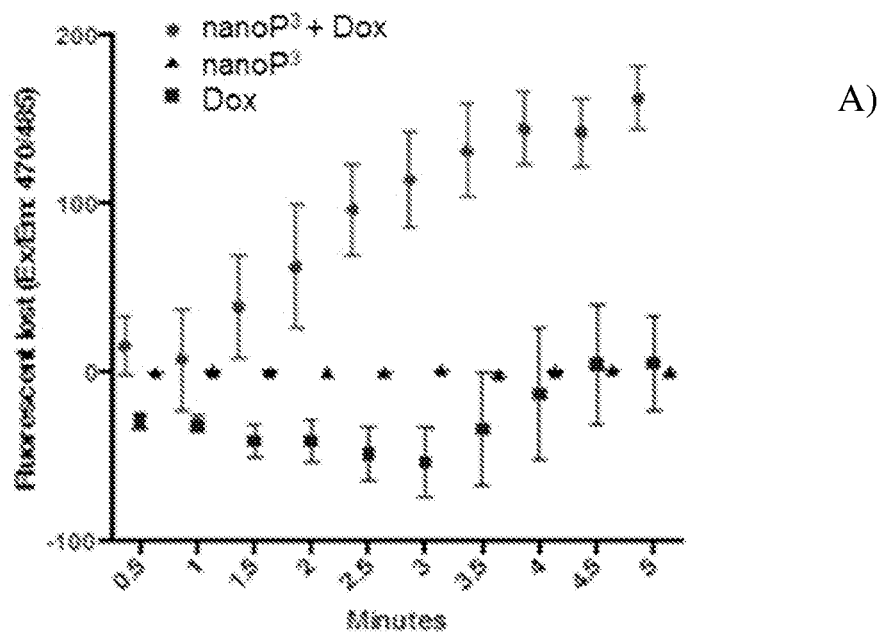
FIG. 42—Fluorescence loss of doxorubicin (Dox) when conjugated to nanoparticles (A); and cell viability assay (B).
Figure 42:
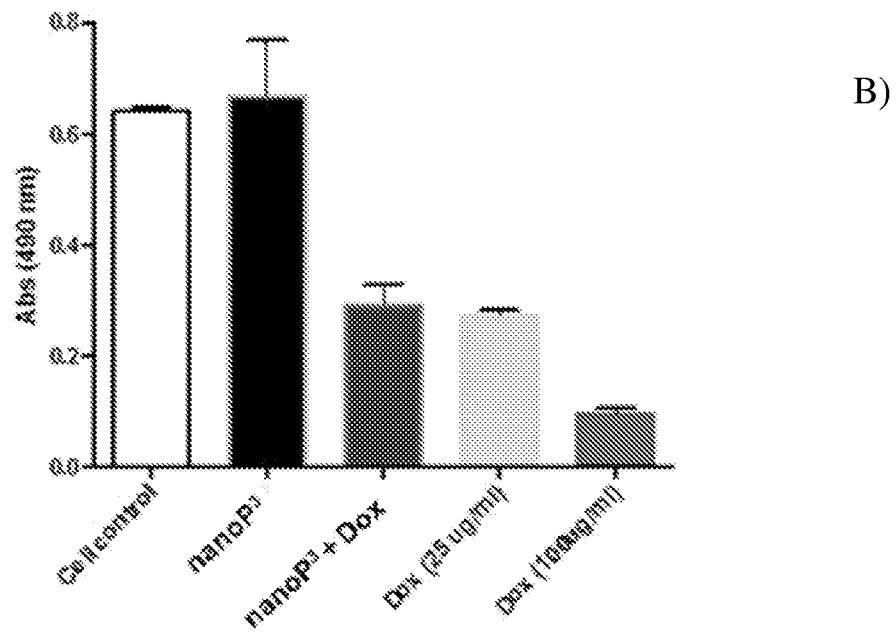

For the visualisation of doxorubicin, the inventors were expecting to observe the inherent auto-fluorescence of the drug, without the need for a separate fluorophore conjugate. However, the auto-fluorescence of doxorubicin was found to be quenched when incubated with nanoparticles, a phenomenon not uncommon when this drug is conjugated to other particles, or even to itself. The detection of doxorubicin conjugation with nanoparticles was thus achieved by measuring the loss in auto-fluorescence when the drug was incubated with the nanoparticles (FIG. 42, image A). Results show a progressive loss in fluorescence when doxorubicin is incubated with the nanoparticles, which steadily increases and plateaus at approximately 3 minutes, demonstrating an incredibly rapid conjugation. The doxorubicin control did not decrease in fluorescence, confirming the loss was not due to drug aggregation and consequent quenching. Interestingly, an increase in doxorubicin auto fluorescence was observed. This is thought to be due to the initial aggregation (and consequent quenching) of doxorubicin in the original stock solution. After dilution to 50 µg/mL in water, the aggregated doxorubicin begins to disaggregate, thus leading to a transient increase in fluorescence. The nanoparticle control without drug also showed no decrease in fluorescence. In a separate experiment, doxorubicin conjugated nanoparticles were thoroughly washed in water to remove all free doxorubicin and were subsequently added to a monolayer of breast cancer cells and left to incubate for 24 hours. Results of a MTS assay show a significant decrease in cell viability after 24-hour incubation with doxorubicin conjugated nanoparticles, confirming drug conjugation and subsequent bioavailability of the drug to induce cell death (FIG. 42, image B). The nanoP$^3$ material and the doxorubicin (Dox) was shown to kill MCF-7 cells to an extent equal to free doxorubicin (25 ug/ml) added to the media whereas the nanoparticles had no effect on cell viability. This experiment shows that cytotoxic drug, doxorubicin can be bound to the nanoparticles following simple incubation and can effectively kill MCF-7 breast cancer cells.

Figure 43:
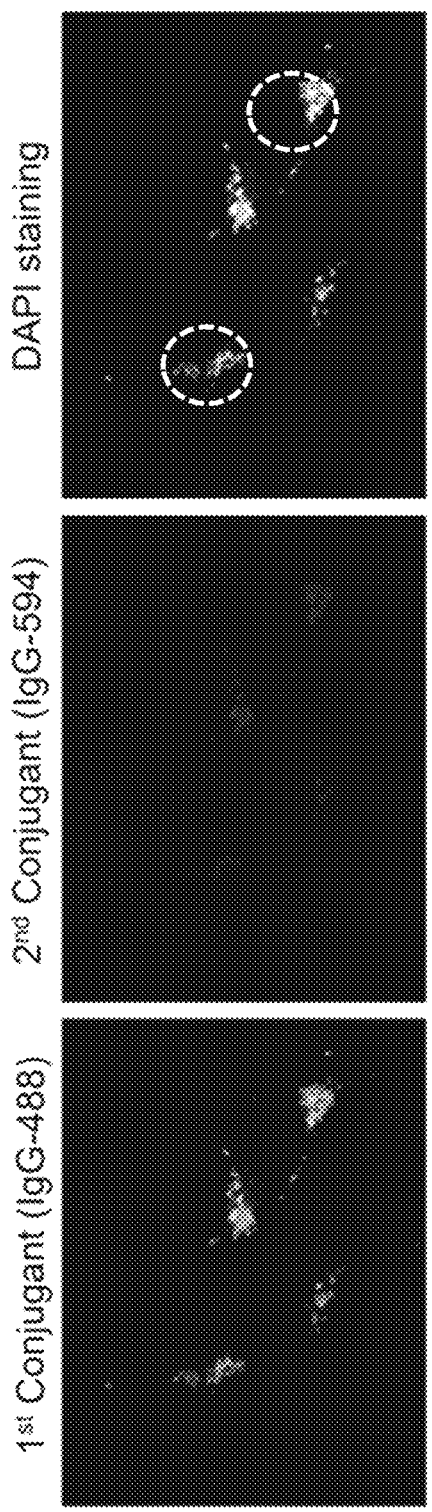
FIG. 43—NanoP$^3$ conjugation with IgG-488 and IgG-594.

The loading ability of the conjugates was demonstrated by introducing multiple bioactive groups on to the nanoP$^3$ material. FIG. 43 shows the conjugation of both IgC-488 and IgG-594 in a study with hCAEC cells. Cell nuclei are shown with DAPI (for clarity the nuclei in FIG. 43 are marked with circular frames). Both of the conjugants were detected from nanoP$^3$ and Alexa 488 antibody; and nanoP$^3$ and Alexa 594 antibody. The nanoP$^3$, Alexa 488 and Alexa 594 appears to be co-localised in the cell cytoplasm of human coronary artery endothelial cells (hCAEC), primarily around the nucleus.

Figure 44:
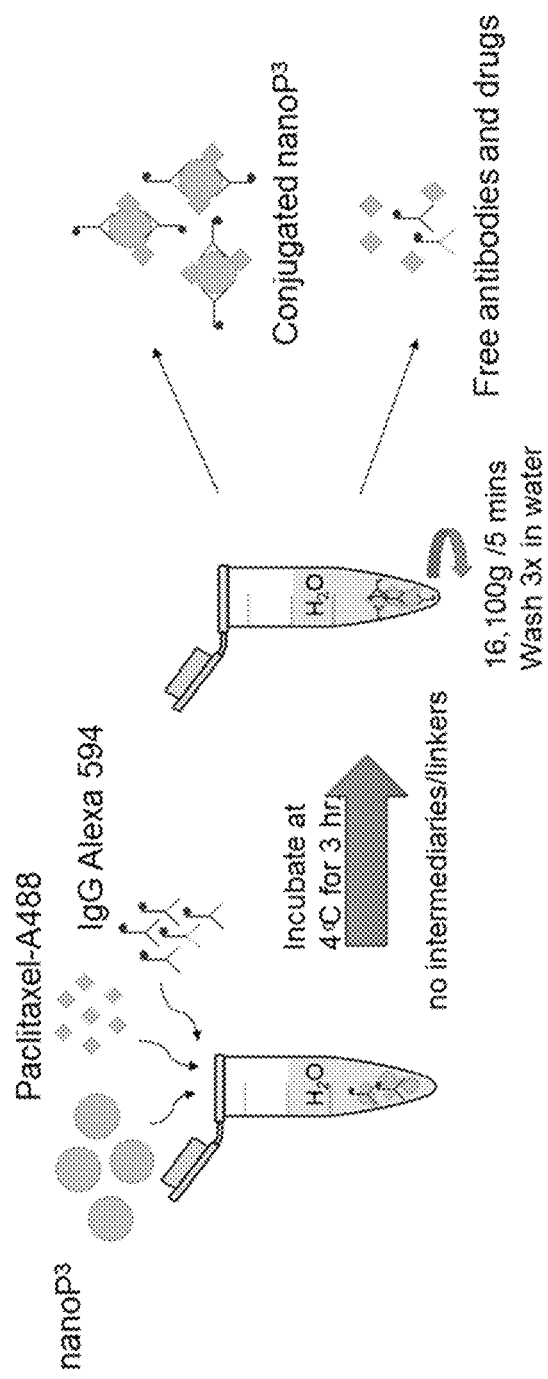
FIG. 44—Schematic diagram illustrates double functionalisation of nanoP$^3$ with an antibody and a drug.
Figure 45:
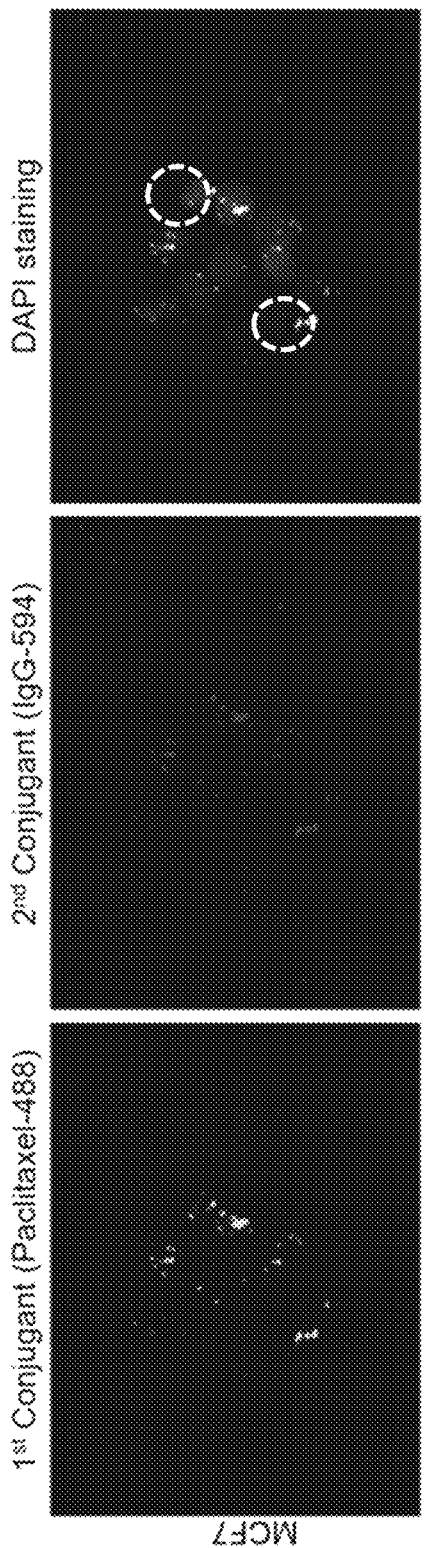
FIG. 45—Cell studies for nanoP$^3$ conjugation with Paclitaxel-488 and IgG-594.

Different types of second species may be placed on the conjugates, for example a drug and an antibody may be utilised (FIG. 44). In FIG. 45 the conjugation of paclitaxel-488 and IgG-594 is depicted in a cell study with MCF7 cells; the cell nuclei are shown with DAPI (for clarity some of the nuclei in FIG. 45 are marked with circular frames). Both of the conjugants were detected from: nanoP$^3$ and Paclitaxel-488; and nanoP$^3$ and Alexa 594 antibody. The nanoP$^3$, Paclitaxel-488 and Alexa 594 appears to be co-localised in the cell cytoplasm of MCF7 breast cancer cells.

Figure 46:
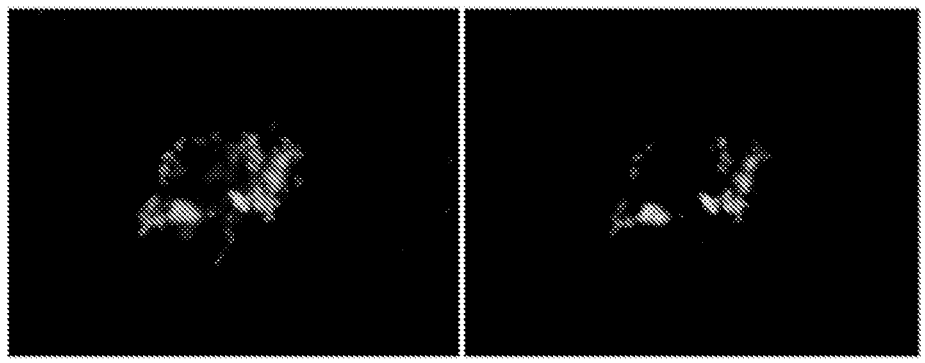
FIG. 46—Conjugation of IgG-488, IgG-Cy5 and IgG-Cy7 with nanoP$^3$ and a cell study with MCF7 cells.
Figure 46:
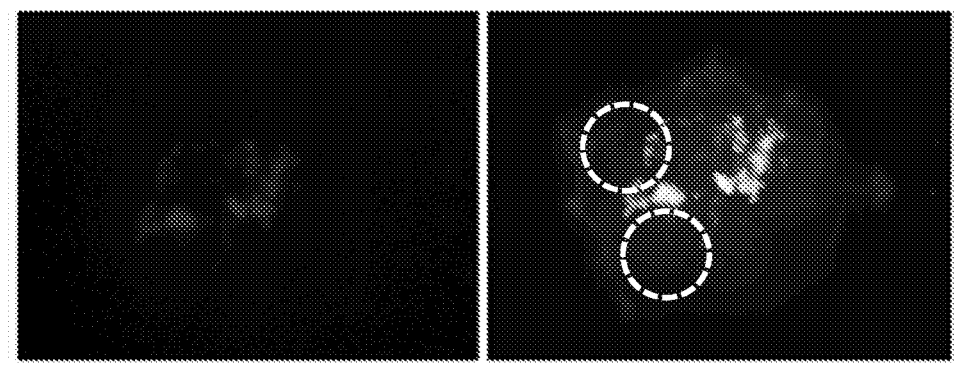

In FIG. 46 the conjugation of IgG-488, IgG-Cy5 and IgG-Cy7 with nanoP$^3$ is depicted in a cell study with MCF7 cells; the cell nuclei are shown with DAPI (for clarity the nuclei in FIG. 46 are marked with circular frames). All three conjugants were detected from: nanoP$^3$ and Alexa 488; and nanoP$^3$, Alexa Cy5 and Alexa Cy7 antibody. The nanoP$^3$ and all three conjugates appear to be co-localised in the cell cytoplasm of MCF7 breast cancer cells.

Figure 47:
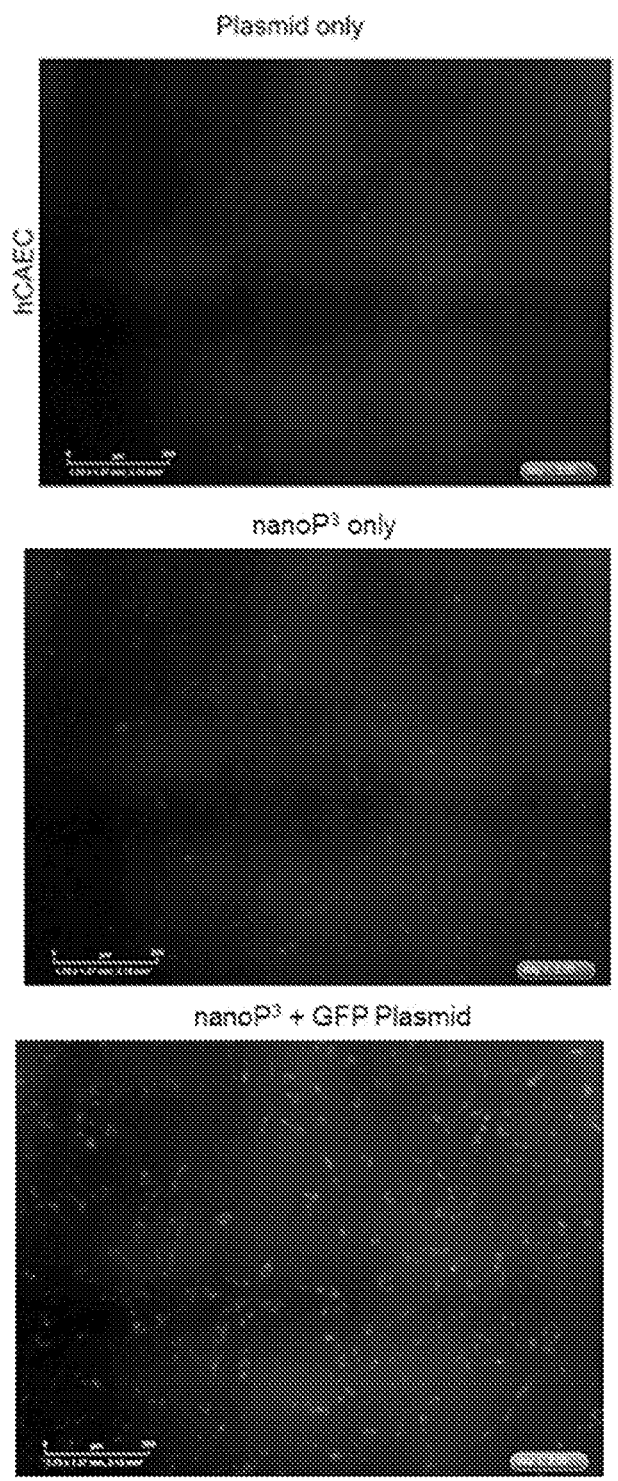
FIG. 47—Studying the transport of plasmid in human coronary artery cells using nanoP$^3$.

Carrying double stranded DNA, including plasmids into cells using traditional methodology requires cell penetrating methods (e.g., electroporation) or reagents (e.g., lipofectamine). In one experiment the Inventors used a plasmid for generating green-fluorescent protein, making successfully transfected cells appear to fluoresce green. Using human coronary artery cells (hCAEC) the Inventors added plasmid, nanoP$^3$ only, or nanoP$^3$ with plasmid, with no additional cell penetration steps (FIG. 47). Incubation with the plasmid only, or nanoP$^3$ only caused no effect. In striking contrast, the nanoP$^3$ and plasmid condition showed many successfully transfected cells over a 24 hour period.

Figure 48:
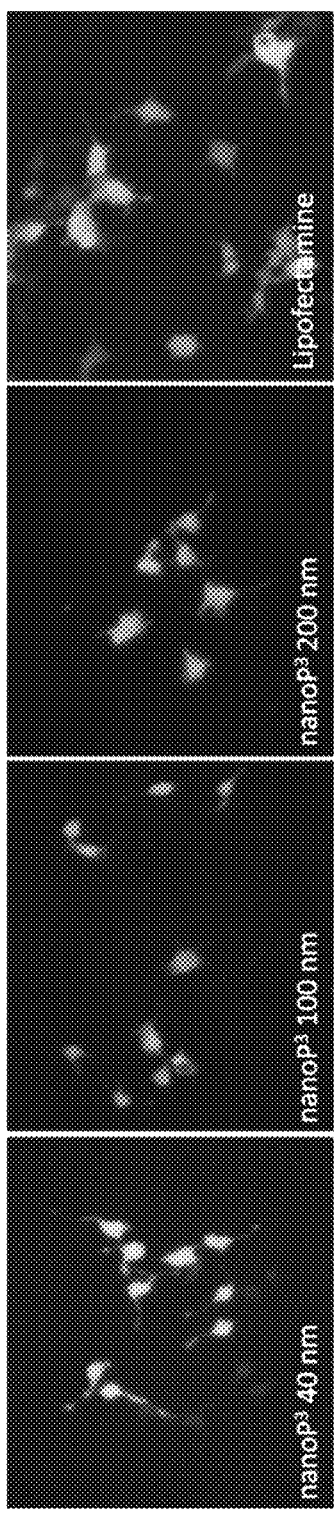
FIG. 48—Studying the transport of plasmid in human embryonic kidney cells bound to different sizes of nanoP$^3$.

In another experiment, the Inventors successfully delivered a plasmid for generating green-fluorescent protein bound to 40, 100 or 200 nm nanoP$^3$ to Human Embryonic Kidney cells (HEK293). 72 hours post-transfection, transfected cells were observed (Green) under the fluorescent microscope (FIG. 48), illustrating the successful transfection of cells and retained function of cargo (e.g., DNA plasmids) achieved by the nanoP$^3$ materials disclosed herein. These results demonstrate that nanoP$^3$ can carry DNA across the cell membrane and retain its activity.

In a preliminary animal experiment, mice were given small incisions on their back (i.e., a wound). Four groups were then given:
1) no intervention;
2) nanoP$^3$ only;
3) commercial gold nanoparticle and luciferase; or
4) nanoP$^3$ and luciferase by tail vein injection.

Figure 49:
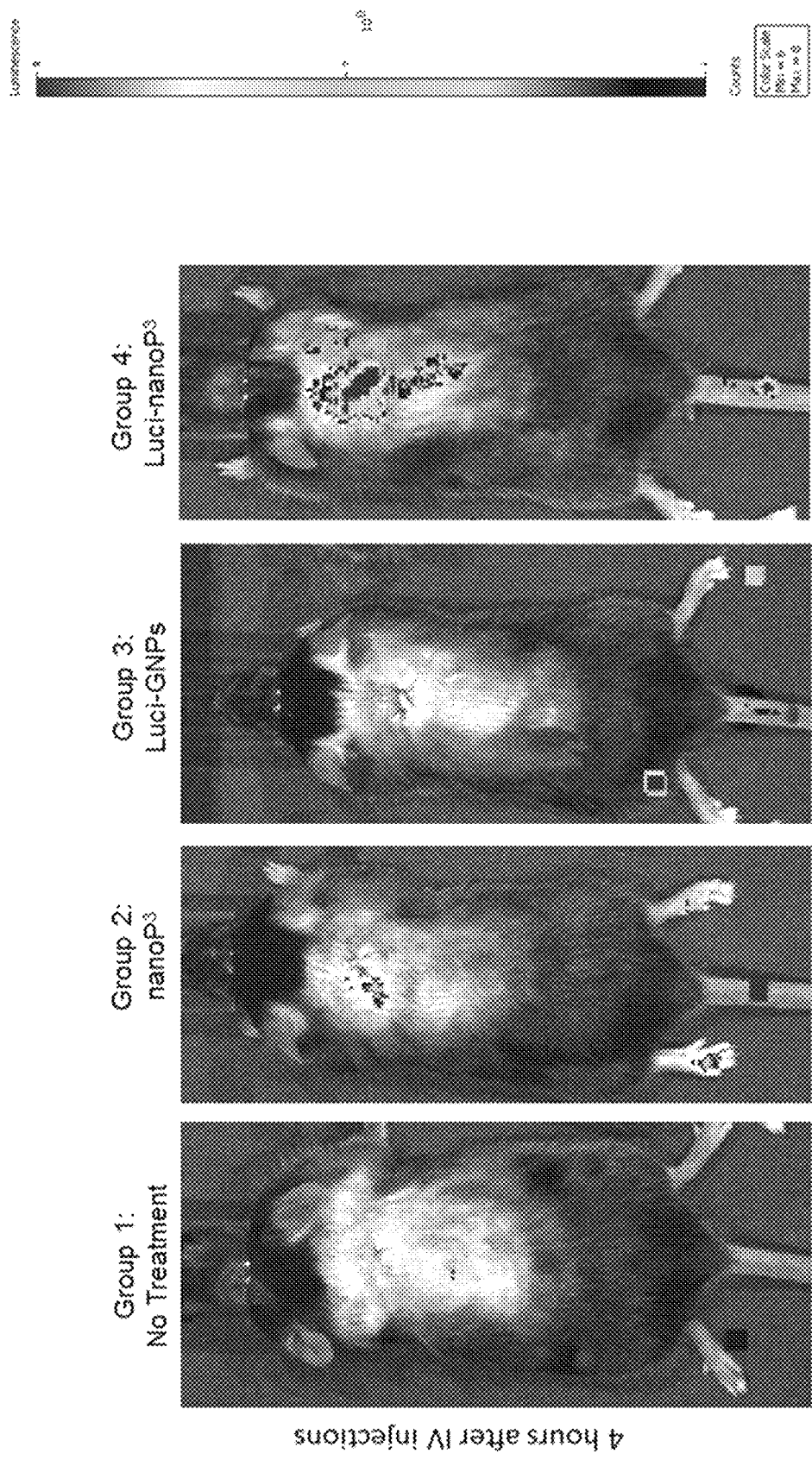
FIG. 49—In vivo imaging system (IVIS imaging) of mice delivered nanoP$^3$ material and conjugates thereof.

Only group 4 (nanoP$^3$ and luciferase), showed a positive signal at the wound region by IVIS imaging (FIG. 49). This suggested that only nanoP$^3$ covalently retains the luciferase in a bioactive manner, and that nanoP$^3$ may be homing to the site of injury—with significant implications for in vivo imaging and treatment.

Typical materials used in nanotherapeutics are bioactively inert and usually require further functionalisation strategies with oligomers, such as PEG, to achieve a stable conjugation between pharmaceutical agents and the nanoparticle surface. In this work, the Inventors report a novel plasma activated nanocarrier that provides a direct and radical-mediated conjugation of a variety of biomolecules, without compromising the bioactivity of the immobilised biomolecules. Nanoparticle synthesis and collection is performed in an active plasma-gas phase, involving the rapid aggregation of nano-sized carbon-based clusters. Nanoparticle production yields and physicochemical properties are readily tailored, accordingly with the application requirements, by choosing appropriate windows of process parameters. The non-toxic nature of the nanoparticles has been demonstrated on a variety of cell types and particle concentrations. Nanoparticles produced herein were further shown to passively enter the cells, facilitating the movement of molecular cargos such as drugs, antibodies and polynucleotides. It has been demonstrated that plasma discharges provide a robust platform for the synthesis and design of a new class of truly multifunctional nanocarriers that can potentially propel current outcomes in nanoparticle-based therapeutics and diagnostics.

Example 14—Conjugation Studies Part 3

In another animal experiment, mice were divided randomly into 3 groups:
1) nanoP$^3$ only;
2) nanoP$^3$ and ICG; or
3) ICG only.

Figure 50:
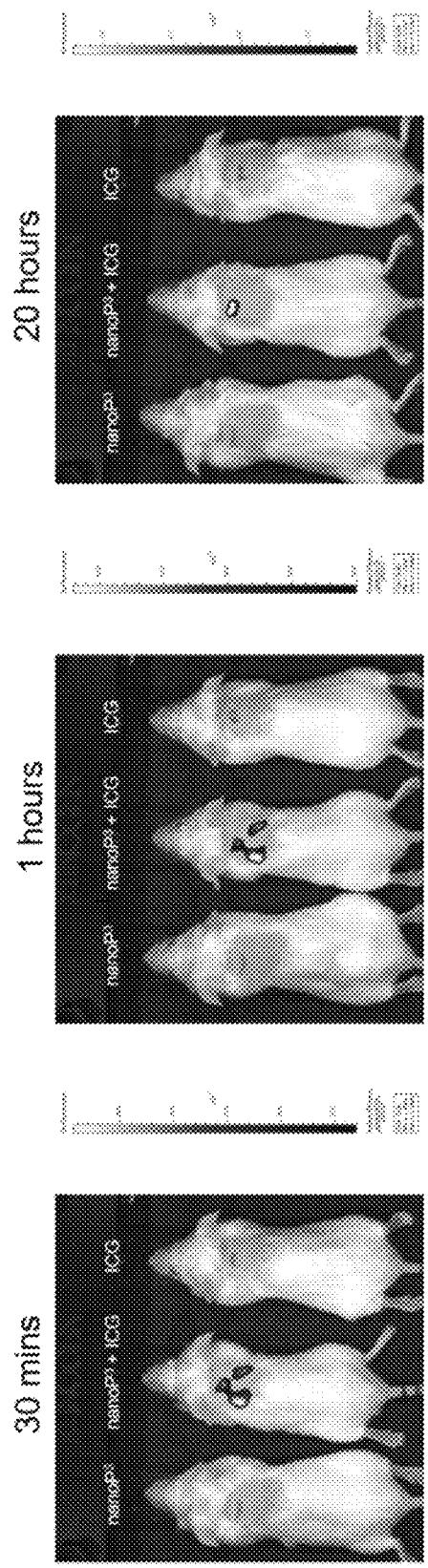
FIG. 50—In vivo imaging system (IVIS imaging) of mice delivered indocyanine green (ICG) conjugated to nanoP$^3$ material.

For each group, as shown in FIG. 50, a small incision (5 mm) was made on the back of the mouse. Following closure of the incision with silk sutures, each mouse was administered with 100 μL of the corresponding sample groups via tail vein injection: nanoP$^3$ control (9×10$^9$ nanoP$^3$), nanoP$^3$-ICG (9×10$^9$ nanoP$^3$ with 2.5 μg of ICG/10$^9$ nanoP$^3$) or ICG control (22.5 μg). Non-invasive imaging using IVIS was carried out for detection of fluorescence at Ex/Em=780 nm/820 nm. For all time points studied, fluorescence was absent in both nanoP$^3$ only and ICG only control groups, showing that ICG significantly loses activity upon circulation in vivo. Conversely, signal was detected on the nanoP$^3$-ICG group for all time-points, demonstrating that ICG activity in vivo is significantly prolonged (increase in half-life of 300-fold) once bound to nanoP$^3$.

Example 15—Conjugation Studies Part 4

Figure 51:
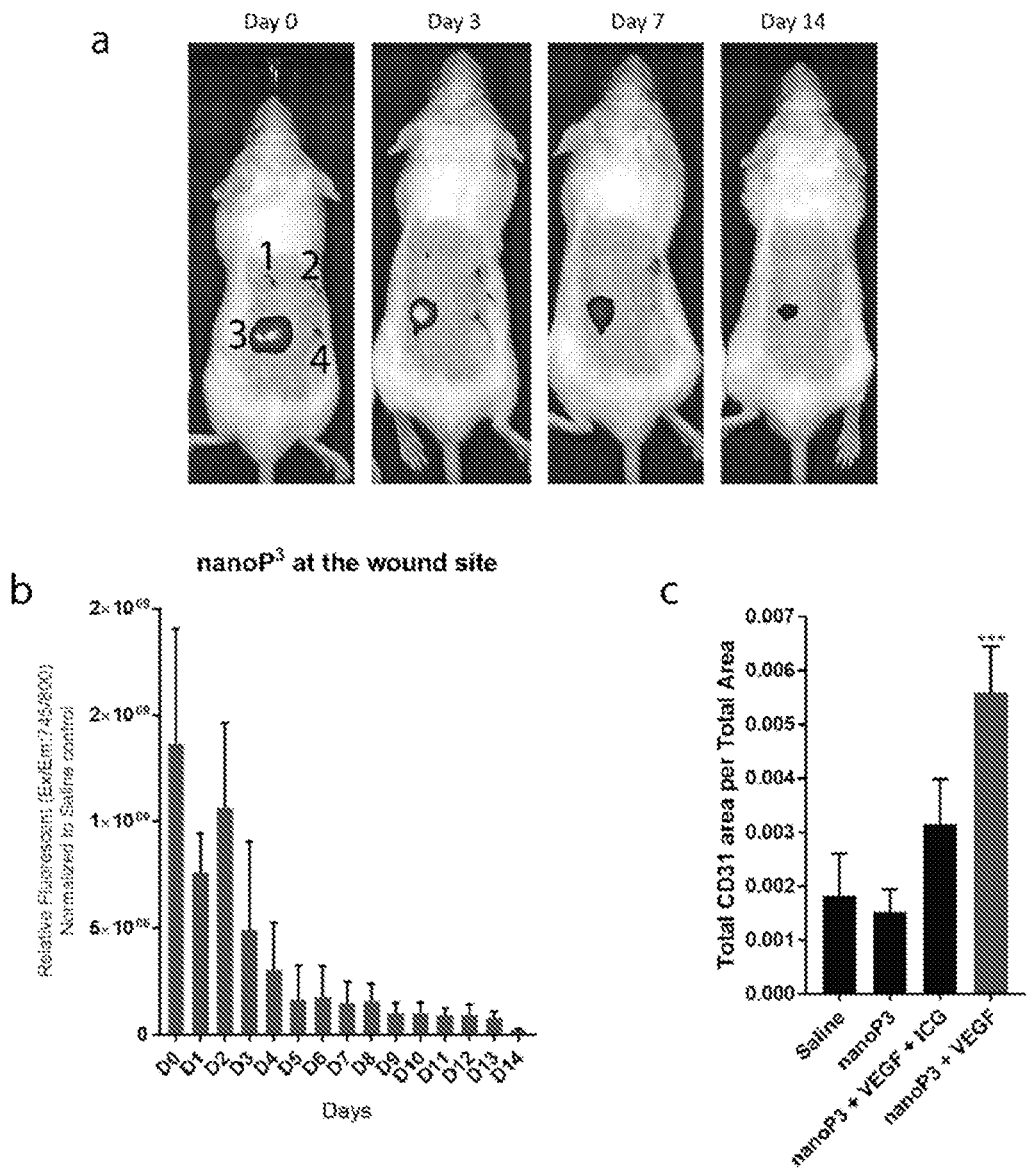
FIG. 51—In vivo imaging system (IVIS imaging) of mice delivered nanoP$^3$ material and conjugates thereof.

In another animal experiment, as shown in FIG. 51 image A, a total of 4 incisions (5 mm) were made on the back of each mouse for local delivery of various sample groups: saline control (incision 1), nanoP$^3$ only (incision 2), nanoP$^3$-VEGF-ICG (incision 3) and nanoP$^3$-VEGF (incision 4). The total administered sample volume per wound was 5 μL. For the groups containing nanoP$^3$ the administered dosage was as follows. Incision 2: 5×10$^9$ nanoP$^3$; Incision 3: 5×10$^9$ nanoP$^3$ with 0.058 μg of VEGF/10$^9$ nanoP$^3$ and 1.25 μg of ICG/10$^9$ nanoP$^3$; incision 4: 5×10$^9$ nanoP$^3$ with 0.115 μg of VEGF/$10^9$ nanoP$^3$. FIG. 51 image B shows that only the sample group containing nanoP$^3$ functionalised with ICG resulted in a positive fluorescent signal. The fluorescence intensity decreased over time (quantified until day 14 post incision) and remained confined to the wound site. As shown in FIG. 51 image C, further analysis of the wound tissue with immunohistochemistry revealed an enhancement in endothelialisation in the nanoP$^3$-VEGF-ICG and nanoP$^3$-VEGF groups (the latter significant) compared with saline and nanoP$^3$ only controls. These results demonstrate that functional cargo immobilized on nanoP$^3$ can be delivered in vivo while enabling simultaneous imaging of the distribution of nanoP$^3$ in the host tissue.

Example 16—Conjugation Studies Part 5

Methods and Materials
Cell Viability Assay
 Cytotoxicity was evaluated for 3 different cells types:
 1) human Coronary Artery Endothelial cells (hCAEC, passage 4, Cell Applications, 300-05a);
 2) human Breast Cell line (MCF10A, passage 20); and
 3) Breast cancer cells (MCF7, passage 15, Sigma-Aldrich, 86012803).

Approximately 5,000 cells/cm$^2$ were counted and seeded in a flat-bottomed 24 well culture plate and incubated for 4 hours at 37° C. in a 5% $CO_2$ incubator. Four hours after cell seeding, 10× dilutions of nanoP$^3$, from 10 million particles/well to 100 particles/well were then added into the medium, with n=3 replicates for each concentration of nanoP$^3$. After 3 and 5 days of incubation, the cytotoxicity evaluation was performed using alamarBlue cell viability and cytotoxicity assay kit (Life technologies, DAL1100). The alamarBlue reagent was added to each well as per manufacturer's instructions and was further incubated for 2 hours (for hCAEC and MCF10A), and 3 hours (for MCF7). The resazurin dye produced by viable cells was quantified via measuring the fluorescence at Ex/Em 530-560/590 nm. Untreated cells (no nanoP$^3$) and cells treated with Doxorubicin (500 nM, Sigma-Aldrich, 44583) were used as controls.

Conjugation of nanoP$^3$ to Gold Nanoparticles Conjugated-Secondary Antibodies
 NanoP$^3$ was incubated with desired antibodies (Goat anti-Rabbit-IgG-40 nm Gold; abcam, ab119180, Goat anti-Mouse-IgG-20 nm Gold; abcam, ab27242, and/or Goat anti-Rat-IgG-10 nm Gold; abcam, ab41512) for 1 h at 4° C., and gently agitated using Bio RS-24 mini-rotator. After incubation, the samples were washed via centrifugation at 16,100 g, for 5 minutes. The samples were then collected and left to air-dry in the tissue culture hood on 300 mesh Copper (Proscitech, GSCu300C), and visualised using Zeiss Sigma HD FEG SEM (SMM Facilities, Sydney)

Conjugation of nanoP$^3$ to Secondary Antibodies and/or Drugs
 NanoP$^3$ was conjugated to secondary antibodies (Donkey anti-Goat IgG-Alexa488; abcam, ab6881; Goat anti-Rat IgG-Alexa647; abcam, ab150159, Goat anti-Rabbit IgG-750; abcam, ab175733) and/or drugs (Paclitaxel-Oregon Green 488, Invitrogen P22310) for 1 hour at 4° C., protected from light and gently agitated using Bio RS-24 mini-rotator. After incubation, the test samples and appropriate controls were washed equally 3 times via centrifugation at 16,100 g, for 5 mins per wash. The fluorescence intensity was measured using a plate reader, the Ex/Em were set in accordance to the fluorescent dye tag on each antibodies or drugs.

Antibody Conjugated nanoP$^3$ in Cells
 hCAEC, MCF10A and MCF7 cells were seeded at a density between 10,000-15,000 cells/cm$^2$ on Lab-Tek glass chamber slides suitable (Lab-Tek, 154534, and 155380) for cell culture for images. Four hours after cell-seeding, test nanoP$^3$ samples and controls were incubated with all cell types for 24 hours. The cells were then fixed with 3.7% Paraformaldehyde for 10 minutes at room temperature. The samples were then washed 3 times with PBS prior to the cell staining.

Actin and DAPI Staining
 After fixation, cells were permeabilised with 0.1% x-triton 100 in PBS for 5 minutes. The samples were then washed 3 times in PBS. Cells were then incubated in Actin Red 555 ReadyProbes reagent (Life technologies, R37112) for 15 minutes, a dilution of 20 µl of the reagent to 1000 µl of PBS. The samples were then washed 3 times in PBS. The cells were incubated with DAPI Solution (1:1000 dilution in PBS, SAPBIO, NBP2-34422R) for 5 minutes at room temperature. The samples were washed 3 times in PBS prior to mounting with an aqueous fluorescent-shield mounting medium (Cat.). After cover-slipping, the images were taken within 24 hours under a fluorescent microscope (Zeiss Microscope).

Functionalised Assay: Conjugation of nanoP$^3$ to Luciferase
 NanoP$^3$ were conjugated to Luciferase from Photinus pyralis at 2.5 µg/ml (abcam, L9506) for 1 hour at 4° C., gently agitated using Bio RS-24 mini-rotator. Conjugation of Luciferase to 200 nm Polystyrene (ThermoFisher Scientific; R200) and 200 nm gold nanoparticles (Cytodiagnostics; G-150) were performed in an identical fashion. After incubation, the nanoP$^3$ samples were washed 3 times via centrifugation at 16,100 g, 5 minutes per wash, whereas, appropriate controls were washed equally 3 times per manufacturer's instructions. All washes were collected. For detection of Luciferase, conjugated nanoparticles and respective controls and all their washes were incubated with D-Luciferin (Sigma-Aldrich; A1888), containing 70 mM ATP-$Mg^{2+}$. Bioluminescence were then detected (Exposure time: 30 sec.) via IVIS system.

Figure 52:
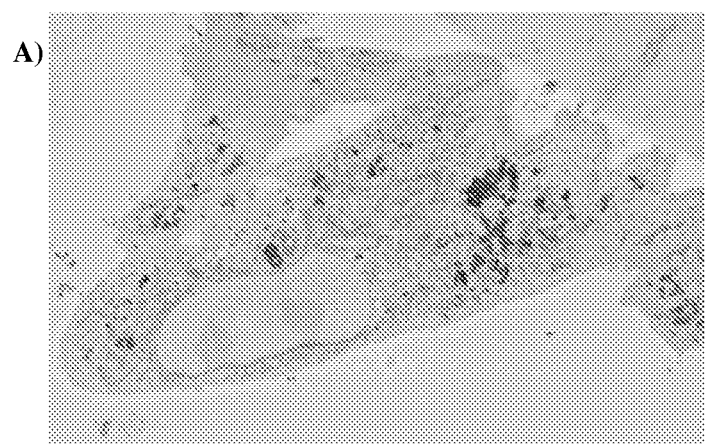
FIG. 52—SEM images of nanoP$^3$ inside human coronary artery endothelial cells (A); and 3D reconstruction of the sections shows a homogenous distribution of nanoP$^3$ in the cytoplasm (B).
Figure 52:
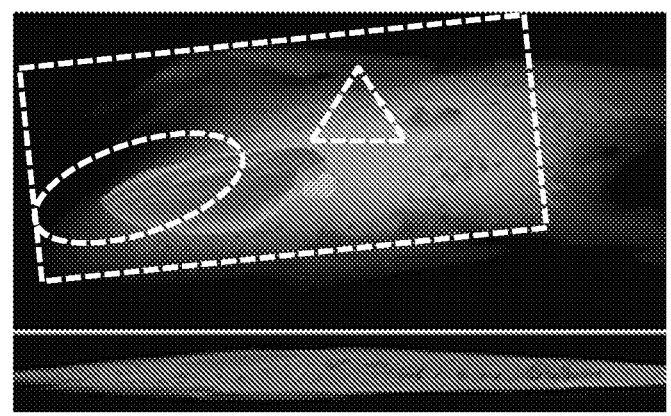
Figure 53:
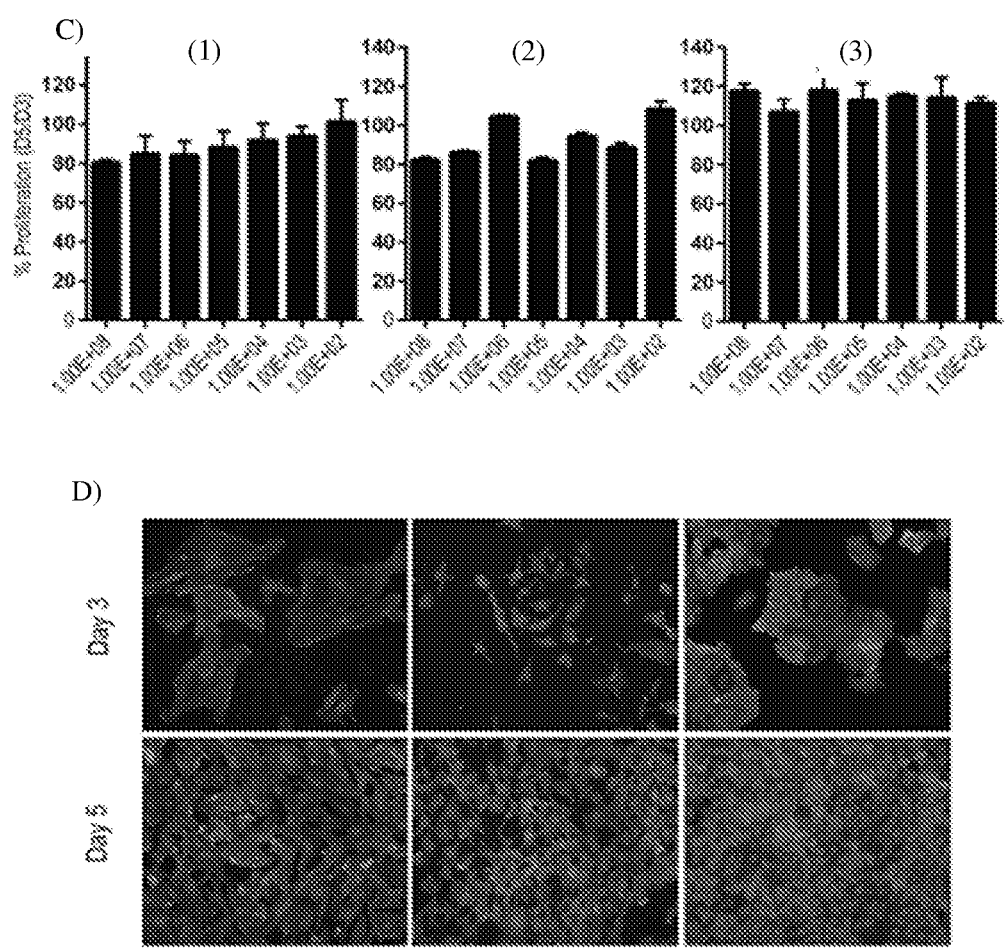
FIG. 53—Cell viability in the presence of nanoP$^3$ for HCAEC (1); MCF-10A (2); and MCF-7 (3) (C); and representative images of cells stained with actin-phalloidin (D).
Figure 54:
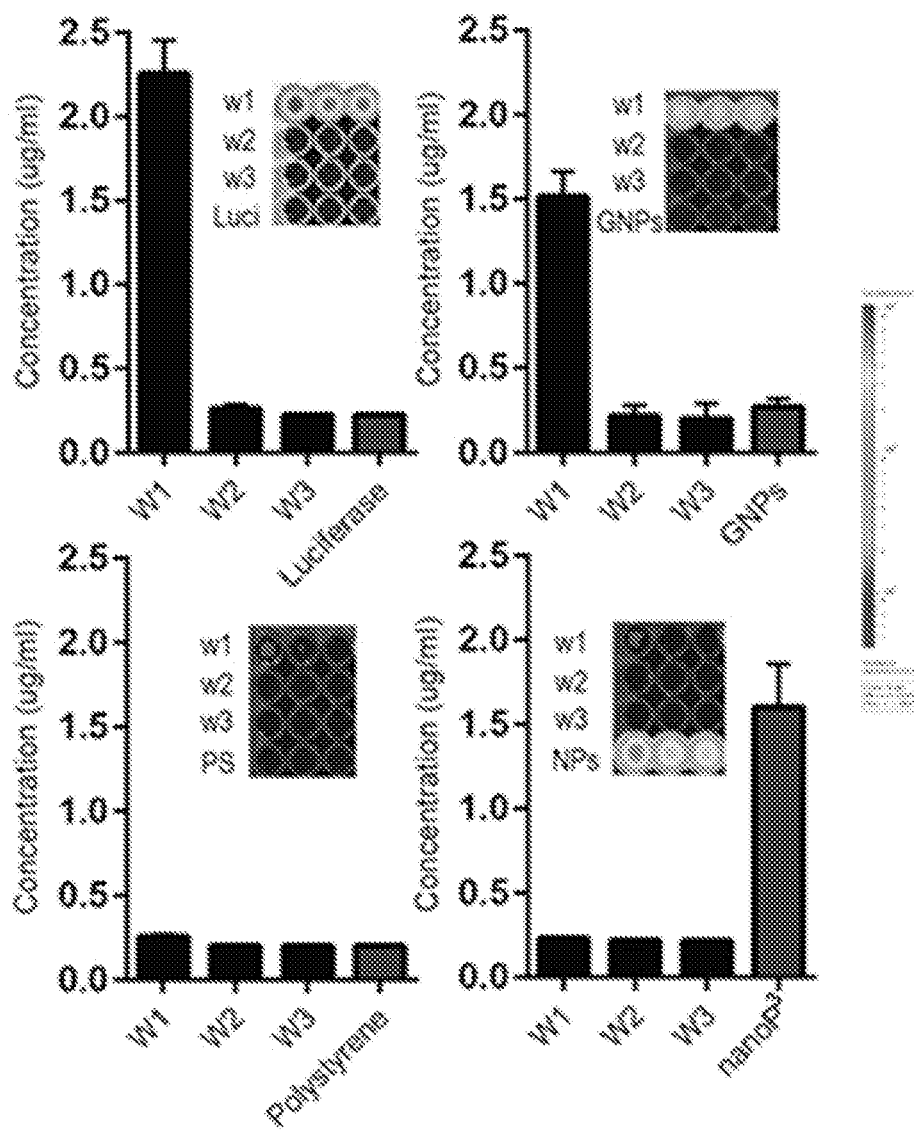
FIG. 54—Determining luciferase binding with: no carrier; gold nanoparticle carriers; polystyrene beads; and nanoP$^3$.

Results
 The presence of free radicals in nanoP$^3$ suggests the potential for direct covalent immobilisation of biomolecules by simple incubation, giving them an intrinsic advantage over competing platforms. Unfunctionalised nanoP$^3$ penetrated the membrane of human coronary artery endothelial cells (HCAECs) and accumulated in the cytoplasm, observed using 3View cross-sectional SEM (FIG. 52, image A). 3D rendering of these images show nanoP$^3$ (some of these are outlined with the triangular frame) distributed within the cell membrane (outlined by the rectangular frame), outside of the nucleus (outlined by the oblong frame) (FIG. 52, image B). NanoP$^3$ incubation with HCAECs, fibroblasts (MCF10A) or human breast adenocarcinoma cells (MC7) did not significantly affect cell viability, up to 1×$10^8$ particles per well (FIG. 53, image C). Cell morphology was also unaffected after 3 or 5 days in culture (FIG. 53, image D). Incubation with luciferase in the absence of additional chemical linkers, followed by three centrifugation washing steps (W1-W3), illustrated the biomolecule immobilisation capacity of nanoP$^3$. The bioluminescent enzyme luciferase was chosen to allow simultaneous study of functional activity as it is conformationally sensitive and inactive when unfolded. The assay was also conducted without particles, or with commercial gold (GNPs) or polystyrene nanoparticles to compare with nanoP$^3$ (FIG. 54). Only nanoP$^3$ provided irreversible immobilisation and preservation of the activity of luciferase throughout all wash steps.

The experiment highlights that all other commercial platforms, shown here for gold and polystyrene nanoparticles require chemical linking intermediates for robust binding of functional molecules.

Figure 55:
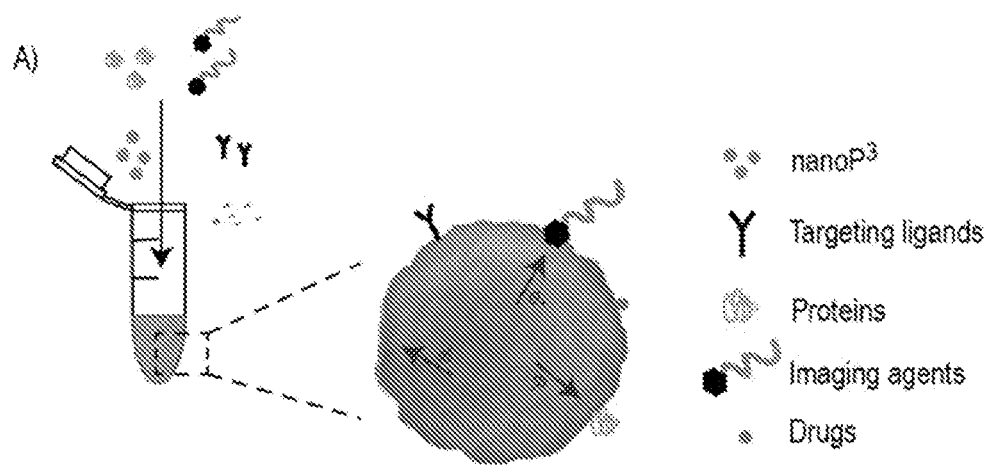
FIG. 55—Schematic showing the ability of the nanoP$^3$ material to bind multiple second species (A) and calculations of the binding capacities between the nanoP$^3$ and IgG488 antibody (B).
Figure 55:
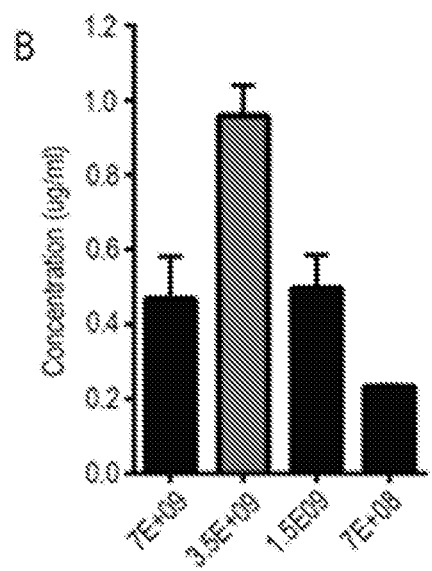
Figure 56:
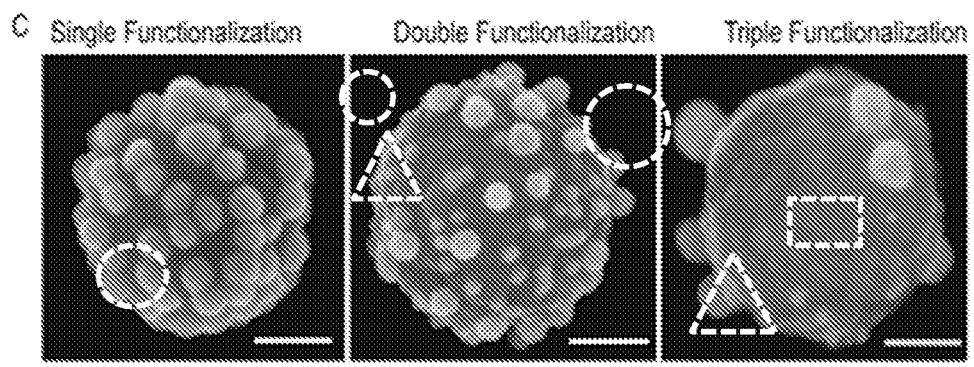
FIG. 56—High-resolution SEM imaging shows the functionalisation of nanoP$^3$ with: one IgG-gold secondary antibody 40 nm in size (as shown in dashed circular outline); two IgG-gold secondary antibodies which are 40 nm and 20 nm in size (as shown in dashed circular and triangular outlines, respectively); and three IgG-gold secondary antibodies which are 40 nm, 20 nm and 6 nm in size (as shown in dashed circular, triangular and rectangular outlines, respectively) (C); and zeta potential measurements of the nanoP$^3$ alone and following functionalisation with paclitaxel, IgG-Cy5 and IgG-Cy7 (D).
Figure 57:
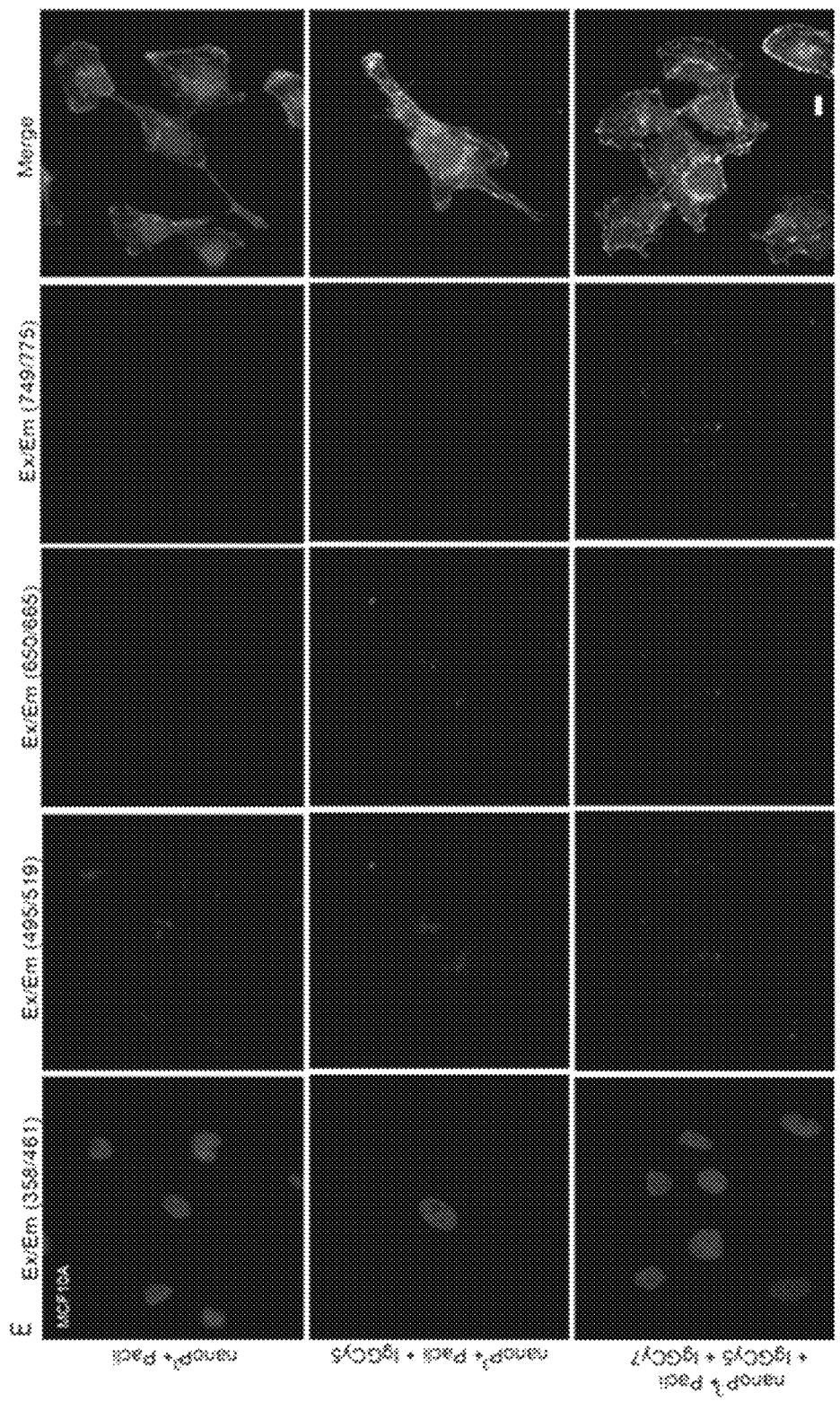
FIG. 57—Cell study with MCF10A cells and singly, double and triple functionalised nanoP$^3$ materials.

The potential to carry multiple covalently bound cargo, including targeting ligands, imaging agents and drugs without chemical intermediates (FIG. 55, image A) is a key aspect of nanoP$^3$. Exemplification with a fluorescently labelled antibody (IgG488) showed that a binding concentration consistent with a dense surface monolayer could be achieved (FIG. 55, image B). Gold labelled antibody binding to nanoP$^3$, visualised by SEM demonstrates functionalisation with 1, 2 or 3 ligands, with surface density controlled by solution parameters including antibody concentration and incubation time and order (FIG. 56, image C). In FIG. 56, image C the three IgG-gold secondary antibodies are 40 nm, 20 nm and 6 nm in size (as shown in dashed circular, triangular and rectangular outlines, respectively). Functional transfer of multiple cargo into cells was demonstrated using paclitaxel-488, IgG-Cy5 and IgG-Cy7 as single, double or triple functionalised nanoP$^3$ in MCF10A (FIG. 57). While exemplified for three relatively large functionalities, the binding capacity of nanoP$^3$ is only limited by the surface area as it relates to the size of the cargo.

Example 17—Conjugation Studies Part 6

Figure 58:
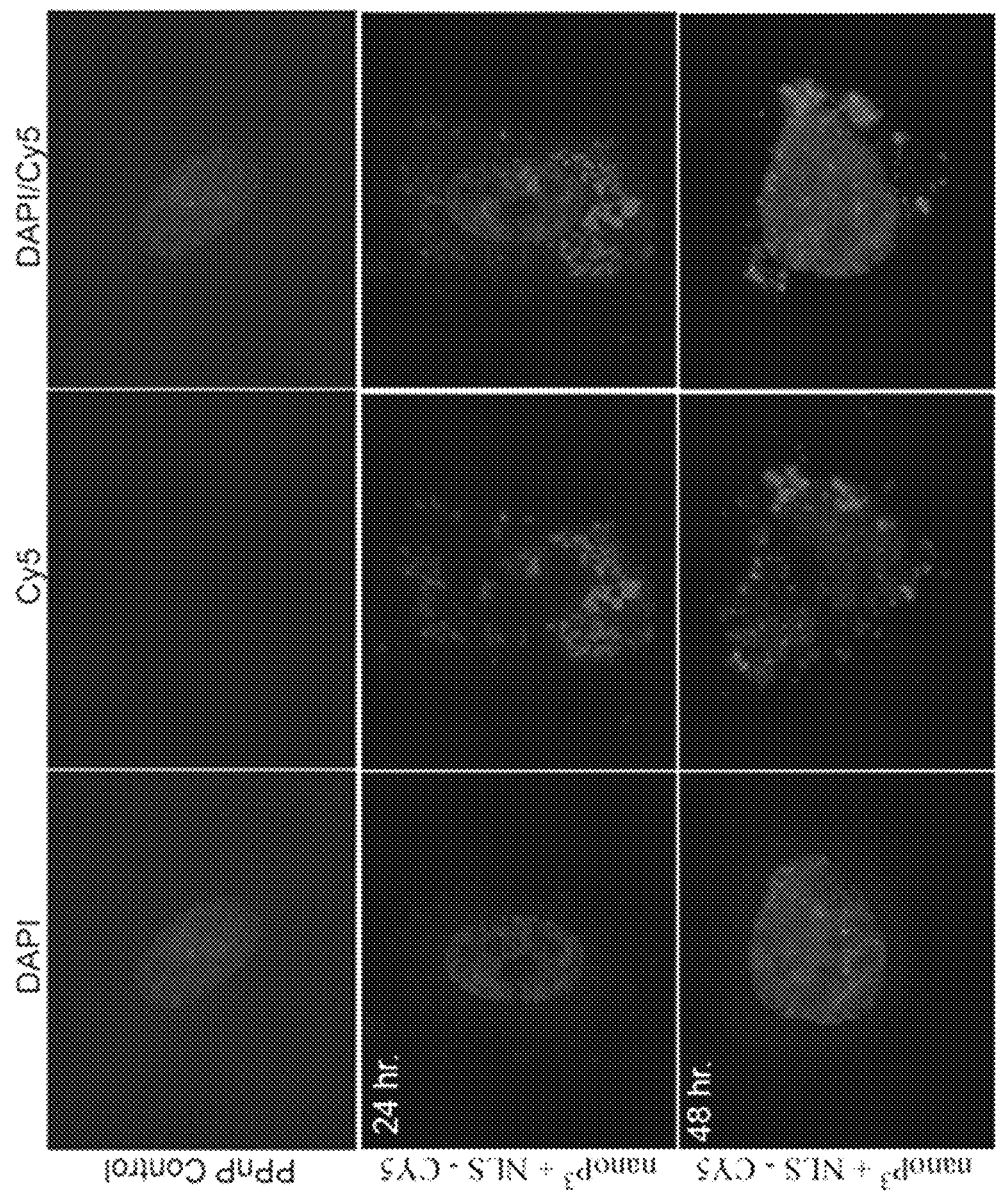
FIG. 58—Stained human umbilical vein endothelial cells after treatment with a conjugate comprising nanoP$^3$ particles and a nuclear localisation sequence.

NanoP$^3$ was conjugated with a nuclear localisation sequence (NLS), in particular the NLS of H-CPKKKRKV-OH was used. The resulting conjugate penetrated the nuclear membrane of human umbilical vein endothelial cells (HUVEC) (FIG. 58). Most of the nanoP$^3$-NLS conjugates accumulate around the nucleus 24 hours post incubation, as is generally observed when nanoparticles are incubated with cells. However, after 48 hours, a positive fluorescent signal is present in the nuclear region of the cells, indicating nanoparticle-NLS tracking to this organelle. This experiment demonstrates that different organelles may be targeted by forming suitable conjugates.

Example 18—Conjugation Studies Part 7

Figure 59:
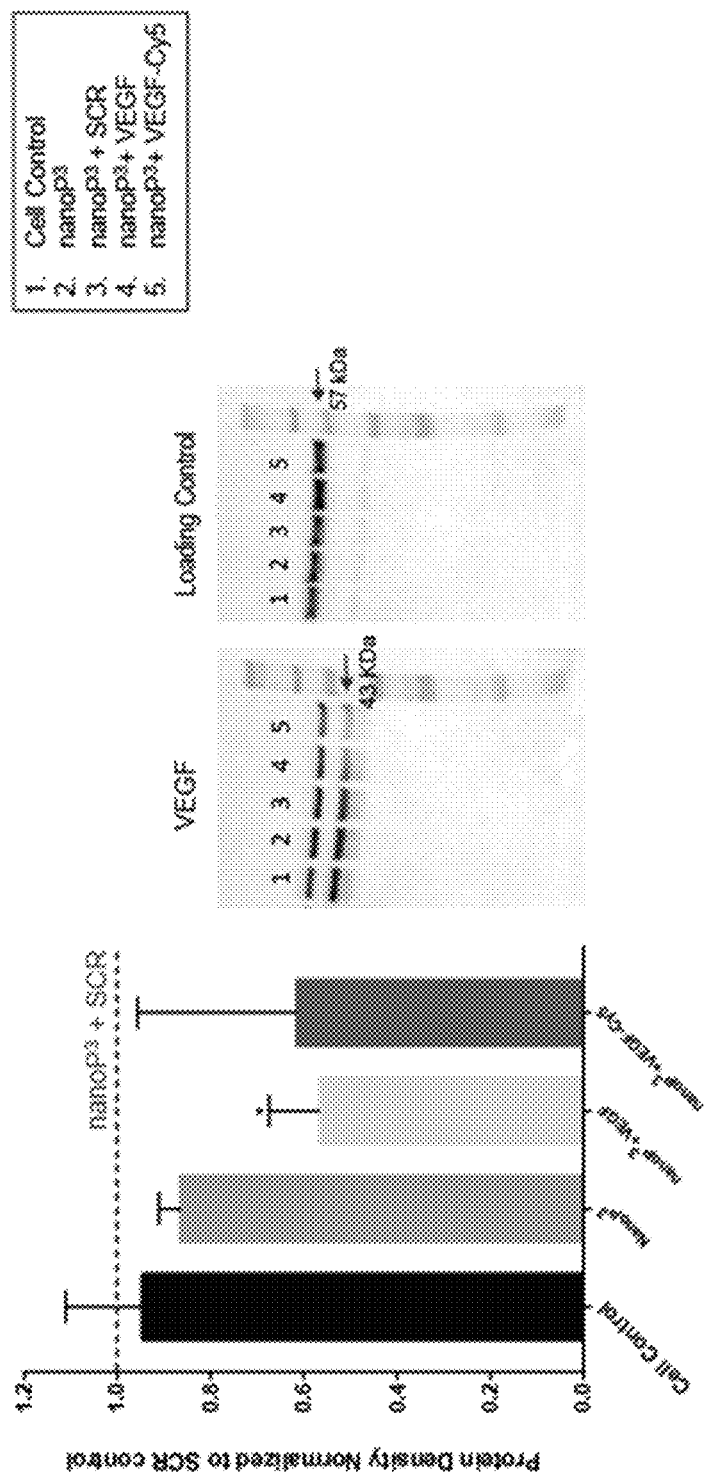
FIG. 59—NanoP$^3$ conjugated with siRNA against VEGF.
Figure 60:
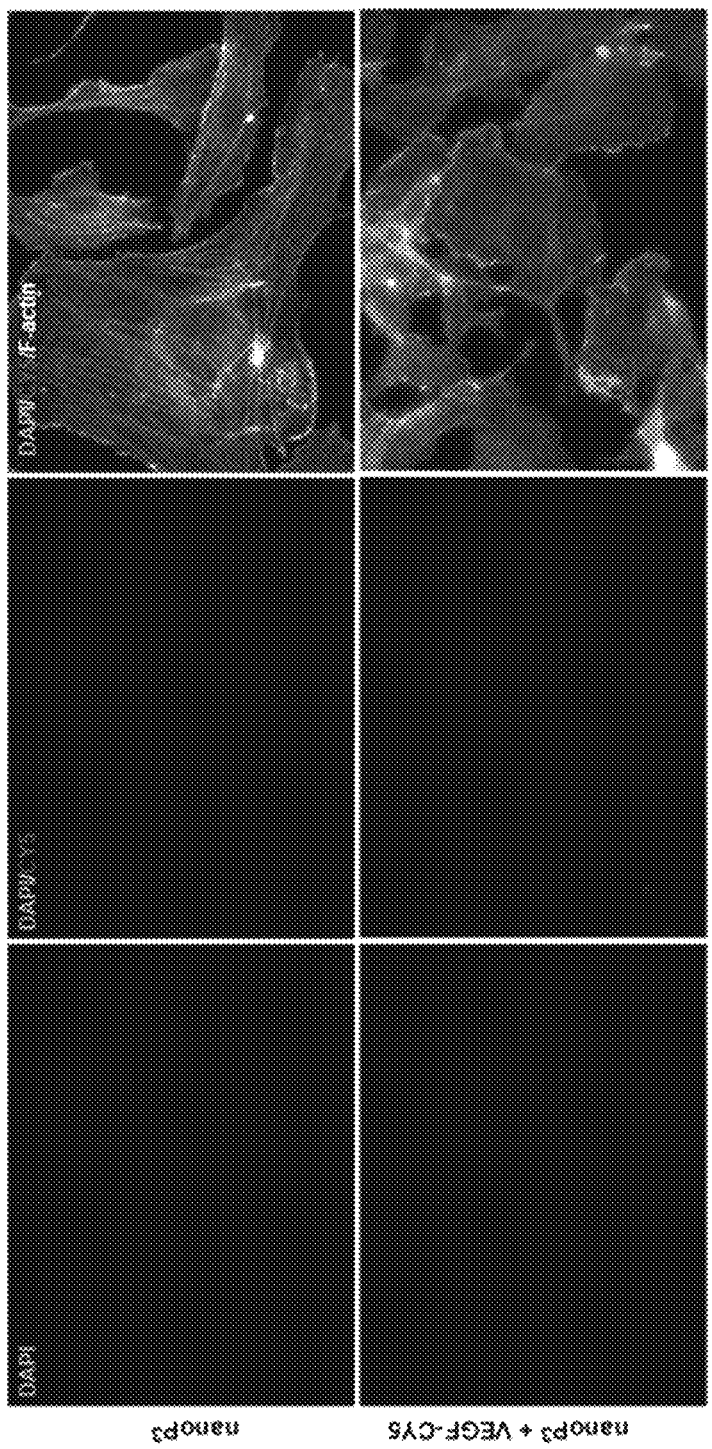
FIG. 60—Stained human umbilical vein endothelial cells after treatment with a conjugate comprising nanoP$^3$ particles and siRNA against VEGF.

Nanoparticles conjugated with siRNA against VEGF (conjugated as generally described in Example 12 above) were successful in significantly reducing VEGF expression in HUVECS after 48 hours by up to 40%, as confirmed by western blot analysis (FIG. 59). The delivery of nanoparticle-siRNA conjugates in HUVEC cells was confirmed by fluorescence microscopy using a siRNA-VEGF tagged with Cy-5 (FIG. 60). This experiment demonstrates that the nanoP$^3$ material disclosed herein can successfully carry siRNA molecules into cells whilst maintaining the biological activity of the siRNA.

Example 19—Conjugation Studies Part 8

Figure 61:
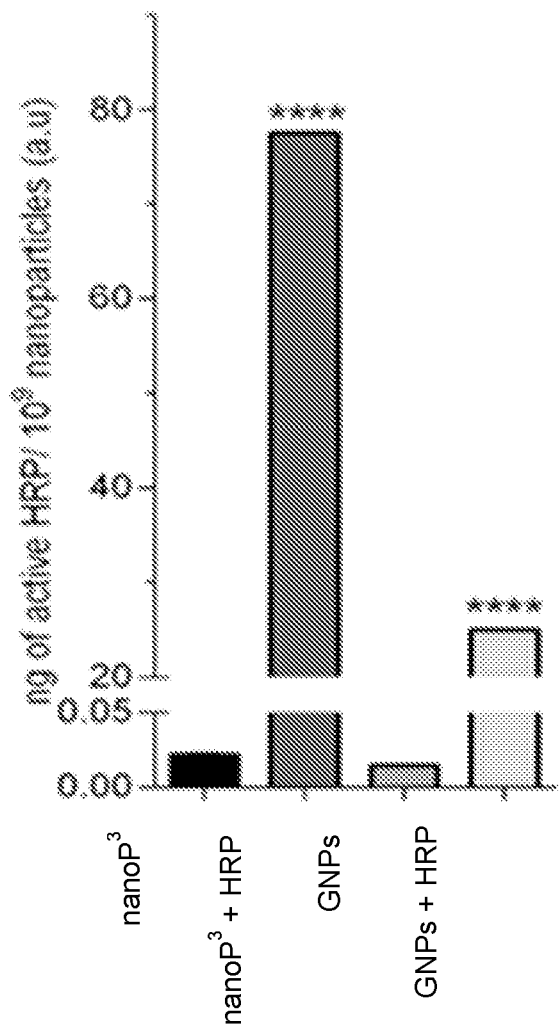
FIG. 61—Conjugation of horseradish peroxidase (HRP) to nanoP$^3$ and gold nanoparticles.

Nanoparticles of nanoP$^3$ and gold (GNPs) were conjugated with horseradish peroxidase (HRP). These were detected by incubation with 2,2'-azino-bis(3-ethylbenzothiazoline-6-sulphonic acid) (ABTS). Detection of the product is performed at 405 nm (FIG. 61) showed a significant amount of HRP conjugated to the nanoP$^3$ material. This experiment provides another example of the successful conjugation of a bioactive protein to the nanoP$^3$ material disclosed herein.

Example 20—siRNA Knockdown Using nanoP$^3$

Figure 62:
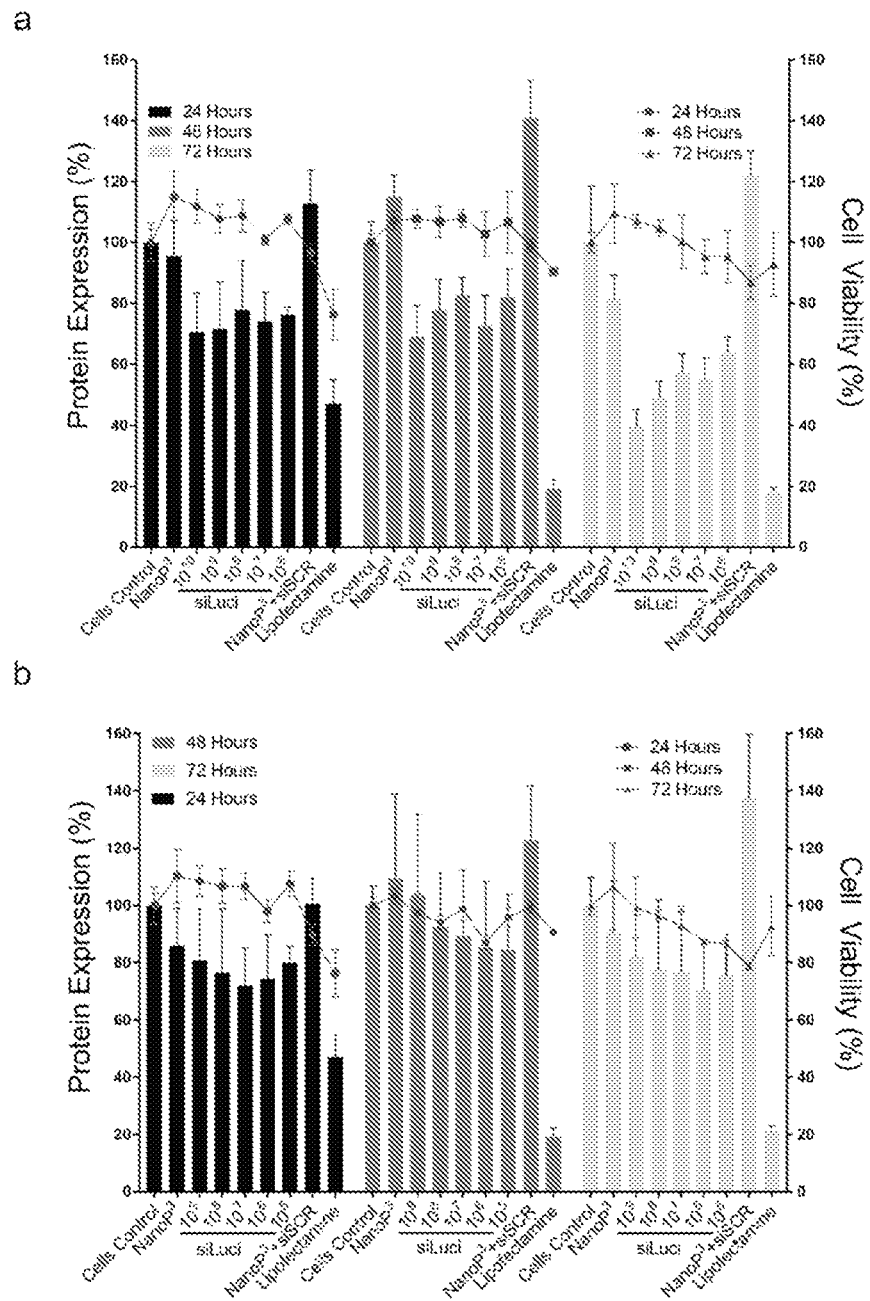
FIG. 62—Delivery of small interfering RNA against Luciferase (siLuci) conjugated to nanoP$^3$ in primary mouse Fibroblasts.
Figure 63:
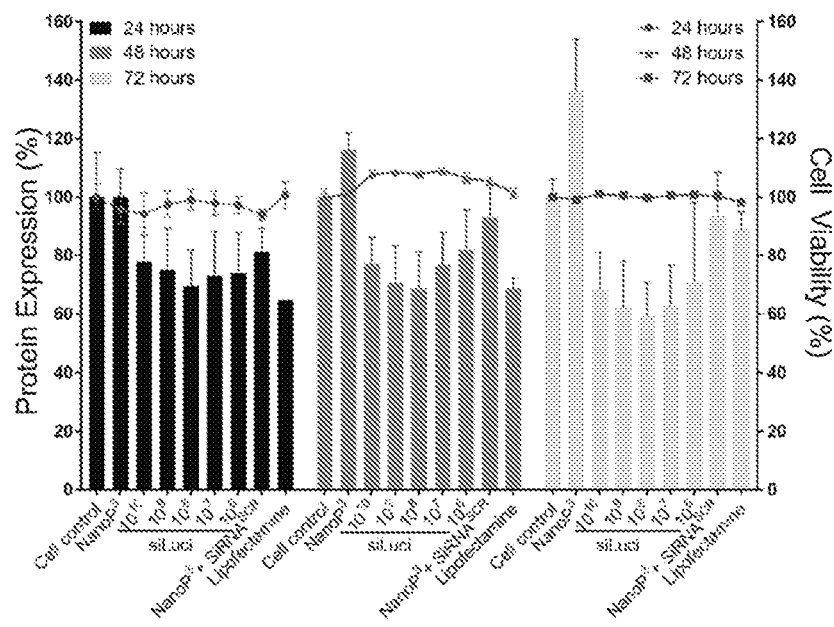
FIG. 63—Delivery of small interfering RNA against Luciferase (siLuci) nanoP$^3$ in IPSC derived Human Endothelial cells.
Figure 63:
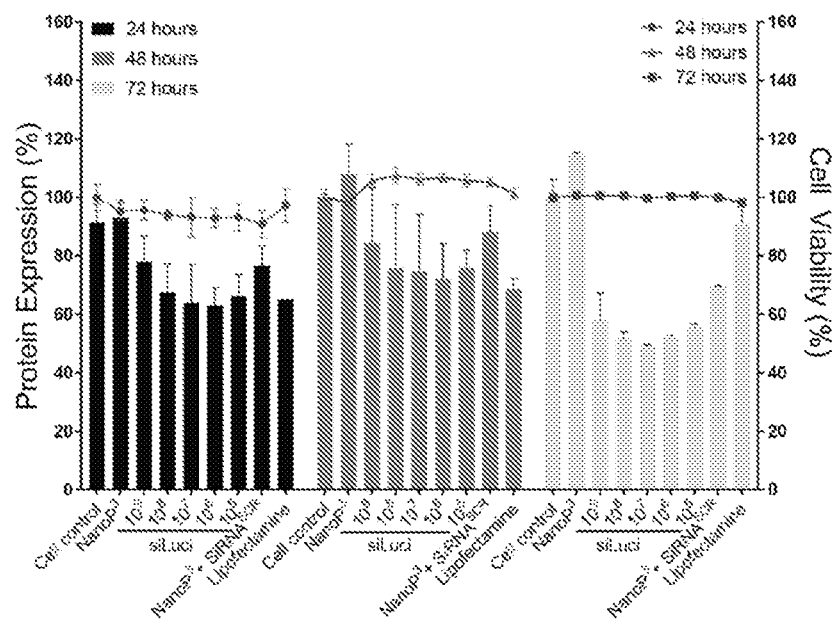

The effect of the delivery of small interfering RNA against Luciferase (siLuci) bound to (a) 100 nm and (b) 200 nm (diameter) nanoP$^3$ in primary mouse fibroblasts was investigated. In FIG. 62, expression of luciferase was significantly reduced at 72 hours to 39.74±6.42% by delivering siLuci with 100 nm nanoP$^3$ at a concentration of $10^{10}$ particles per well compared to untreated cells control. The delivery of scrambled siRNA and unfunctionalized nanoP$^3$ had no significant effect. There was no significant reduction in cell viability observed in all nanoP$^3$ tested groups. The effect of the delivery of small interfering RNA against Luciferase (siLuci) bound to (a) 100 nm and (b) 200 nm (diameter) nanoP$^3$ in IPSC derived Human Endothelial cells was investigated. In FIG. 63, expression of luciferase was significantly reduced at 72 hours to 48.96±1.24% by delivering siLuci with 200 nm nanoP$^3$ at a concentration of $10^7$ particles per well compared to untreated cells control. The delivery of scrambled siRNA and unfunctionalized nanoP$^3$ had no significant effect. There was no significant reduction in cell viability was observed in all nanoP$^3$ tested groups (FIG. 63).

Example 21—Synthesis of Scaffolds for Carrying Nanoparticles

The inventors have utilised electrospun polyurethane scaffolds for carrying nanoP$^3$ materials as defined herein.

Polyurethane (Elast-Eon E2A; 9% (v/w) in hexafluoroisopropanol) was electrospun using 15 kV at 1 mL/hr to a total volume of 2.5 mL and collected using a rotating collector (500 rpm).

A 6×4 cm sheet was then cut into one hundred 3 mm discs, which were subsequently sterilised using ultra violet light (15 mins each side). The discs were separated into 4 treatment groups (25 discs each) and incubated in solution with agitation overnight at 37° C.:

Group 1—Polyurethane (untreated)
Group 2—Polyurethane and nanoparticles ($1 \times 10^9$ mL$^{-1}$)
Group 3: Polyurethane and nanoparticles with vascular endothelial growth factor (VEGF) (1.5 µg/mL, loaded for 4 hours at 4° C.)
Group 4—Polyurethane and nanoparticles with dexamethasone (DEX) (10 µg/mL, loaded for 4 hours at 4° C.)

The discs were thoroughly washed three times after the incubation.

Figure 64:
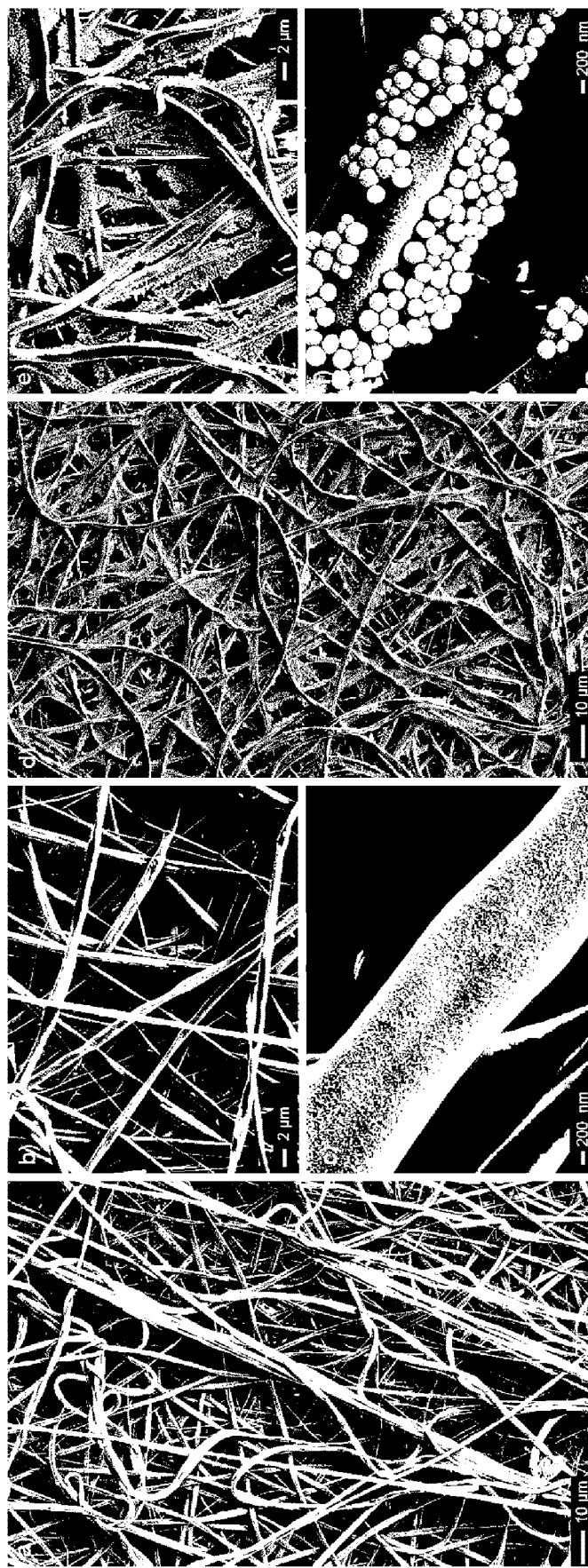
FIG. 64—SEM images of electrospun polyurethane (images a, b and c) and electrospun polyurethane with attached nanoP$^3$ (images d, e and f), at increasing magnifications.

FIG. 64 provides SEM images for the electrospun polyurethane fibres (images a, b and c). Images d, e and f show the incorporation of conjugates of nanoP$^3$ and VEGF.

Figure 65:
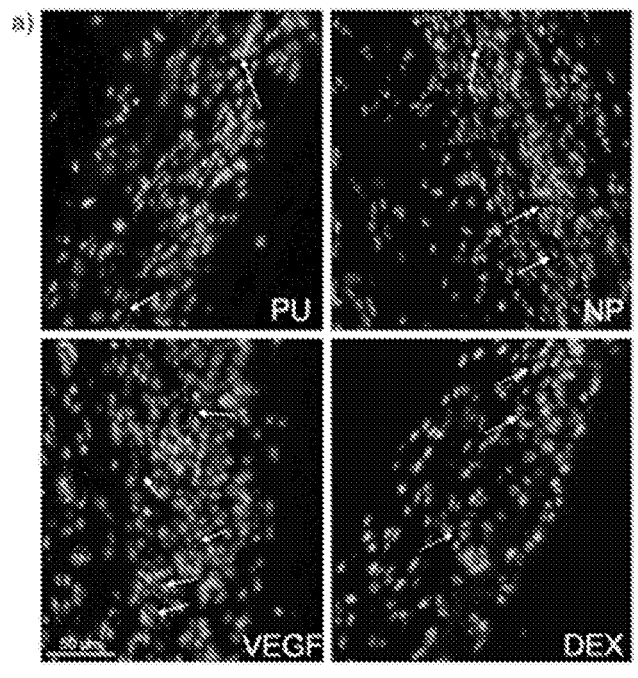
FIG. 65—Endothelial cells treated with an immunofluorescent CD31 and stain at day 14 in the presence of various materials including nanoP$^3$ (a); and average number of neovessels within a capsule following exposure to the materials (b).
Figure 65:
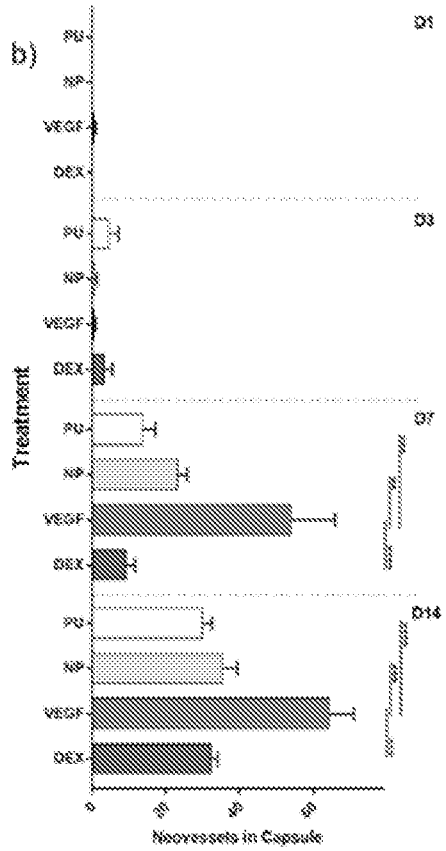

The results of in vivo studies are shown in FIG. 65, which shows the production of neovessels in endothelial cells in image a). Quantification of the results is shown in image b). Significance was calculated using one-way ANOVA (* $p<0.05$,  $p<0.01$, * $p<0.001$, ** $p<0.0001$). In FIG. 65**: PU=polyurethane platform alone (Group 1); NP=polyurethane scaffold with nanoparticles attached (Group 2); VEGF=polyurethane scaffold plus nanoparticles functionalised with VEGF (Group 3); and DEX=polyurethane scaffold plus nanoparticles functionalised with DEX (Group 4).

Figure 66:
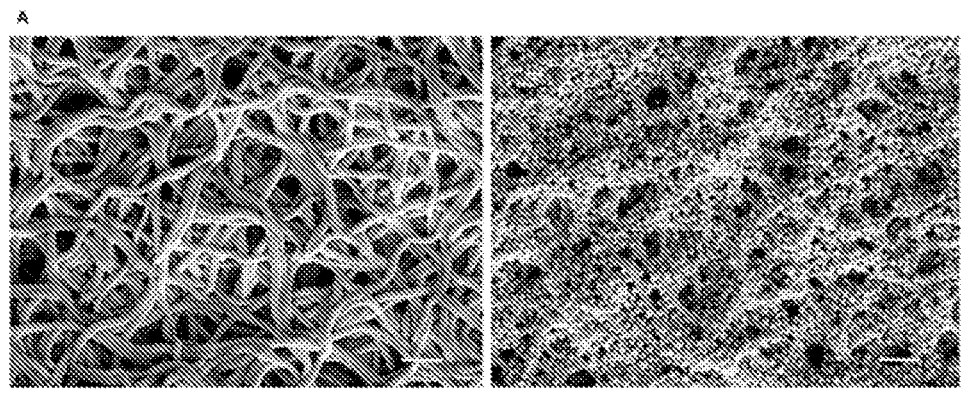
FIG. 66—SEM images of nanoP$^3$ on a silk electrospun scaffold.
Figure 66:
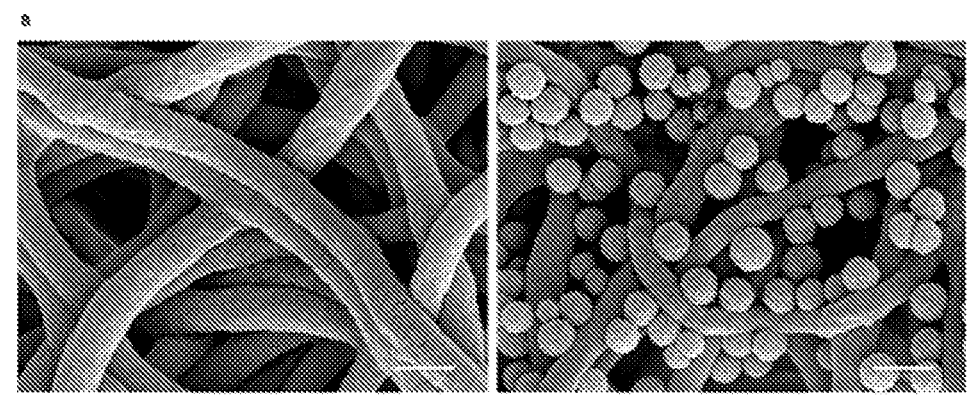

The nanoP$^3$ material can be applied to a broad range of different substrates. For example, the inventors utilised a silk scaffold and were able to show that a uniform distribution of nanoP$^3$ could be obtained (FIG. 66).

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A conjugate comprising:
   an aggregate comprising two or more nanoparticulate polymers having mean diameters of 1 nm to 50 nm, wherein the aggregate has a mean diameter of 5 nm to 500 nm, and wherein the nanoparticulate polymers are formed from a plasma comprising acetylene; and
   at least one species selected from the group consisting of: a pharmaceutical drug, an imaging agent, a photosensitive dye, a cleavable linking molecule, and a hydrocarbon.

2. The conjugate of claim 1, wherein the aggregate is spherical or generally spherical.

3. The conjugate of claim 1, wherein the plasma further comprises one or more monomers selected from: an alkene, a cycloalkene, a cycloalkyne, and mixtures thereof.

4. The conjugate of claim 1, wherein the plasma further comprises at least one gas comprising an element selected from group 15, 16 or 17 of the periodic table, or an inert gas selected from the group consisting of helium, argon, neon, and mixtures thereof.

5. The conjugate of claim 1, wherein the plasma further comprises $N_2$.

6. The conjugate of claim 5, wherein the aggregate comprises at least one substituent selected from the group consisting of: an amine group, an imine group, a nitric oxide group, a nitrile group, and mixtures thereof.

7. The conjugate of claim 1, wherein two or more species are coupled to the aggregate.

8. A pharmaceutical composition comprising:
   an aggregate comprising two or more nanoparticulate polymers having mean diameters of 1 nm to 50 nm, wherein the aggregate has a mean diameter of 5 nm to 500 nm, and wherein the nanoparticulate polymers are formed from a plasma comprising acetylene; and
   at least one species selected from the group consisting of: a pharmaceutical drug, an imaging agent, a photosensitive dye, a cleavable linking molecule, and a hydrocarbon,
   and a pharmaceutically acceptable carrier, excipient, or binder.

9. A method of treating a subject suffering from, susceptible to, or displaying one or more symptoms of a disease, disorder, or condition, the method comprising a step of administering:
   i) a conjugate comprising:
      an aggregate comprising two or more nanoparticulate polymers having mean diameters of 1 nm to 50 nm, wherein the aggregate has a mean diameter of 5 nm to 500 nm, and wherein the nanoparticulate polymers are formed from a plasma comprising acetylene; and
      at least one species selected from the group consisting of: a pharmaceutical drug, an imaging agent, a photosensitive dye, a cleavable linking molecule, and a hydrocarbon, or
   ii) a pharmaceutical composition comprising the conjugate of i) and a pharmaceutically acceptable carrier, excipient or binder,
to the subject,
wherein the disease, disorder, or condition is selected from the group consisting of:
acute coronary syndrome, an aging-related disease or disorder, an allergic disease or a related condition, Alzheimer's disease, asthma, HIV, antibiotic resistance, atherosclerosis, an autoimmune disease, a bacterial infection, cancer, dementia, depression or a related condition, diabetes, dyslipidemia, hyperlipidemia, hypertension, ichthyosis, an immune disease, a metabolic disease or disorder, a neurological disease or disorder, obesity, Parkinson's disease, pain, rheumatoid arthritis, and a proliferative disease.

10. The conjugate of claim 1, wherein the aggregate is crosslinked.

11. The conjugate of claim 1, wherein the at least one species covalently binds to the aggregate.

12. The conjugate of claim 1, wherein the conjugate further comprises a substrate.

13. The conjugate of claim 12, wherein the conjugate is present on at least one surface of the substrate.

14. The conjugate of claim 12, wherein the conjugate is incorporated within the substrate.

15. The conjugate of claim 12, wherein the conjugate is covalently bound to the substrate.

* * * * *